US012551561B2

(12) United States Patent
Kuwae et al.

(10) Patent No.: US 12,551,561 B2
(45) Date of Patent: Feb. 17, 2026

(54) NUCLEIC ACID-CONTAINING LIPID NANO-PARTICLE AND USE THEREOF

(71) Applicant: Takeda Pharmaceutical Company Limited, Osaka (JP)

(72) Inventors: Shinobu Kuwae, Kanagawa (JP); Satoru Matsumoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 515 days.

(21) Appl. No.: 16/958,387

(22) PCT Filed: Dec. 26, 2018

(86) PCT No.: PCT/JP2018/047872

§ 371 (c)(1),
(2) Date: Jun. 26, 2020

(87) PCT Pub. No.: WO2019/131770

PCT Pub. Date: Jul. 4, 2019

(65) Prior Publication Data

US 2021/0052646 A1 Feb. 25, 2021

(30) Foreign Application Priority Data

Dec. 27, 2017 (JP) ................................ 2017-252616

(51) Int. Cl.

| | |
|---|---|
| ***A61K 47/18*** | (2017.01) |
| ***A61K 9/127*** | (2006.01) |
| ***A61K 40/11*** | (2025.01) |
| ***A61K 40/31*** | (2025.01) |
| ***A61K 40/42*** | (2025.01) |
| ***C07K 14/705*** | (2006.01) |
| ***C07K 14/725*** | (2006.01) |
| ***C07K 16/28*** | (2006.01) |
| ***C12N 5/0783*** | (2010.01) |
| ***C12N 5/10*** | (2006.01) |
| *B82Y 5/00* | (2011.01) |

(52) U.S. Cl.

CPC .............. *A61K 47/18* (2013.01); *A61K 9/127* (2013.01); *A61K 40/11* (2025.01); *A61K 40/31* (2025.01); *A61K 40/4211* (2025.01); *C07K 14/7051* (2013.01); *C07K 14/70521* (2013.01); *C07K 16/2809* (2013.01); *C07K 16/2818* (2013.01); *C12N 5/0636* (2013.01); *C12N 5/10* (2013.01); *A61K 2239/31* (2023.05); *A61K 2239/38* (2023.05); *A61K 2239/48* (2023.05); *B82Y 5/00* (2013.01); *C07K 2317/73* (2013.01); *C12N 2510/00* (2013.01)

(58) Field of Classification Search

CPC ...... A61K 9/127; A61K 39/001; A61K 47/18; A61K 35/17; A61K 39/0011; A61K 2039/5158; A61K 9/1272; A61K 2239/31; C07K 14/70; C07K 16/28; C07K 14/7051; C07K 14/70521; C07K 16/2809; C07K 16/2818; C07K 2317/73; C12N 5/0636; C12N 5/10; C12N 2510/00; B82Y 5/00

See application file for complete search history.

(56) References Cited

U.S. PATENT DOCUMENTS

| | | | |
|---|---|---|---|
| 2010/0130588 A1 | 5/2010 | Yaworski et al. | |
| 2012/0276209 A1 | 11/2012 | Cullis et al. | |
| 2013/0064894 A1 | 3/2013 | Martin et al. | |
| 2013/0195920 A1 | 8/2013 | Maier et al. | |
| 2013/0245105 A1 | 9/2013 | De Fougerolles et al. | |
| 2014/0039032 A1 | 2/2014 | Kuboyama et al. | |
| 2014/0045913 A1 | 2/2014 | Kuboyama et al. | |
| 2015/0064242 A1 | 3/2015 | Heyes et al. | |
| 2015/0157565 A1 | 6/2015 | Heartlein et al. | |
| 2016/0145348 A1 | 5/2016 | Stephan | |
| 2016/0151284 A1 | 6/2016 | Heyes et al. | |
| 2016/0311917 A1 | 10/2016 | Beatty et al. | |
| 2016/0375149 A1 | 12/2016 | Irvine et al. | |
| 2017/0197903 A1 | 7/2017 | Hoashi | |
| 2017/0291953 A1 | 10/2017 | Tamada et al. | |
| 2017/0296676 A1* | 10/2017 | Stephan | A61K 39/0011 |
| 2018/0028664 A1 | 2/2018 | Besin et al. | |
| 2018/0244748 A1 | 8/2018 | Gill et al. | |
| 2018/0318409 A1 | 11/2018 | Valiante et al. | |

FOREIGN PATENT DOCUMENTS

| | | |
|---|---|---|
| CN | 102119217 A | 7/2011 |
| CN | 104159615 A | 11/2014 |
| CN | 104519915 A | 4/2015 |

(Continued)

OTHER PUBLICATIONS

Ge et al., "Progress in siRNA delivery in vivo," Chinese Journal of New Drugs, 2010, 19(12):1031-1035, with English abstract.
Moffett et al., "Hit-and-run programming of therapeutic cytoreagents using mRNA nanocarriers," Nature Communications, Aug. 30, 2017, 8:389, 1-13.
De Witte et al., "Requirements for Effective Antitumor Responses of TCR Transduced T Cells," The Journal of Immunology, 2008, 181:5128-5136.
Ramishetti et al., "Systemic Gene Silencing in Primary T Lymphocytes Using Targeted Lipid Nanoparticles," ACS Nano, 2015, 9(7):6706-6716.
Smith et al., "In situ programming of leukaemia-specific T cells using synthetic DNA nanocarriers," Nature Nanotechnology, advance online publication Apr. 17, 2017, 1-10 (Aug. 2017, 12:813-820).

(Continued)

*Primary Examiner* — Nelson B Moseley, II
(74) *Attorney, Agent, or Firm* — Foley & Lardner LLP

(57) ABSTRACT

The present invention provides a lipid nanoparticle containing the following (a) to (c):

(a) a nucleic acid encoding a chimeric antigen receptor (CAR) or an exogenous T cell receptor (TCR);
(b) a cationic lipid; and
(c) a non-cationic lipid.

The present invention also provides a CAR- or exogenous TCR-expressing immunocyte obtained by introducing the lipid nanoparticle into in vivo or ex vivo T cells, and an in vivo or ex vivo therapeutic approach using the immunocytes for disease such as cancer and the like.

17 Claims, 3 Drawing Sheets

(56) References Cited

FOREIGN PATENT DOCUMENTS

| | | | | | |
|---|---|---|---|---|---|
| CN | 107109421 | A | 8/2017 | | |
| JP | 2013-510096 | A | 3/2013 | | |
| JP | 2015-509505 | A | 3/2015 | | |
| JP | 2016-525146 | A | 8/2016 | | |
| JP | 2017-500869 | A | 1/2017 | | |
| WO | WO 2013/051718 | * | 4/2013 | ............. | C12N 15/09 |
| WO | WO-2013/086354 | A1 | 6/2013 | | |
| WO | WO-2014/057432 | A2 | 4/2014 | | |
| WO | WO 2016/021683 | * | 2/2016 | ........... | C07C 229/12 |
| WO | WO-2016/021683 | A1 | 2/2016 | | |
| WO | WO 2016/073629 | * | 5/2016 | ............. | C07K 16/28 |
| WO | WO-2016/189532 | A1 | 12/2016 | | |
| WO | WO-2017/019848 | A1 | 2/2017 | | |
| WO | WO-2017/070618 | A1 | 4/2017 | | |
| WO | WO-2017/099823 | A1 | 6/2017 | | |

OTHER PUBLICATIONS

Wang et al., "Construction and Primary Study on the Anti-Tumor Effect of TCR BV12-3 Recombinant Vector," Progress in Modern Biomedicine, 2014, 14(2):206-208.

Barrett et al., "Chimeric Antigen Receptor- and TCR-Modified T Cells Enter Main Street and Wall Street," J. Immunol., 2015, 195(3):755-761.

Beatty et al., "Mesothelin-specific Chimeric Antigen Receptor mRNA-Engineered T Cells Induce Anti-Tumor Activity in Solid Malignancies," Cancer Immunol. Res., Feb. 1, 2014, 2(2):112-120.

Haj et al., "Tools for translation: non-viral materials for therapeutic mRNA delivery," Nature Reviews Materials, Sep. 12, 2017, 2(10):1-17.

Kaczmarek et al., "Advances in the delivery of RNA therapeutics: from concept to clinical reality," Genome Medicine, Jun. 27, 2017. vol. 9, 1-16.

* cited by examiner

NUCLEIC ACID-CONTAINING LIPID NANO-PARTICLE AND USE THEREOF

CROSS-REFERENCE TO RELATED APPLICATIONS

This application is the U.S. National Stage of PCT/JP2018/047872, filed Dec. 26, 2018, which claims priority to JP 2017-252616, filed Dec. 27, 2017.

TECHNICAL FIELD

The present invention relates to lipid nanoparticles containing a nucleic acid encoding a chimeric antigen receptor or a T cell receptor, a method for expressing a chimeric antigen receptor or an exogenous T cell receptor in a immunocyte of interest by using the lipid nanoparticles, a pharmaceutical use thereof, and the like.

BACKGROUND OF THE INVENTION

The research and development of cancer immunotherapy using CAR-T cells or TCR-T cells introduced with a gene of chimeric antigen receptor (CAR) or T-cell receptor (TCR) derived from cancer antigen-specific killer T cell is progressing rapidly. Current CAR-T cell therapy, such as Kymriah (trade name) and Yescarta (trade name), which were approved in the U.S., generally includes producing CAR-T cells by transfecting T cells collected from patients with CAR genes ex vivo using viral vectors such as lentiviral vector, and administering the CAR-T cells to the patients. However, this method has the problem that the production cost becomes high due to the cost of cell culture and preparation of viral vectors. If introduction of CAR or exogenous TCR selectively into immunocytes, such as T cells, in vivo is possible, ex vivo preparation is not necessary and CAR- or TCR-immunocell therapy with low production cost can be provided. In addition, if CAR or exogenous TCR can be selectively introduced into immunocytes such as T cells in ex vivo without using viral vectors requiring high production cost, the cost of virus residue testing, etc. will be eliminated, and CAR- or TCR-immunocell therapy with low production cost can be provided.

The ex vivo or in vivo transfection of CAR into T cells has been reported which uses nanoparticles containing aggregates of CAR-encoding plasmid DNA and a cationic polymer that are coated with a non-cationic polymer conjugated with anti-CD3 antibody fragments (patent document 1, non-patent document 1), or nanocarrier containing mesoporous silica encapsulating CAR-encoding DNA in the pores and coated with a lipid having a surface modified with an anti-CD3 antibody (patent document 2).

Apart therefrom, techniques have been reported for delivering siRNA to a target cell by encapsulating the target siRNA in "lipid nanoparticles (LNP)", which do not have an internal pore structure and are composed of a cationic lipid, a non-cationic helper lipid, and a ligand for delivery to the target cell. For example, ex vivo or in vivo transfection of siRNA for CD45 into T cells by using an anti-CD4 antibody fragment as a targeted ligand has been reported (patent document 3, non-patent document 2).

To date, however, there is no report that a nucleic acid (e.g., mRNA, DNA) encoding CAR or exogenous TCR has been selectively introduced into immunocytes such as T cells by using LNP.

DOCUMENT LIST

Patent Documents patent document 1: US 2017/0296676
patent document 2: US 2016/0145348
patent document 3: WO 2016/189532

Non-Patent Documents non-patent document 1: Nature Nanotechnology 12, 813-820 (2017)
non-patent document 2: ACS Nano, 2015, 9(7), 6706-6716

SUMMARY OF INVENTION

Technical Problem

The purpose of the present invention is to provide a novel transfection technology capable of efficiently introducing CAR or exogenous TCR selectively into immunocytes such as T cells in vivo or ex vivo, thereby providing CAR- or TCR-immunocell therapy with low production cost. Another purpose of the present invention is to provide a safer CAR- or TCR-immunocell therapy that avoids the problem of antigenicity by viral proteins.

Solution to Problem

The present inventors have conducted intensive studies in an attempt to achieve the above-mentioned purposes and succeeded in efficiently introducing a nucleic acid encoding CAR or exogenous TCR selectively into immunocytes, such as T cell, in vivo and ex vivo by using LNP, which resulted in the completion of the present invention.

Accordingly, the present invention provides the following.

[1] A lipid nanoparticle comprising the following (a) to (c):
(a) a nucleic acid encoding a chimeric antigen receptor or an exogenous T cell receptor;
(b) a cationic lipid; and
(c) a non-cationic lipid.

[2] The lipid nanoparticle of [1], wherein the aforementioned cationic lipid is a compound represented by the formula (I):

(I)

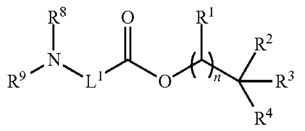

wherein
$L^1$ is a $C_{1-22}$ alkylene group, a $C_{2-22}$ alkenylene group or a $C_{3-22}$ alkadienylene group,
n is an integer of 0 or 1,
$R^1$ is
(1) a hydrogen atom,
(2) a linear $C_{1-22}$ alkyl group optionally substituted by one or two substituents selected from a linear $C_{1-22}$ alkyl group and a linear $C_{2-22}$ alkenyl group, (3) a linear $C_{2-22}$ alkenyl group optionally substituted by one or two substituents selected from a linear $C_{1-22}$ alkyl group and a linear $C_{2-22}$ alkenyl group, or (4) a linear $C_{3-22}$ alkadienyl group optionally substituted by one or two substituents selected from a linear $C_{1-22}$ alkyl group and a linear $C_{2-22}$ alkenyl group, $R^2$ is $—CH_2—O—CO—R^5$, $—CH_2—CO—O—R^5$ or $—R^5$, $R^3$ is $—CH_2—O—CO—R^6$, $—CH_2—CO—O—R^6$ or $—R^6$, $R^4$ is a hydrogen atom, $—CH_2—O—CO—R^7$, $—CH_2—CO—O—R^7$ or $—R^7$, $R^5$, $R^6$ and $R^7$ are each independently (1) a linear $C_{1-22}$ alkyl group optionally substituted by one or two substituents selected from a linear $C_{1-22}$ alkyl group and a linear $C_{2-22}$ alkenyl group, (2) a linear $C_{2-22}$ alkenyl group optionally substituted by one or two substituents selected from a linear $C_{1-22}$ alkyl group and a linear $C_{2-22}$ alkenyl group, or (3) a linear $C_{3-22}$ alkadienyl group optionally substituted by one or two substituents selected from a linear $C_{1-22}$ alkyl group and a linear $C_{2-22}$ alkenyl group, $R_8$ and $R_9$ are each independently, a $C_{1-6}$ alkyl group, or a salt thereof.

[3] The lipid nanoparticle of [1] or [2], wherein the aforementioned nucleic acid is mRNA or DNA.

[4] The lipid nanoparticle of any of [1] to [3], wherein the aforementioned non-cationic lipid is phospholipid, cholesterol and/or PEG lipid.

[5] The lipid nanoparticle of any of [1] to [4], wherein the aforementioned lipid nanoparticle has a ligand that can be targeted to T cells on the surface.

[6] The lipid nanoparticle of [5], wherein the aforementioned ligand is a ligand comprising an antigen binding domain of one or more antibodies selected from the group consisting of an antibody against CD3, an antibody against CD4, an antibody against CD8 and an antibody against CD28.

[7] The lipid nanoparticle of [5], wherein the aforementioned ligand is a ligand comprising an antigen binding domain of an antibody against CD3 and/or an antibody against CD28.

[8] The lipid nanoparticle of [5], wherein the aforementioned ligand is a ligand comprising an antigen binding domain of an antibody against CD3 and an antibody against CD28.

[9] A medicament comprising the lipid nanoparticle of any of [1] to [8].

[10] The medicament of [9], wherein the medicament is a prophylactic or therapeutic drug for cancer.

[11] The medicament of [9], wherein the medicament introduces a chimeric antigen receptor or an exogenous T cell receptor gene into an in vivo immunocyte to induce an expression thereof.

[12] The medicament of [9], wherein the medicament introduces a chimeric antigen receptor or an exogenous T cell receptor gene into an in vivo T cell to induce an expression thereof.

[13] A method for expressing a chimeric antigen receptor or an exogenous T cell receptor by introducing the receptor into an in vivo immunocyte of a mammal, comprising administering the lipid nanoparticle of any of [1] to [8] to the mammal.

[14]

A method for expressing a chimeric antigen receptor or an exogenous T cell receptor by introducing the receptor into an in vivo T cell of a mammal, comprising administering the lipid nanoparticle of any of [1] to [8] to the mammal.

[15] A method for preventing or treating cancer in a mammal, comprising administering the lipid nanoparticle of any of [1] to [8] to the mammal.

[16] The lipid nanoparticle of any of [1] to [8] for use in the prophylaxis or treatment of cancer.

[17] Use of the lipid nanoparticle of any of [1] to [8] in the manufacture of an agent for the prophylaxis or treatment of cancer.

[18] A composition for inducing expression of a chimeric antigen receptor or an exogenous T cell receptor, comprising the lipid nanoparticle of any of [1] to [8].

[19] An ex vivo immunocyte that expresses a chimeric antigen receptor or an exogenous T cell receptor and is obtained by adding the lipid nanoparticle of any of [1] to [8] to a culture comprising an ex vivo immunocyte.

[20] An ex vivo T cell that expresses a chimeric antigen receptor or an exogenous T cell receptor and is obtained by adding the lipid nanoparticle of any of [1] to [8] to a culture comprising an ex vivo T cell.

[21] A medicament comprising an ex vivo immunocyte that expresses a chimeric antigen receptor or an exogenous T cell receptor and is obtained by adding the lipid nanoparticle of any of [1] to [8] to a culture comprising an ex vivo immunocyte.

[22] A medicament comprising an ex vivo T cell that expresses a chimeric antigen receptor or an exogenous T cell receptor and is obtained by adding the lipid nanoparticle of any of [1] to [8] to a culture comprising an ex vivo T cell.

[23] The medicament of [21] or [22], wherein the medicament is a prophylactic or therapeutic drug for cancer.

[24] The medicament of [21] or [22], wherein the medicament is a drug for inducing apoptosis.

[25] A method for expressing a chimeric antigen receptor or an exogenous T cell receptor by introducing the receptor into an en vivo immunocyte, comprising adding the lipid nanoparticle of any of [1] to [8] to a culture comprising an ex vivo immunocyte.

[26] A method for expressing a chimeric antigen receptor or an exogenous T cell receptor in an en vivo T cell, comprising adding the lipid nanoparticle of any of [1] to [8] to a culture comprising an ex vivo T cell.

[27] A method for preventing or treating cancer in a mammal, comprising administering, to the mammal, an ex vivo immunocyte that expresses a chimeric antigen receptor or an exogenous T cell receptor and is obtained by adding the lipid nanoparticle of any of [1] to [8] to a culture comprising an ex vivo immunocyte.

[28] A method for preventing or treating cancer in a mammal, comprising administering, to the mammal, an ex vivo T cell that expresses a chimeric antigen receptor or an exogenous T cell receptor and is obtained by adding the lipid nanoparticle of any of [1] to [8] to a culture comprising an ex vivo T cell.

[29] An ex vivo immunocyte for use in the prophylaxis or treatment of cancer, wherein the ex vivo immunocyte expresses a chimeric antigen receptor or an exogenous T cell receptor and is obtained by adding the lipid nanoparticle of any of [1] to [8] to a culture comprising an ex vivo immunocyte.

[30] An ex vivo T cell for use in the prophylaxis or treatment of cancer, wherein the ex vivo T cell expresses a chimeric antigen receptor or an exogenous T cell receptor and is obtained by adding the lipid nanoparticle of any of [1] to [8] to a culture comprising an ex vivo T cell.

[31] Use of an ex vivo immunocyte in the manufacture of an agent for the prophylaxis or treatment of cancer, wherein the ex vivo immunocyte expresses a chimeric antigen receptor or an exogenous T cell receptor and is obtained by adding the lipid nanoparticle of any of [1] to [8] to a culture comprising an ex vivo immunocyte.

[32] Use of an ex vivo T cell in the manufacture of an agent for the prophylaxis or treatment of cancer, wherein the ex vivo T cell expresses a chimeric antigen receptor or an exogenous T cell receptor and is obtained by adding the lipid nanoparticle of any of [1] to [8] to a culture comprising an ex vivo T cell.

[33] A method for producing a medicament comprising an ex vivo immunocyte that expresses a chimeric antigen receptor or an exogenous T cell receptor, comprising a step of adding the lipid nanoparticle of any of [1] to [8] to a culture comprising an ex vivo immunocyte.

[34] A method for producing a medicament comprising an ex vivo T cell that expresses a chimeric antigen receptor or an exogenous T cell receptor, comprising a step of adding the lipid nanoparticle of any of [1] to [8] to a culture comprising an ex vivo T cell.

Advantageous Effects of Invention

According to the present invention, CAR or exogenous TCR can be efficiently introduced selectively into immunocytes, such as T cells, not only ex vivo but also in vivo, and CAR- or TCR-immunocell therapy with low production cost can be provided. In addition, since a virus vector is not used, the problem of antigenicity by viral proteins can be avoided.

DETAILED DESCRIPTION OF THE INVENTION

Figure 1:
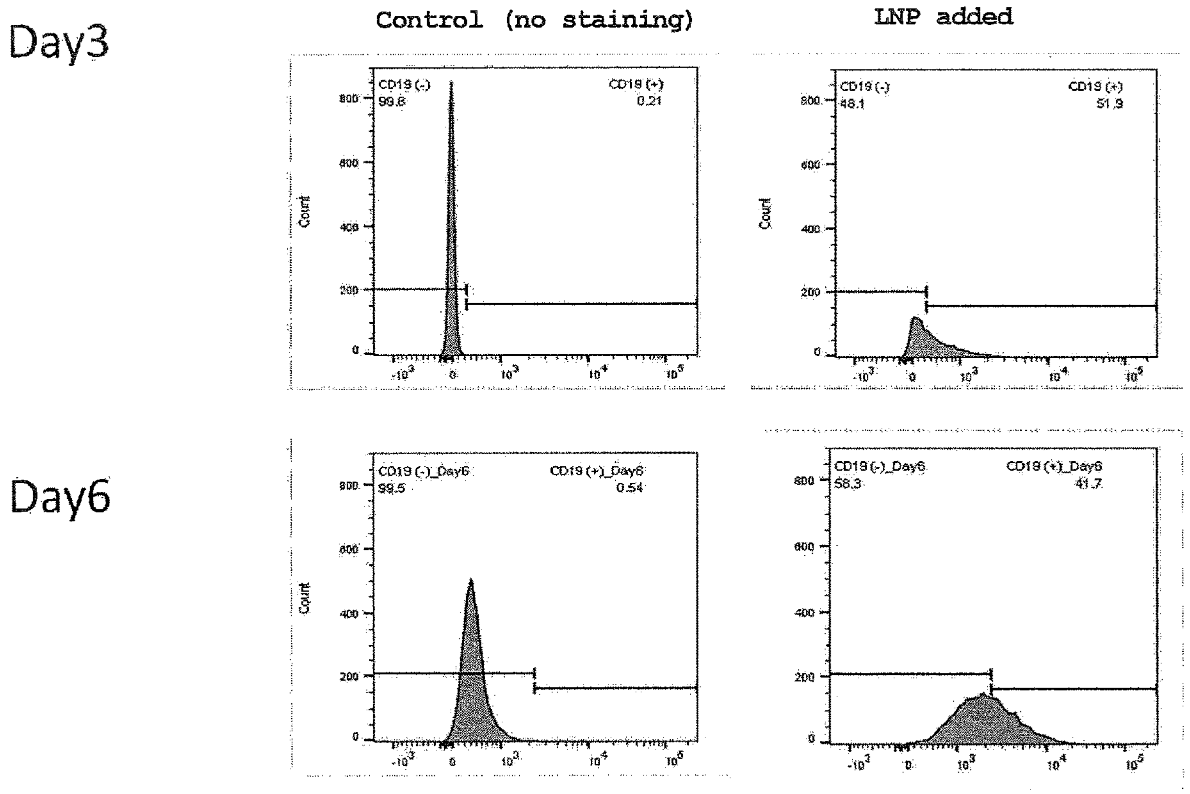
FIG. 1 shows the flow cytometry analysis results of CD19 CAR expression in cultured human primary T cells transfected with hCD3/hCD28-compound 12-pcDNA3.1-hCD19CAR.

1. Lipid Nanoparticle of the Present Invention (LNP)

The present invention provides lipid nanoparticles containing the following (a) to (c):

(a) a nucleic acid encoding a chimeric antigen receptor (CAR) or an exogenous T cell receptor (TCR);

(b) a cationic lipid; and (c) a non-cationic lipid (hereinafter to be also referred to as "the lipid nanoparticle of the present invention", "LNP of the present invention").

In the present specification, the "lipid nanoparticle (LNP)" refers to particles with an average diameter of less than 1 μm and free of a small porous structure (e.g., mesoporous material) in a molecular assembly constituted of the above-mentioned (b) and (c).

The constituent elements (a) to (c) of the lipid nanoparticle of the present invention are explained below.

(a) Nucleic Acid Encoding Chimeric Antigen Receptor (CAR) or Exogenous T Cell Receptor (TCR)

(a-1) Nucleic Acid Encoding CAR

CAR is an artificially constructed hybrid protein containing the antigen-binding domain (e.g., scFv) of an antibody coupled to a T cell signal transduction domain. CAR is characterized by the ability to utilize the antigen-binding property of the monoclonal antibody to redirect the specificity and responsiveness of T cells to a selected target in a non-MHC-restricted manner. Non-MHC-restricted antigen recognition confers on CAR-expressing T cells the ability to recognize antigens independently of antigen processing, thereby bypassing the major mechanism of tumor escape. Furthermore, when expressed in T cells, CAR advantageously does not dimerize with the endogenous TCR α chain and β chain.

The CAR used in the lipid nanoparticles of the invention includes an antigen-binding domain, an extracellular hinge domain, a transmembrane domain, and an intracellular T cell signal transduction domain of an antibody that can specifically recognize surface antigens (e.g., cancer antigen peptide, surface receptor showing promoted expression in cancer cells, etc.) that the target immunocyte (e.g., T cell, NK cell, NKT cell, monocyte, macrophage, dendritic cell, etc.) should recognize.

Examples of the surface antigens specifically recognized by antigen-binding domains include, but are not limited to, surface receptors showing promoted expression in various cancers (e.g., acute lymphocytic cancer, alveolar rhabdomyosarcoma, bladder cancer, bone cancer, brain cancer (e.g., medulloblastoma), breast cancer, anus, anal canal or anorectal cancer, cancer of the eye, cancer of the interhepatic bile duct, joint cancer, cervical, gallbladder or pleural cancer, nose, nasal cavity or middle ear cancer, oral cancer, vulvar cancer, chronic myelogenous cancer, colon cancer, esophageal cancer, cervical cancer, fibrosarcoma, gastrointestinal carcinoid tumor, head and neck cancer (e.g., head and neck squamous cell carcinoma), hypopharyngeal cancer, kidney cancer, laryngeal cancer, leukemia (e.g., acute lymphoblastic leukemia, acute lymphocytic leukemia, chronic lymphocytic leukemia, acute myeloid leukemia), liquid tumor, liver cancer, lung cancer (e.g., non-small cell lung cancer), lymphoma (e.g., Hodgkin lymphoma, non-Hodgkin lymphoma, diffuse large B cell lymphoma, follicular lymphoma), malignant mesothelioma, mastocytoma, melanoma, multiple myeloma, nasopharyngeal cancer, ovarian cancer, pancreatic cancer; peritoneal, omentum and mesenteric cancer; pharyngeal cancer, prostate cancer, rectal cancer, renal cancer, skin cancer, small intestine cancer, soft tissue cancer, solid tumor, gastric cancer, testicular cancer, thyroid cancer, ureteral cancer and the like, for example, CD19, EGF receptor, BCMA, CD30, Her2, ROR1, MUC16, CD20, mesothelin, B-cell mutation antiten (BCMA), CD123, CD3, prostate specific membrane antigen (PSMA), CD33, MUC-1, CD138, CD22, GD2, PD-L1, CEA, chondroitin sulfate proteoglycan-4, IL-13 receptor α chain, IgG κ light chain, and cancer antigen peptides (e.g., peptides derived from WT1, GPC3, MART-1, gp100, NY-ESO-1, MAGE-A4, etc.).

The antigen-binding domain used in the present invention is not particularly limited as long as it is an antibody fragment that can specifically recognize the target antigen. Considering the ease of preparation of CAR, a single-chain antibody (scFv) in which a light chain variable region and a heavy chain variable region are linked via a linker peptide is desirable. The configuration of the light chain variable region and heavy chain variable region in single-chain antibody is not particularly limited as long as they can reconstitute a functional antigen-binding domain. They can generally be designed in the order of light chain variable region, linker peptide, and heavy chain variable region from the N-terminal side. As the linker peptide, a known linker peptide typically used for the production of single-chain antibodies can be used. For example, DNA encoding light chain variable region and heavy chain variable region can be prepared by cloning light chain gene and heavy chain gene respectively from antibody-producing cells and performing PCR using them as templates, or the like, or by chemically synthesizing them from the sequence information of existing antibodies. DNA encoding a single-chain antibody can be obtained by ligating each obtained DNA fragment with a DNA encoding linker peptide by an appropriate method. The N-terminal side of the antigen-binding domain is preferably further added with a reader sequence to present CAR to the surface of the immunocyte.

As the extracellular hinge domain and transmembrane domain, T cell surface molecule-derived domains generally used in the relevant technical field can be used as appropriate. For example, they include, but are not limited to, domains derived from CD8α and CD28.

Examples of the intracellular signal transduction domain include, but not limited to, those having a CD3ζ chain, those further having a co-stimulatory motif such as CD28, CD134, CD137, Lck, DAP10, ICOS, 4-1BB, and the like between the transmembrane domain and the CD3ζ chain, and those having two or more co-stimulatory motifs. Any domains normally used in the relevant technical field can be used in combination.

Nucleic acid sequence information encoding extracellular hinge domain, transmembrane domain, and intracellular signaling domain is well known in the relevant technical field. Those of ordinary skill in the art can easily obtain DNA fragments encoding each domain from T cells based on such information.

DNA encoding CAR can be obtained by linking DNA fragments respectively encoding the thus-obtained antigen binding domain, extracellular hinge domain, transmembrane domain, and intracellular signal transduction domain, by a conventional method.

The obtained DNA encoding CAR can be inserted into an expression vector, preferably a plasmid vector, containing a functional promoter in T cells, either as is or after adding a suitable linker and/or nuclear translocation signal and the like. Examples of the functional promoter in T cells include, but are not limited to, constitutive SRα promoter in mammalian cells, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like. In addition, gene promoters such as CD3, CD4, and CD8, which are specifically expressed in T cells, can also be used.

RNA encoding a CAR, preferably mRNA, can be prepared by transcription into mRNA in an in vitro transcription system known per se using an expression vector containing DNA encoding the above-mentioned CAR as a template.

(a-2) Nucleic Acid Encoding Exogenous TCR

In the present specification, the “T cell receptor (TCR)” means a receptor that consists of dimers of the TCR chain (α-chain, β-chain) and recognizes an antigen or the antigen-HLA (human leukocyte type antigen) (MHC; major histocompatibility complex) complex and transduces a stimulatory signal to T cells. Each TCR chain consists of a variable region and a constant region, and the variable region contains three complementarity determining regions (CDR1, CDR2, CDR3). The TCR used in the present invention includes not only those in which the α and β chains of the TCR constitute a heterodimer but also those in which they constitute a homodimer. Furthermore, the TCR includes those with a part or all of the constant regions deleted, those with recombined amino acid sequence, and those with soluble TCR, and the like.

The “exogenous TCR” means being exogenous to T cell, which is the target cell of the lipid nanoparticle of the present invention. The amino acid sequence of the exogenous TCR may be the same as or different from that of the endogenous TCR expressed by T cell, which is the target cell of the lipid nanoparticle of the present invention.

The nucleic acid encoding TCR used in the lipid nanoparticle of the invention is a nucleic acid encoding the α chain and β chain of TCR that can specifically recognize surface antigens (e.g., cancer antigen peptide etc.) to be recognized by the target T cell.

The nucleic acid can be prepared by a method known per se. When the amino acid sequence or nucleic acid sequence of the desired TCR is known, a DNA encoding the full-length or a part of the TCR of the present invention can be constructed based on the sequence by, for example, chemically synthesizing a DNA strand or an RNA strand, or connecting a synthesized, partially overlapping oligo-DNA short strand by the PCR method or the Gibson assembly method.

When the sequence of the desired TCR is not known, for example, T cell of interest is isolated from a population of cells containing the T cell expressing a TCR of interest, and a nucleic acid encoding the TCR can be obtained from the T cell. Specifically, a cell population (e.g., PBMC) containing T cells is collected from an organism (e.g., human), the cell population is cultured in the presence of epitopes of cell surface antigens recognized by the target TCR while stimulating the cell population, and T cell that specifically recognizes cells expressing the cell surface antigen can be selected from the cell population by a known method and using, as indices, specificity for cells expressing the cell surface antigen and cell surface antigens such as CD8 and CD4. The specificity for cells expressing the cell surface antigen of T cells can be measured, for example, by dextromer assay, ELISPOT assay, cytotoxic assay, or the like. The aforementioned cell population containing T cells is preferably collected from, for example, an organism having a large number of cells expressing a cell surface antigen recognized by the TCR of interest (e.g., patient with a disease such as cancer, or T cell-containing population contacted with an epitope of the antigen or dendritic cells pulsed with the epitope).

The nucleic acid of the present invention can be obtained by extracting DNA from the aforementioned isolated T cell by a conventional method, amplifying and cloning the TCR gene based on the nucleic acid sequence of the constant region of the TCR by using the DNA as a template. It can also be prepared by extracting RNA from a cell and synthesizing cDNA by a conventional method, and performing 5'-RACE (rapid amplification of cDNA ends) with the cDNA as templates using antisense primers complementary to the nucleic acids respectively encoding the constant regions of the TCR α chain and β chain. 5'-RACE may be performed by a known method and can be performed, for example, using a commercially available kit such as SMART PCR cDNA Synthesis Kit (manufactured by clontech). The DNA encoding the α chain and β chain of the obtained TCR can be inserted into an appropriate expression vector in the same way as the DNA encoding the above-mentioned CAR. The DNA encoding α chain and the DNA encoding β chain may be inserted into the same vector or separate vectors. When inserted into the same vector, the expression vector may express both strands in a polycistronic or monocistronic manner. In the former case, an intervening sequence that permits polyscystronic expression, such as IRES or FMV 2A, is inserted between the DNA encoding both strands.

In addition, RNA encoding each strand of the TCR, preferably mRNA, can be prepared in the same way as the above-mentioned RNA encoding CAR, for example, by using the expression vector as a template.

(b) Cationic Lipid

In the present specification, the "cationic lipid" means a lipid that has a net positive charge at a selected pH, such as physiological pH. The cationic lipids used in the lipid nanoparticle of the present invention are not particularly limited. For example, cationic lipids and the like described in WO 2015/011633, WO 2016/021683, WO 2011/153493, WO 2013/126803, WO 2010/054401, WO 2010/042877, WO 2016/104580, WO 2015/005253, WO 2014/007398, WO 2017/117528, WO 2017/075531, WO 2017/00414, WO 2015/199952, US 2015/0239834, and the like can be mentioned.

Preferred cationic lipids are represented by the following structural formulas and described in WO 2015/011633.

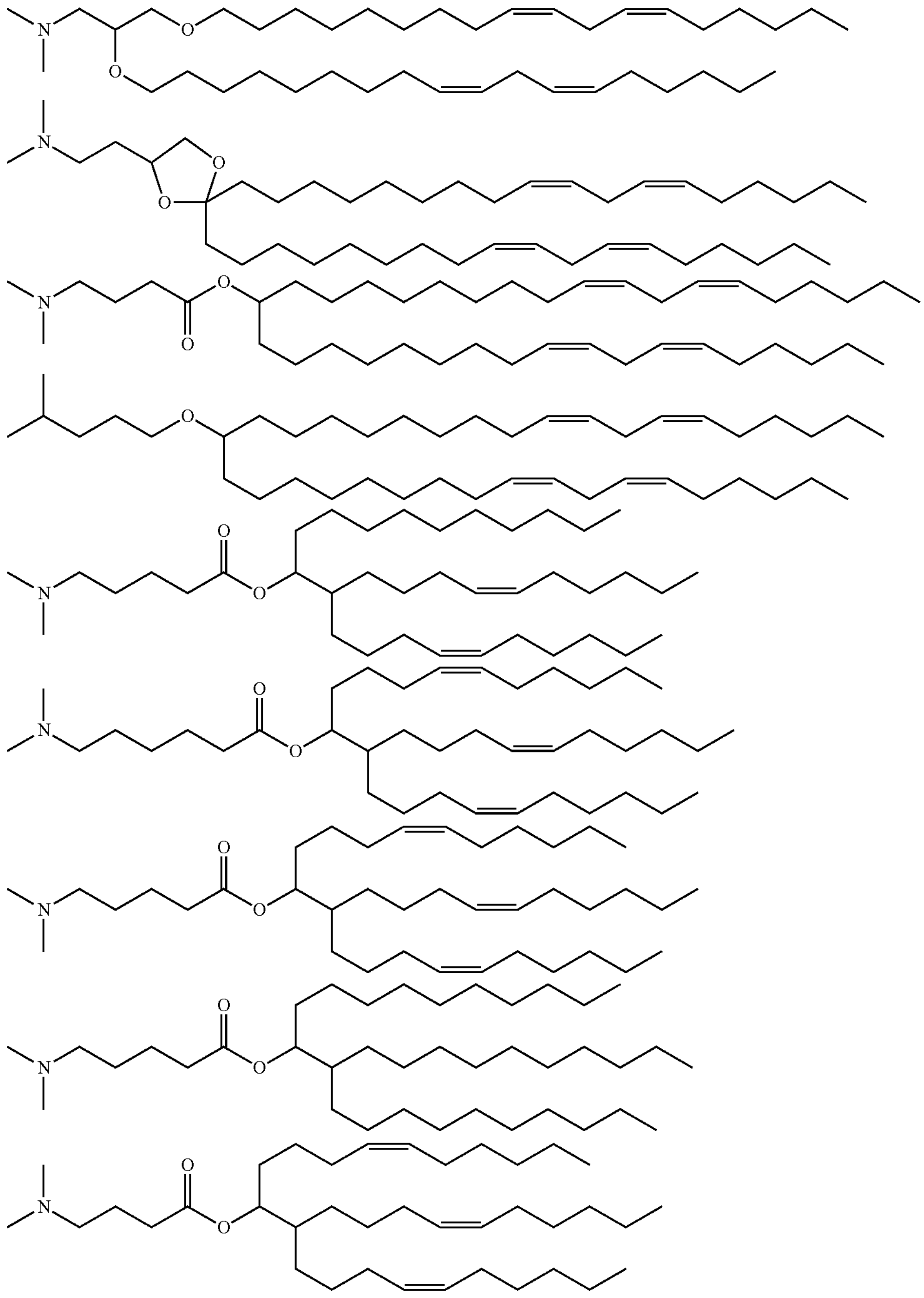

-continued
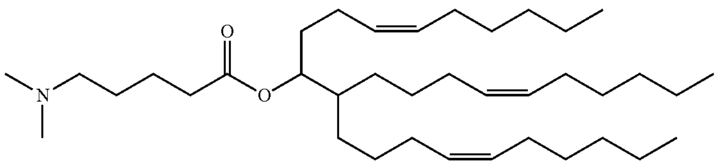
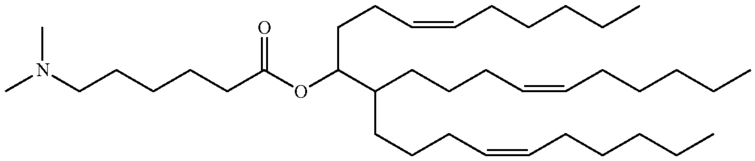
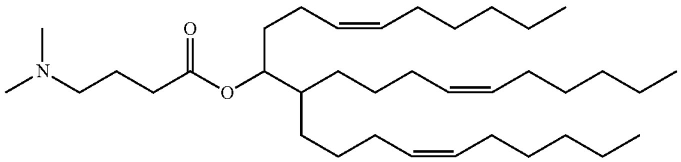
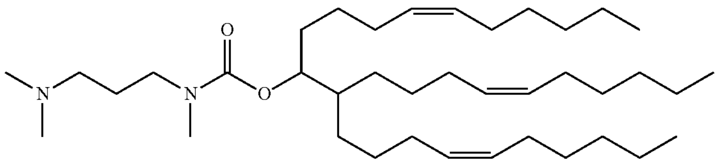
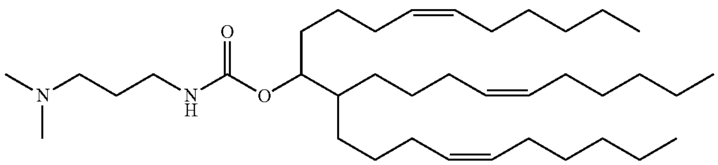
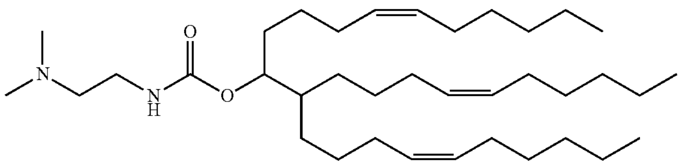
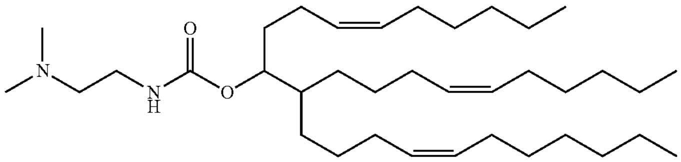
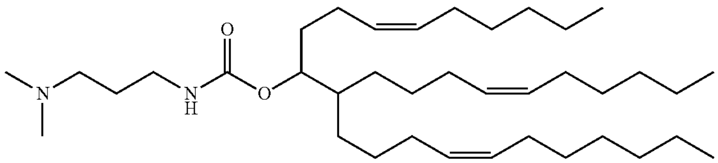
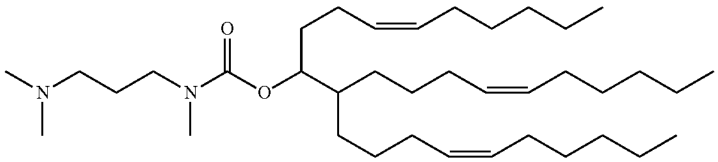
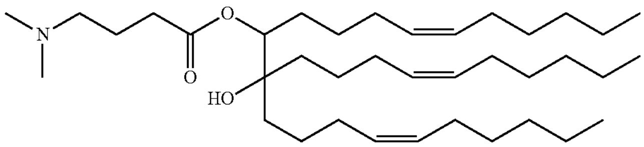

-continued
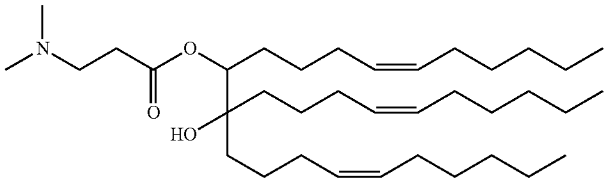
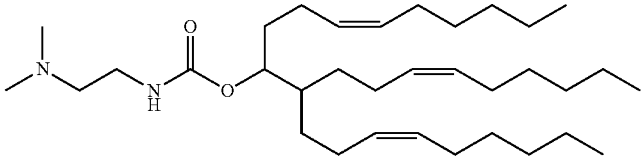
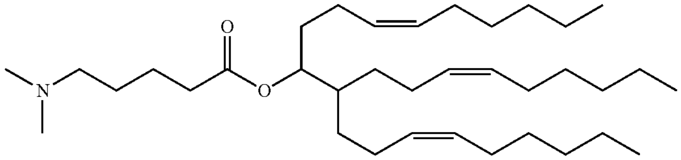
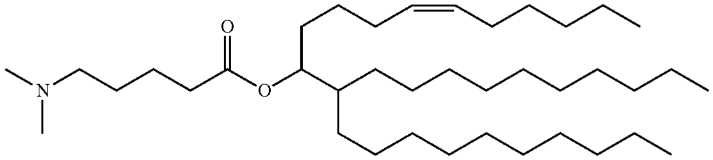
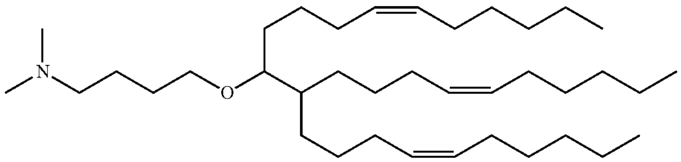
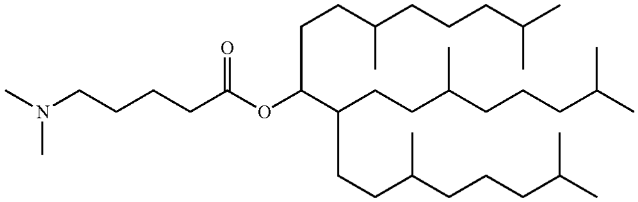
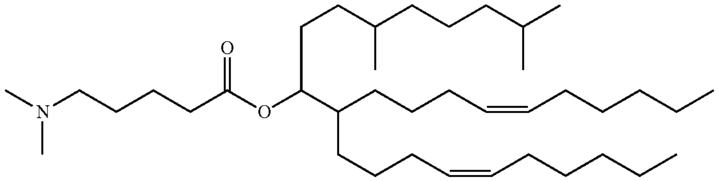
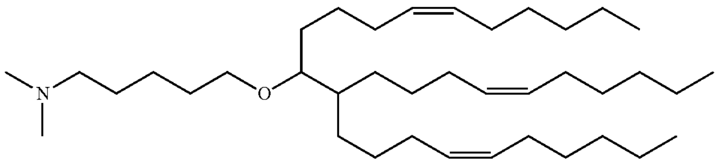
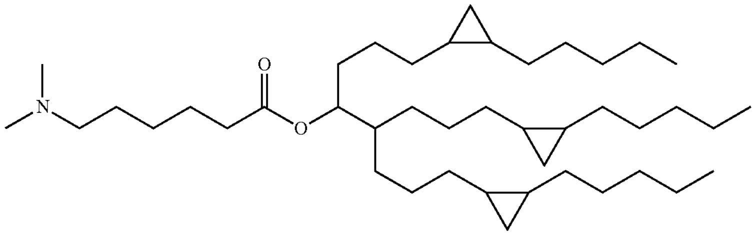

-continued
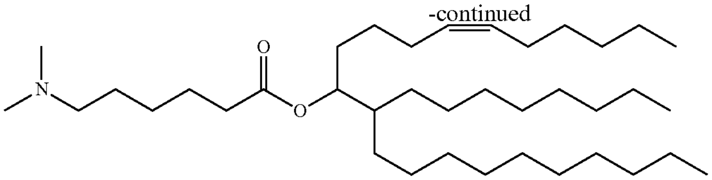
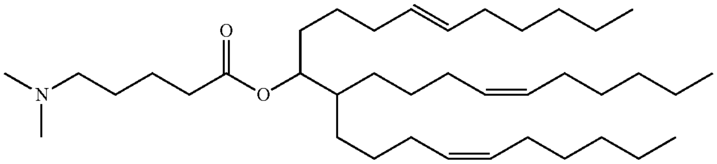
and
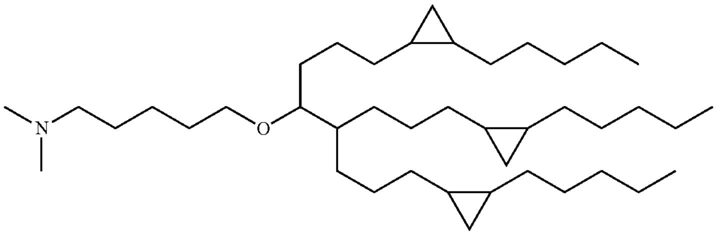
and salts thereof.
Among the above-mentioned cationic lipids, cationic lipids represented by the following structural formulas are more preferred.
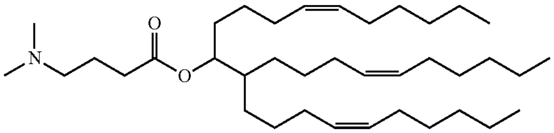
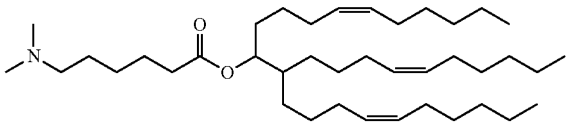
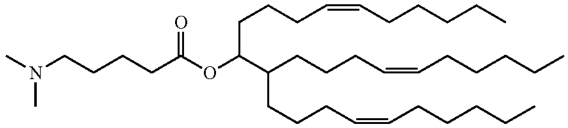
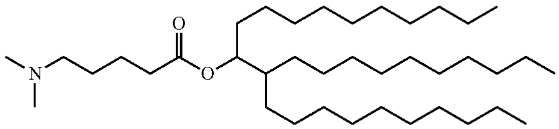
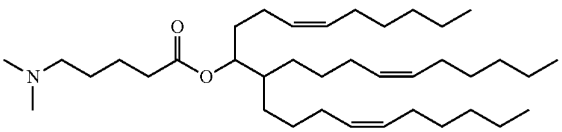
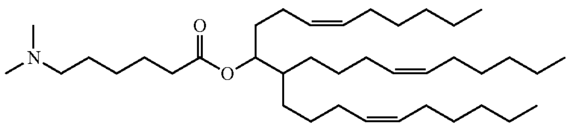
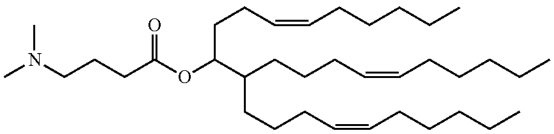
-continued
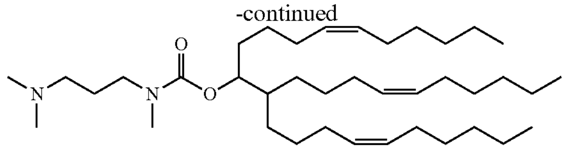
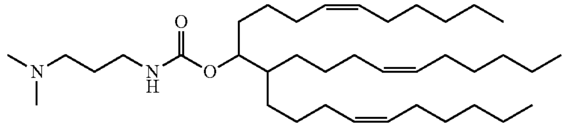
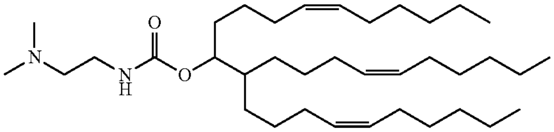
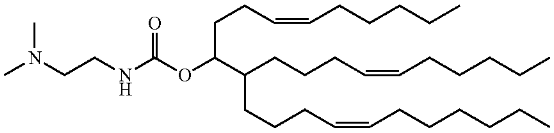
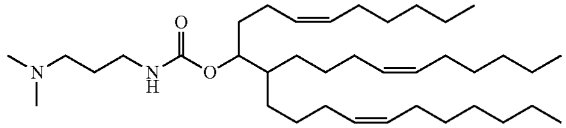
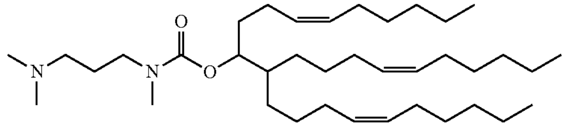
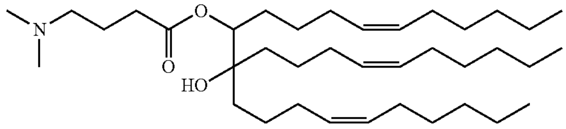
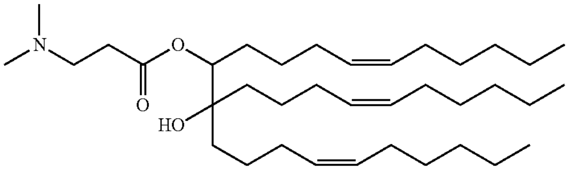

-continued

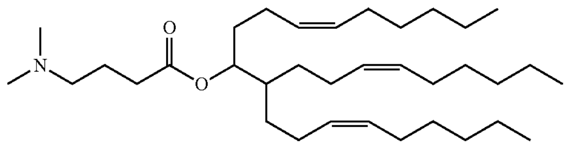

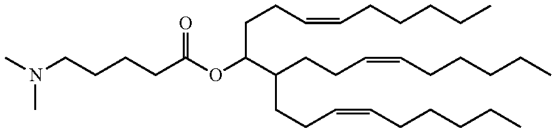

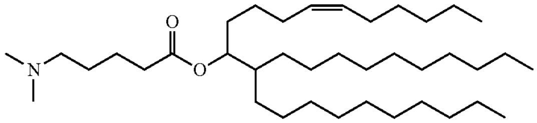

and

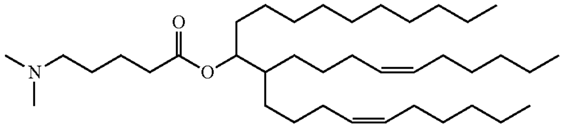

and salts thereof.

Preferred cationic lipid is represented by the following structural formula and described in WO 2016/021683. A compound represented by

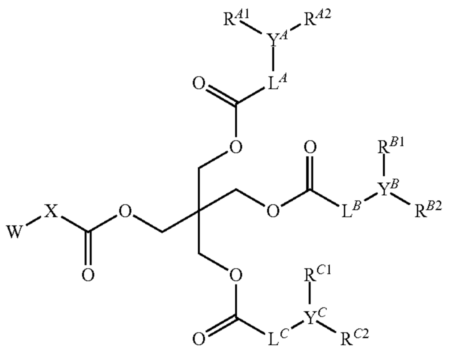

wherein

- W is the formula —$NR^1R^2$ or the formula —$N^+R^3R^4R^5$ $(Z^-)$,
- $R^1$ and $R^2$ are each independently a $C_{1-4}$ alkyl group or a hydrogen atom,
- $R^3$, $R^4$ and $R^5$ are each independently a $C_{1-4}$ alkyl group,
- $Z^-$ is an anion,
- X is an optionally substituted $C_{1-6}$ alkylene group,
- $Y^A$, $Y^B$ and $Y^C$ are each independently an optionally substituted methine group,
- $L^A$, $L^B$ and $L^C$ are each independently an optionally substituted methylene group or a bond, and
- $R^{A1}$, $R^{A2}$, $R^{B1}$, $R^{B2}$, $R^{C1}$ and $R^{C2}$ are each independently an optionally substituted $C_{4-10}$ alkyl group, or a salt thereof.

More preferably, cationic lipids represented by the following structural formulas can be mentioned.

(compound 1)

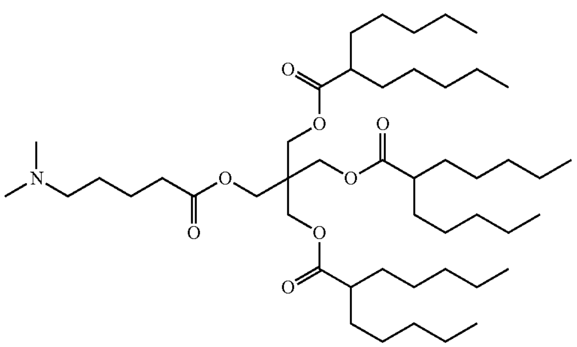

(compound 2)

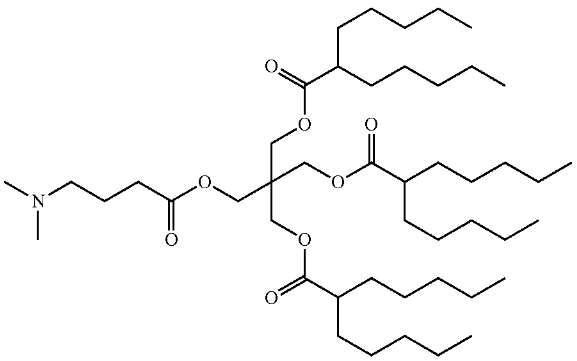

(compound 3)

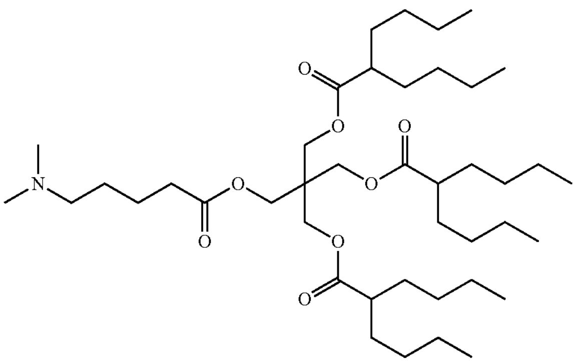

(compound 4)

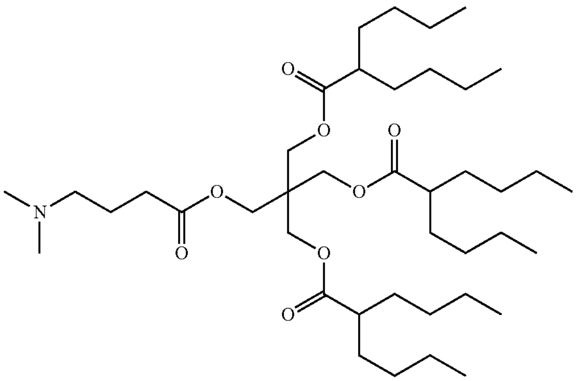

-continued (compound 5)

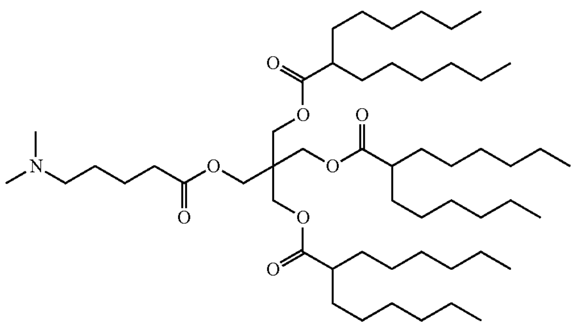

(compound 6)

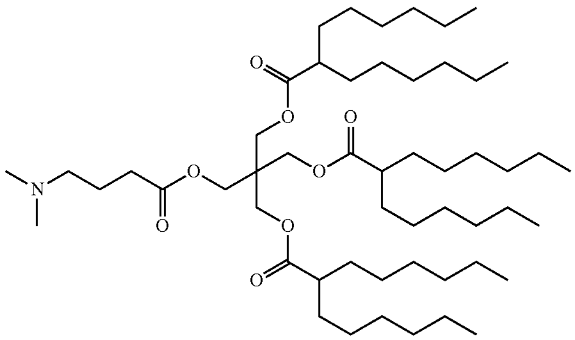

(compound 7)

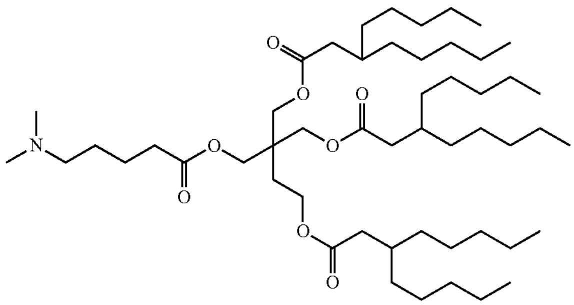

(compound 8)

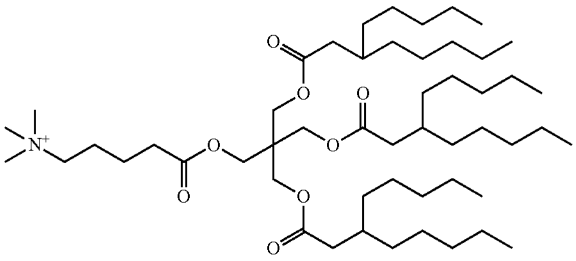

(compound 9)

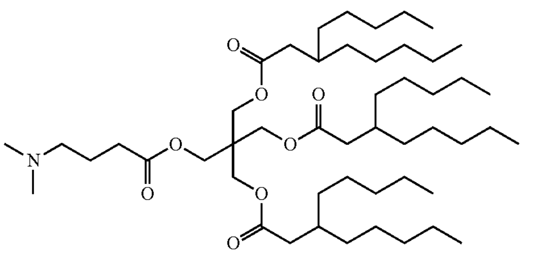

and

-continued (compound 10)

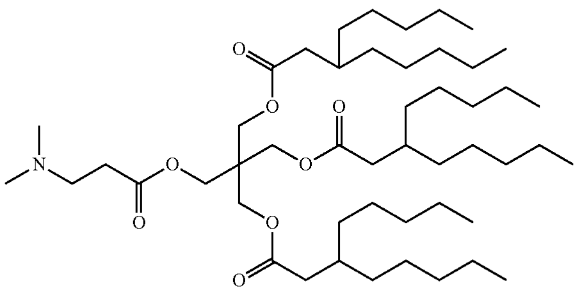

and salts thereof.

Among the above-mentioned cationic lipids, more preferred cationic lipids are represented by the following structural formulas.

(compound 1)

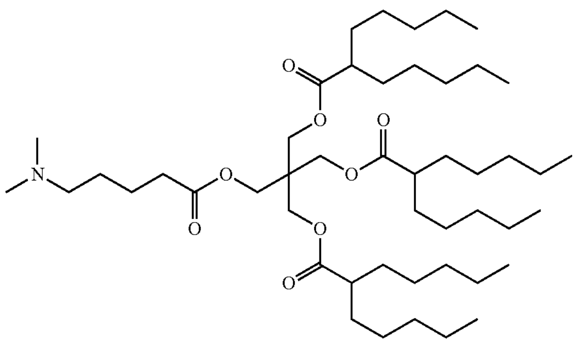

(compound 7)

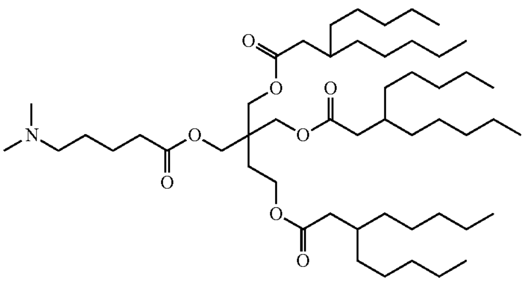

and (compound 8)

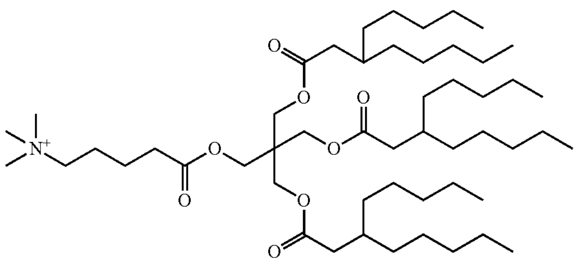

and salts thereof.

In another preferable embodiment, a cationic lipid represented by the following formula (II) (hereinafter to be also referred to as "compound (II)") can be mentioned. A compound represented by (II)
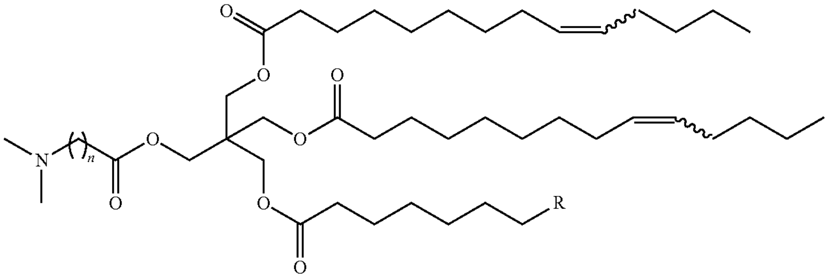
wherein
n is an integer of 2 to 5,
R is a linear $C_{1-5}$ alkyl group, a linear $C_{7-11}$ alkenyl group or a linear $C_{11}$ alkadienyl group, and
wavy lines are each independently shows a cis-type or trans-type bond,
or a salt thereof.
More preferably, cationic lipids represented by the following structural formulas can be mentioned.
(compound 11)
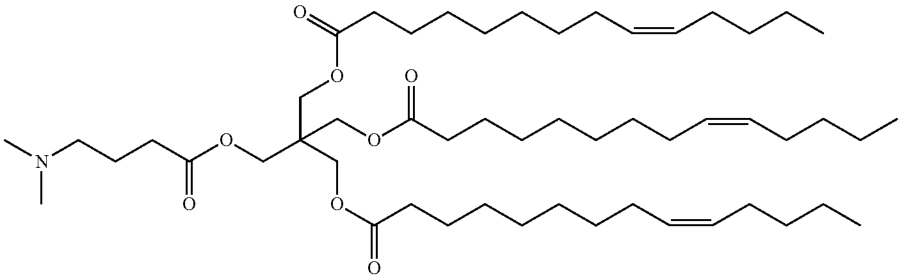
(compound 12)
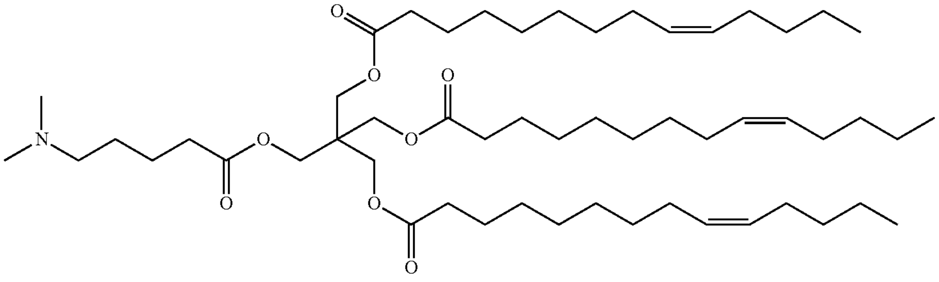
(compound 13)
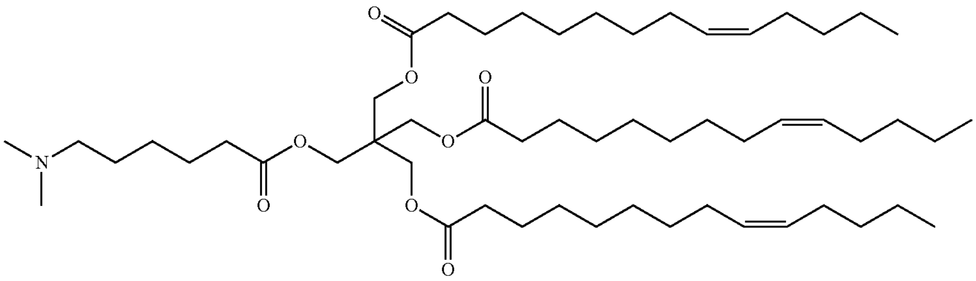

-continued
(compound 14)
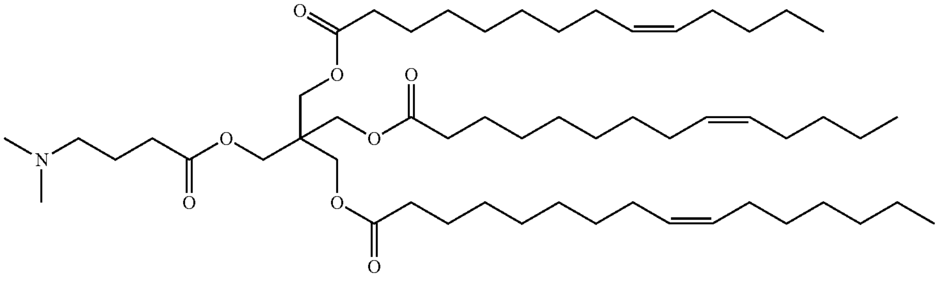
(compound 15)
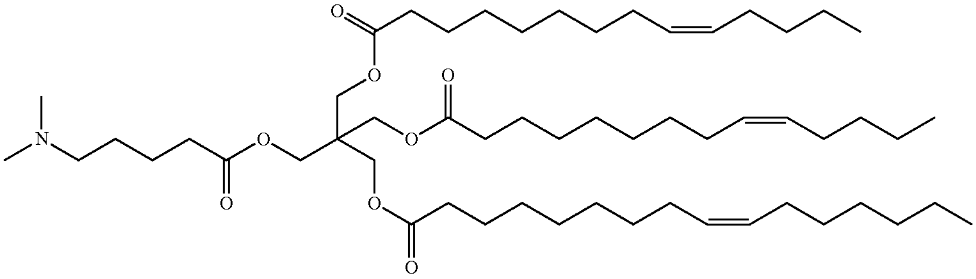
(compound 16)
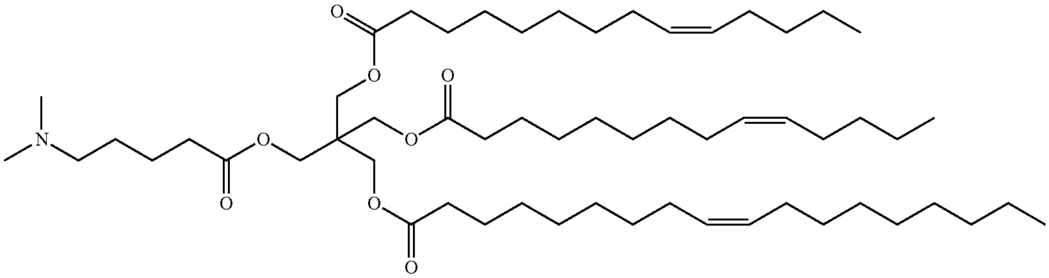
(compound 17)
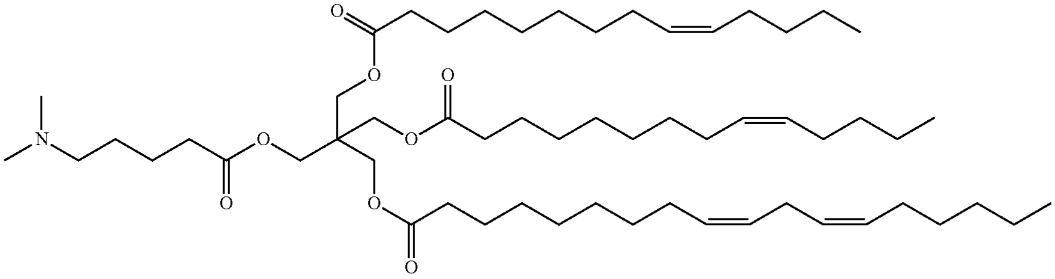
(compound 18)
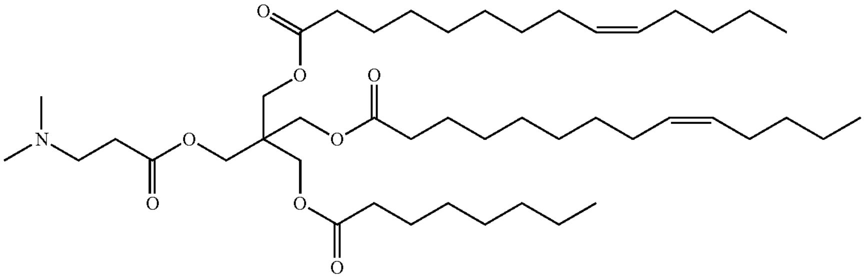

-continued
(compound 19)
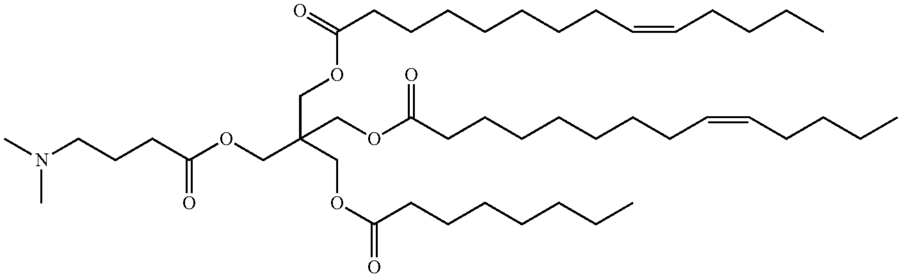
(compound 20)
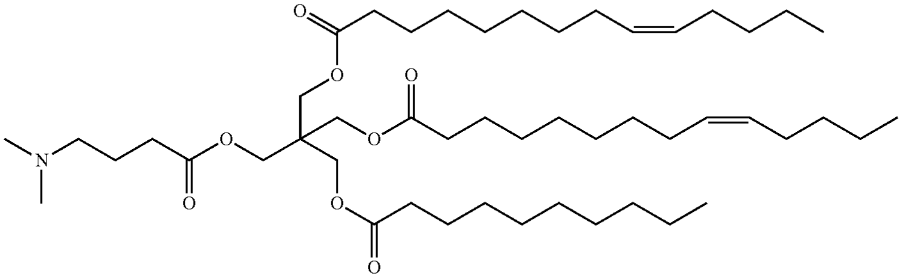
and
(compound 21)
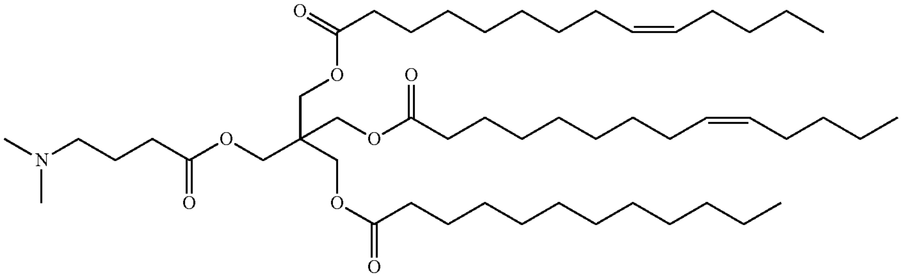
and salts thereof.
Among the above-mentioned cationic lipids, more preferred cationic lipids are represented by the following structural formulas.
(compound 11)
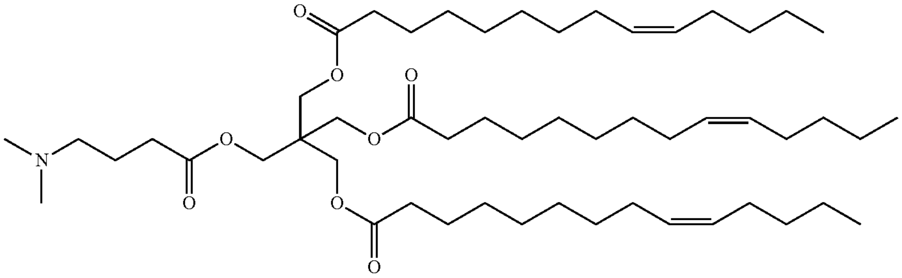
(compound 12)
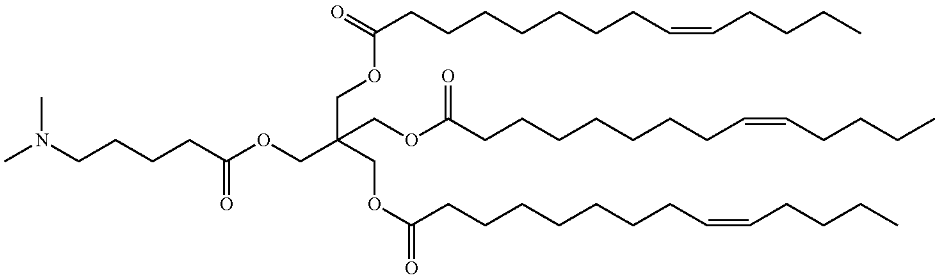
and -continued (compound 21)

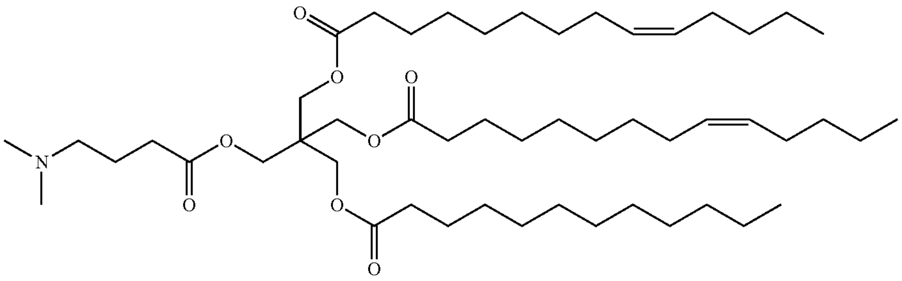

and salts thereof.

The compound (II) can be produced, for example, by the following production method. Among compounds (II), both a compound in which both wavy lines are cis-type bonds and a compound in which one or both of the wavy lines are trans-type bonds can be produced by a production method similar to the one shown below. In particular, compound (II) with a desired structure can be synthesized using appropriate starting materials according to the structure of the desired compound (II) in the esterification process. The salt of compound (II) can be obtained by appropriately mixing with an inorganic base, an organic base, an organic acid, a basic or an acidic amino acid.

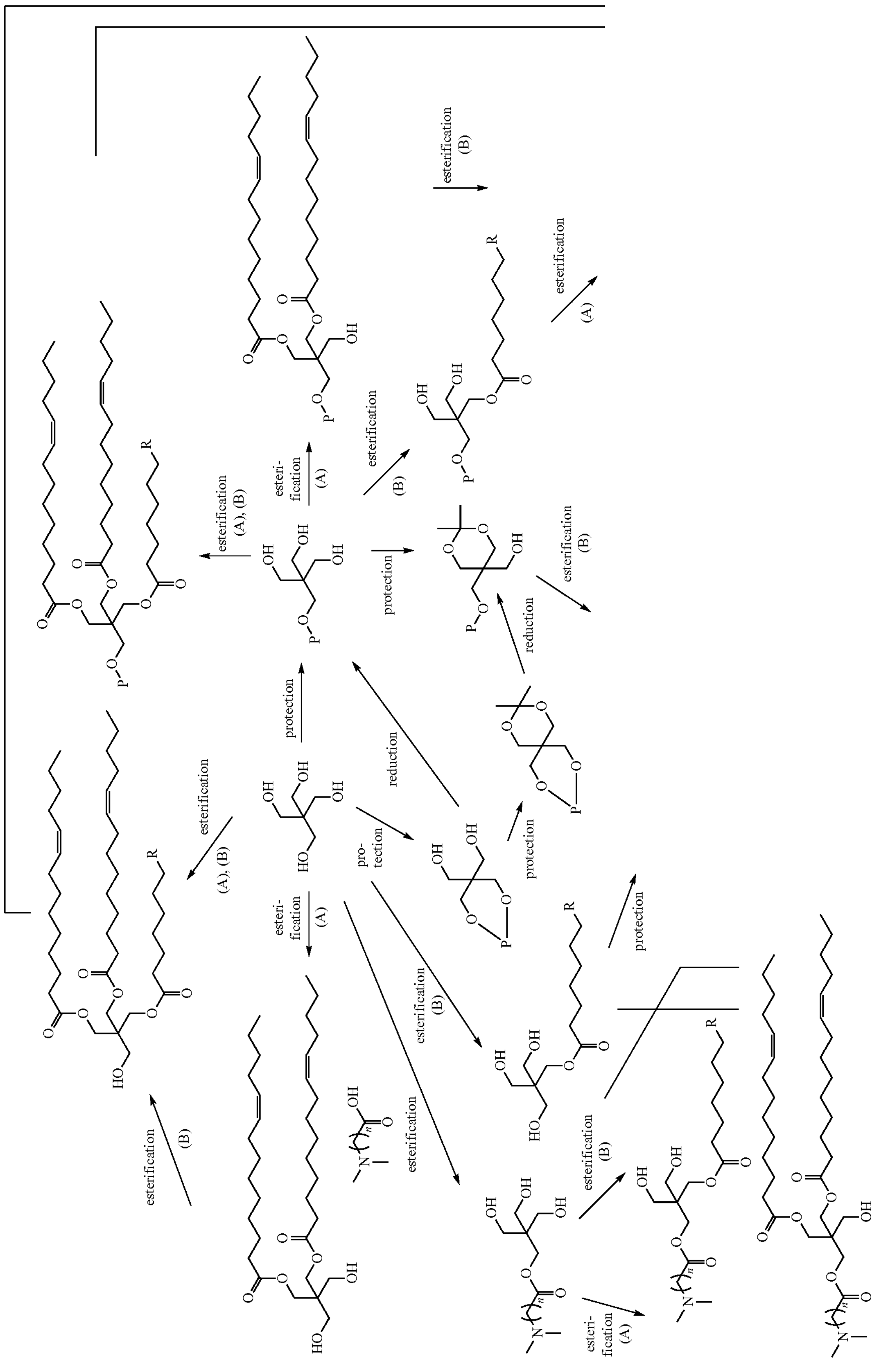
esterification (A), (B)
esterification (A), (B)
esteri-fication (A)
esterification (B)
esterification (B)
esterification (A)
protection
protection
reduction
reduction
pro-tection
esterification (B)
esterification (B)
protection
protection
esteri-fication (A)
esterification
esterification (B)
esterification
esteri-fication (A)

-continued
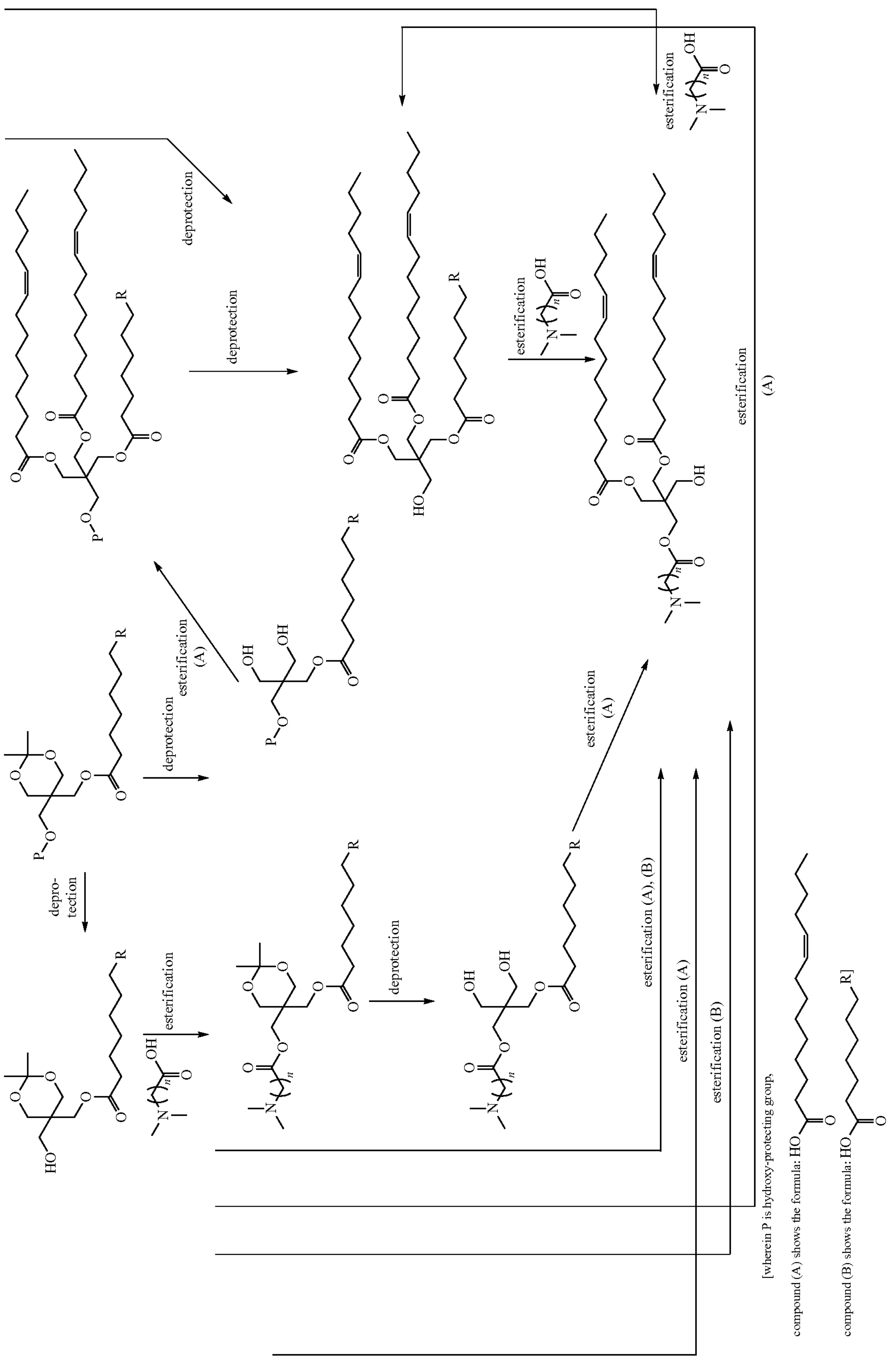

A starting material or a reagent used in each step in the above-mentioned production method, as well as the obtained compound, may each form a salt.

When the compound obtained in each step is a free compound, this compound can be converted to a salt of interest by a method known per se in the art. On the contrary, when the compound obtained in each step is a salt, this salt can be converted to a free form or another type of salt of interest by a method known per se in the art.

The compound obtained in each step may be used in the next reaction directly in the form of its reaction solution or after being obtained as a crude product. Alternatively, the compound obtained in each step can be isolated and/or purified from the reaction mixture by a separation approach such as concentration, crystallization, recrystallization, distillation, solvent extraction, fractionation, or chromatography according to a routine method.

If a starting material or a reagent compound for each step is commercially available, the commercially available product can be used directly.

In the reaction of each step, the reaction time can differ depending on the reagent or the solvent used and is usually 1 min to 48 hr, preferably 10 min to 8 hr, unless otherwise specified.

In the reaction of each step, the reaction temperature can differ depending on the reagent or the solvent used and is usually −78° C. to 300° C., preferably −78° C. to 150° C., unless otherwise specified.

In the reaction of each step, the pressure can differ depending on the reagent or the solvent used and is usually 1 atm to 20 atm, preferably 1 atm to 3 atm, unless otherwise specified.

In the reaction of each step, for example, a microwave synthesis apparatus such as a Biotage Initiator may be used. The reaction temperature can differ depending on the reagent or the solvent used and is usually room temperature to 300° C., preferably room temperature to 250° C., more preferably 50° C. to 250° C., unless otherwise specified. The reaction time can differ depending on the reagent or the solvent used and is usually 1 min to 48 hr, preferably 1 min to 8 hr, unless otherwise specified.

In the reaction of each step, the reagent is used at 0.5 equivalents to 20 equivalents, preferably 0.8 equivalents to 5 equivalents, with respect to the substrate, unless otherwise specified. In the case of using the reagent as a catalyst, the reagent is used at 0.001 equivalents to 1 equivalent, preferably 0.01 equivalents to 0.2 equivalents, with respect to the substrate. When the reagent also serves as a reaction solvent, the reagent is used in the amount of the solvent.

In each step of a reaction, the reaction is carried out without a solvent or by dissolution or suspension in an appropriate solvent, unless otherwise specified. Specific examples of the solvent include the following.

- alcohols: methanol, ethanol, isopropanol, isobutanol, tert-butyl alcohol, 2-methoxyethanol and the like;
- ethers: diethyl ether, diisopropyl ether, diphenyl ether, tetrahydrofuran, 1,2-dimethoxyethane and the like;
- aromatic hydrocarbons: chlorobenzene, toluene, xylene and the like;
- saturated hydrocarbons: cyclohexane, hexane, heptane and the like;
- amides: N,N-dimethylformamide, N-methylpyrrolidone and the like;
- halogenated hydrocarbons: dichloromethane, carbon tetrachloride and the like;
- nitriles: acetonitrile and the like;
- sulfoxide: dimethyl sulfoxide and the like;
- aromatic organic bases: pyridine and the like;
- acid anhydrides: acetic anhydride and the like;
- organic acids: formic acid, acetic acid, trifluoroacetic acid and the like;
- inorganic acids: hydrochloric acid, sulfuric acid and the like;
- esters: ethyl acetate, isopropyl acetate ester and the like;
- ketones: acetone, methylethyl ketone and the like;
- water.

Two or more of these solvents may be used as a mixture at an appropriate ratio.

In each reaction step making use of a base, examples of bases that may be used are those listed below.

- inorganic bases: sodium hydroxide, potassium hydroxide, magnesium hydroxide and the like;
- basic salts: sodium carbonate, calcium carbonate, sodium hydrogen carbonate and the like;
- organic bases: triethylamine, diethylamine, pyridine, 4-dimethylaminopyridine, N,N-dimethylaniline, 1,4-diazabicyclo [2.2.2]octane, 1,8-diazabicyclo [5.4.0]-7-undecene, imidazole, piperidine and the like;
- metal alkoxides: sodium ethoxide, potassium tert-butoxide, sodium tert-butoxide and the like;
- alkali metal hydrides: sodium hydride and the like;
- metal amides: sodium amide, lithium diisopropylamide, lithium hexamethyldisilazide and the like;
- organic lithiums: n-butyllithium, sec-butyllithium and the like.

In each reaction step making use of an acid or acid catalyst, the following acids or acid catalysts are used.

- inorganic acids: hydrochloric acid, sulfuric acid, nitric acid, hydrobromic acid, phosphoric acid and the like;
- organic acids: acetic acid, trifluoroacetic acid, citric acid, p-toluenesulfonic acid, 10-camphor sulfonic acid and the like;
- Lewis acid: boron trifluoride diethyl ether complex, zinc iodide, anhydrous aluminum chloride, anhydrous zinc chloride, anhydrous iron chloride and the like.

Unless stated otherwise, each reaction step may be carried out according to a standard method known per se in the art, such as those described in Jikken Kagaku Koza (Encyclopedia of Experimental Chemistry in English), 5th Ed., Vol. 13 to Vol. 19 (edited by the Chemical Society of Japan); Shin Jikken Kagaku Koza (New Encyclopedia of Experimental Chemistry in English), Vol. 14 to Vol. 15 (edited by the Chemical Society of Japan); Fine Organic Chemistry, 2nd Ed. Revised (L. F. Tietze, Th. Eicher, Nankodo); Organic Name Reactions; The Reaction Mechanism and Essence, Revised (Hideo Togo, Kodansha); Organic Syntheses Collective Volume I-VII (John Wiley & Sons, Inc.); Modern Organic Synthesis in the Laboratory: A Collection of Standard Experimental Procedures (Jie Jack Li, Oxford University Press); Comprehensive Heterocyclic Chemistry III, Vol. 1 to Vol. 14 (Elsevier Japan KK); Strategic Applications of Named Reactions in Organic Synthesis (translated by Kiyoshi Tomioka, Kagaku-Dojin Publishing); Comprehensive Organic Transformations (VCH Publishers, Inc.), 1989; etc.

In each step, the protection or deprotection reaction of a functional group may be carried out according to a method known per se in the art, for example, a method described in "Protective Groups in Organic Synthesis, 4th Ed." (Theodora W. Greene, Peter G. M. Wuts), Wiley-Interscience, 2007; "Protecting Groups, 3rd Ed." (P. J. Kocienski) Thieme, 2004); etc.

Examples of a protective group for a hydroxy group or a phenolic hydroxy group in alcohols or the like include:

ether-type protective groups such as methoxymethyl ether, benzyl ether, p-methoxybenzyl ether, t-butyldimethylsilyl ether, t-butyldiphenylsilyl ether, and tetrahydropyranyl ether; carboxylic acid ester-type protective groups such as acetic acid ester; sulfonic acid ester-type protective groups such as methanesulfonic acid ester; and carbonic acid ester-type protective groups such as t-butyl carbonate.

Examples of a protective group for a carbonyl group in aldehydes include: acetal-type protective groups such as dimethylacetal; and cyclic acetal-type protective groups such as cyclic 1,3-dioxane.

Examples of a protective group for a carbonyl group in ketones include: ketal-type protective groups such as dimethylketal; cyclic ketal-type protective groups such as cyclic 1,3-dioxane; oxime-type protective groups such as O-methyloxime; and hydrazone-type protective groups such as N,N-dimethylhydrazone.

Examples of a protective group for a carboxyl group include: ester-type protective groups such as methyl ester; and amide-type protective groups such as N,N-dimethylamide.

Examples of a protective group for thiol include: ether-type protective groups such as benzyl thioether; and ester-type protective groups such as thioacetic acid ester, thiocarbonate and thiocarbamate.

Examples of a protective group for an amino group or aromatic heterocycle such as imidazole, pyrrole or indole include: carbamate-type protective groups such as benzyl carbamate; amide-type protective groups such as acetamide; alkylamine-type protective groups such as N-triphenylmethylamine; and sulfonamide-type protective groups such as methanesulfonamide.

The protective groups can be removed by use of a method known per se in the art, for example, a method using an acid, a base, ultraviolet light, hydrazine, phenylhydrazine, sodium N-methyldithiocarbamate, tetrabutylammonium fluoride, palladium acetate or trialkylsilyl halide (for example, trimethylsilyl iodide or trimethylsilyl bromide), or a reduction method.

In each step making use of a reduction reaction, examples of reducing agents that may be used include: metal hydrides such as lithium aluminum hydride, sodium triacetoxyborohydride, sodium cyanoborohydride, diisobutyl aluminum hydride (DIBAL-H), sodium borohydride and tetramethylammonium triacetoxyborohydride; boranes such as borane-tetrahydrofuran complex; Raney nickel; Raney cobalt; hydrogen; and formic acid. For example, Raney-nickel or Raney cobalt can be used in the presence of hydrogen or formic acid. In the case of reducing a carbon-carbon double bond or triple bond, a method using a catalyst such as palladium-carbon or Lindlar's catalyst may be used.

In each step making use of an oxidation reaction, examples of oxidizing agents that may be used include: peracids such as m-chloroperbenzoic acid (MCPBA), hydrogen peroxide and t-butyl hydroperoxide; perchlorates such as tetrabutylammonium perchlorate; chlorates such as sodium chlorate; chlorites such as sodium chlorite; periodates such as sodium periodate; high-valent iodine reagents such as iodosylbenzene; manganese reagents, such as manganese dioxide and potassium permanganate; lead reagents such as lead tetraacetate; chromium reagents, such as pyridinium chlorochromate (PCC), pyridinium dichromate (PDC) and Jones' reagent; halogen compounds such as N-bromosuccinimide (NBS); oxygen; ozone; sulfur trioxide-pyridine complex; osmium tetroxide; selenium dioxide; and 2,3-dichloro-5,6-dicyano-1,4-benzoquinone (DDQ).

In each step making use of a radical cyclization reaction, examples of radical initiators that may be used include: azo compounds such as azobisisobutyronitrile (AIBN); water-soluble radical initiators such as 4-4'-azobis-4-cyanopentanoic acid (ACPA); triethylboron in the presence of air or oxygen; and benzoyl peroxide. Examples of radical initiators to be used include tributylstannane, tristrimethylsilylsilane, 1,1,2,2-tetraphenyldisilane, diphenylsilane and samarium iodide.

In each step making use of a Wittig reaction, examples of Wittig reagents that may be used include alkylidenephosphoranes. The alkylidenephosphoranes can be prepared by a method known per se in the art, for example, the reaction between a phosphonium salt and a strong base.

In each step making use of a Horner-Emmons reaction, examples of reagents that may be used include phosphonoacetic acid esters such as methyl dimethylphosphonoacetate and ethyl diethylphosphonoacetate, and bases such as alkali metal hydrides and organic lithiums.

In each step making use of a Friedel-Crafts reaction, examples of reagents that may be used include a Lewis acid and an acid chloride or alkylating agent (e.g. alkyl halides, alcohols and olefins). Alternatively, an organic or inorganic acid may be used instead of the Lewis acid, and acid anhydrides such as acetic anhydride may be used instead of the acid chloride.

In each step making use of an aromatic nucleophilic substitution reaction, a nucleophile (e.g., amine or imidazole) and a base (e.g., basic salt or organic base) may be used as reagents.

In each step making use of a nucleophilic addition reaction using a carbanion, nucleophilic 1,4-addition reaction (Michael addition reaction) using a carbanion, or nucleophilic substitution reaction using a carbanion, examples of bases that may be used for generating the carbanion include organolithium reagents, metal alkoxides, inorganic bases and organic bases.

In each step making use of a Grignard reaction, examples of Grignard reagents that may be used include aryl magnesium halides such as phenyl magnesium bromide, and alkyl magnesium halides such as methyl magnesium bromide, isopropylmagnesium bromide. The Grignard reagent can be prepared by a method known per se in the art, for example, the reaction between an alkyl halide or aryl halide and magnesium metal in ether or tetrahydrofuran as a solvent.

In each step making use of a Knoevenagel condensation reaction, an active methylene compound flanked by two electron-attracting groups (e.g., malonic acid, diethyl malonate or malononitrile) and a base (e.g., organic bases, metal alkoxides or inorganic bases) may be used as reagents.

In each step making use of a Vilsmeier-Haack reaction, phosphoryl chloride and an amide derivative (e.g. N,N-dimethylformamide) may be used as reagents.

In each step making use of an azidation reaction of alcohols, alkyl halides or sulfonic acid esters, examples of azidating agents that may be used include diphenylphosphorylazide (DPPA), trimethylsilylazide and sodium azide. In the case of azidating, for example, alcohols, a method using diphenylphosphorylazide and 1,8-diazabicyclo[5,4,0]undec-7-ene (DBU), a method using trimethylsilylazide and Lewis acid, or the like can be used.

In each step making use of a reductive amination reaction, examples of reducing agents that may be used include sodium triacetoxyborohydride, sodium cyanoborohydride, hydrogen and formic acid. When the substrate is an amine compound, examples of carbonyl compounds that may be used include p-formaldehyde as well as aldehydes such as acetaldehyde and ketones such as cyclohexanone. When the substrate is a carbonyl compound, examples of amines that may be used include primary amines such as ammonia and methylamine, and secondary amines such as dimethylamine.

In each step making use of a Mitsunobu reaction, azodicarboxylic acid esters (e.g. diethyl azodicarboxylate (DEAD) and diisopropyl azodicarboxylate (DIAD)) and triphenylphosphine may be used as reagents.

In each step making use of an esterification, amidation or ureation reaction, examples of reagents that may be used include acyl halides such as acid chlorides or acid bromides, and activated carboxylic acids such as acid anhydrides, active esters or sulfate esters. Examples of the activating agents for carboxylic acids include: carbodiimide condensing agents such as 1-ethyl-3-(3-dimethylaminopropyl)carbodiimide hydrochloride (WSCD); triazine condensing agents such as 4-(4,6-dimethoxy-1,3,5-triazin-2-yl)-4-methylmorpholinium chloride-n-hydrate (DMT-MM); carbonic acid ester condensing agents such as 1,1-carbonyldiimidazole (CDI); diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformate such as ethyl chloroformate; O-(7-azabenzotriazol-1-yl)-N,N,N',N'-tetramethyluronium hexafluorophosphate (HATU); sulfuric acid; and combinations thereof. In the case of using a carbodiimide condensing agent, the addition of an additive such as 1-hydroxybenzotriazole (HOBt), N-hydroxysuccinimide (HOSu) or dimethylaminopyridine (DMAP) to the reaction may be beneficial.

In each step making use of a coupling reaction, examples of metal catalysts that may be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and palladium(II) acetate; nickel compounds such as tetrakis(triphenylphosphine)nickel(0); rhodium compounds such as tris(triphenylphosphine)rhodium(III) chloride; cobalt compounds; copper compounds such as copper oxide and copper (I) iodide; and platinum compounds. Addition of a base to the reaction may also be beneficial. Examples of such bases include inorganic bases and basic salts.

In each step making use of a thiocarbonylation reaction, diphosphorus pentasulfide is typically used as a thiocarbonylating agent. A reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) may be used instead of diphosphorus pentasulfide.

In each step making use of a Wohl-Ziegler reaction, examples of halogenating agents that may be used include N-iodosuccinimide, N-bromosuccinimide (NBS), N-chlorosuccinimide (NCS), bromine and sulfuryl chloride. The reaction can be accelerated by the further addition of a radical initiator such as heat, light, benzoyl peroxide or azobisisobutyronitrile.

In each step making use of a halogenation reaction of a hydroxy group, examples of halogenating agents that may be used include a hydrohalic acid or the acid halide of an inorganic acid; examples include hydrochloric acid, thionyl chloride, and phosphorus oxychloride for chlorination and 48% hydrobromic acid for bromination. In addition, a method for obtaining an alkyl halide from an alcohol by the action of triphenylphosphine and carbon tetrachloride or carbon tetrabromide, etc., may also be used. Alternatively, a method for synthesizing an alkyl halide through a 2-step reaction involving the conversion of an alcohol to a sulfonic acid ester and subsequent reaction with lithium bromide, lithium chloride or sodium iodide may also be used.

In each step making use of an Arbuzov reaction, examples of reagents that may be used include alkyl halides such as bromoethyl acetate, and phosphites such as triethylphosphite and tri(isopropyl)phosphite.

In each step making use of a sulfone-esterification reaction, examples of the sulfonylating agent used include methanesulfonyl chloride, p-toluenesulfonyl chloride, methanesulfonic anhydride and p-toluenesulfonic anhydride and trifluoromethanesulfonic anhydride.

In each step making use of a hydrolysis reaction, an acid or a base may be used as a reagent. In the case of carrying out the acid hydrolysis reaction of a t-butyl ester, reagents such as formic acid, triethylsilane or the like may be added to reductively trap the by-product t-butyl cation.

In each step making use of a dehydration reaction, examples of dehydrating agents that may be used include sulfuric acid, diphosphorus pentaoxide, phosphorus oxychloride, N,N'-dicyclohexylcarbodiimide, alumina and polyphosphoric acid.

In another preferable embodiment, a cationic lipid represented by the following formula (III) (hereinafter to be also referred to as "compound (III)") can be mentioned. A compound represented by

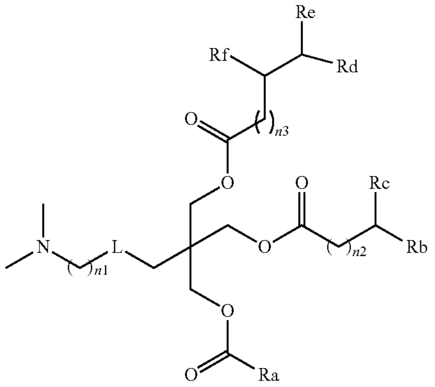

(III)

wherein n1 is an integer of 2 to 6, n2 is an integer of 0 to 2, n3 is an integer of 0 to 2, L is —C(O)O— or —NHC(O)O—, Ra is a linear $C_{5-13}$ alkyl group, a linear $C_{13-17}$ alkenyl group or a linear $C_{17}$ alkadienyl group, Rb is a linear $C_{2-9}$ alkyl group, Rc is a hydrogen atom or a linear $C_{2-9}$ alkyl group, Rd is a hydrogen atom or a linear $C_{2-9}$ alkyl group, Re is a linear $C_{2-9}$ alkyl group, and Rf is a linear $C_{2-9}$ alkyl group, or a salt thereof.

more preferably, the following structural formula represented by cationic lipid can be mentioned.

(compound 22)
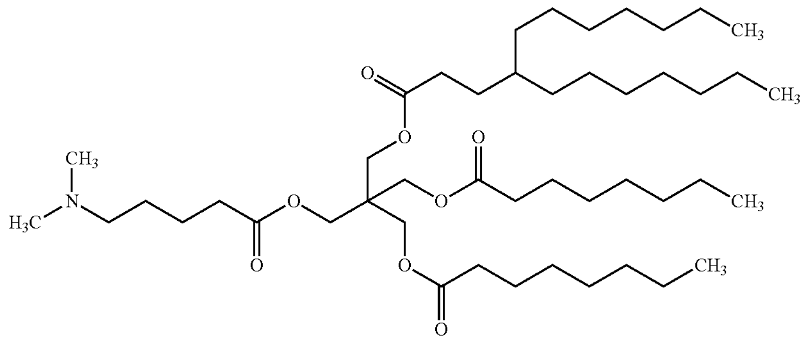
(compound 23)
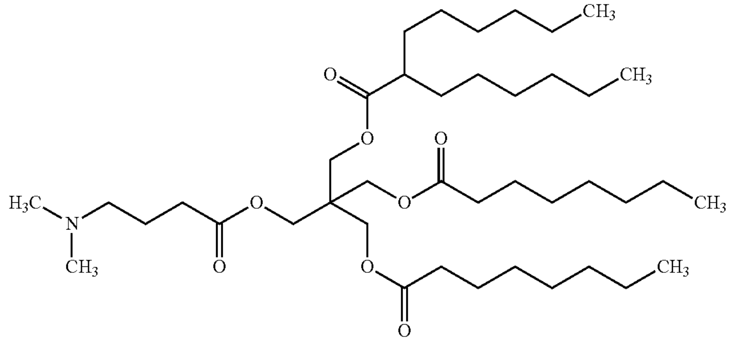
(compound 24)
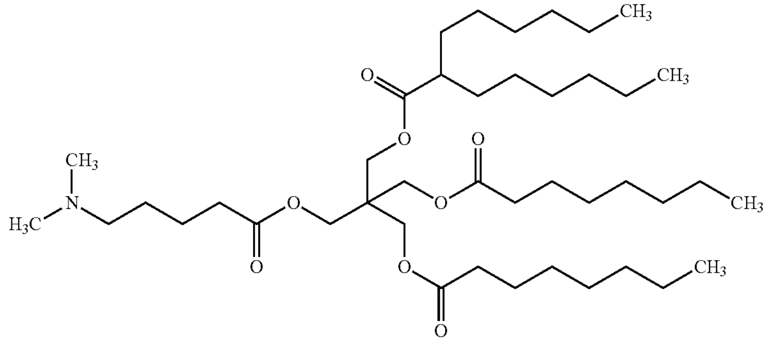
(compound 25)
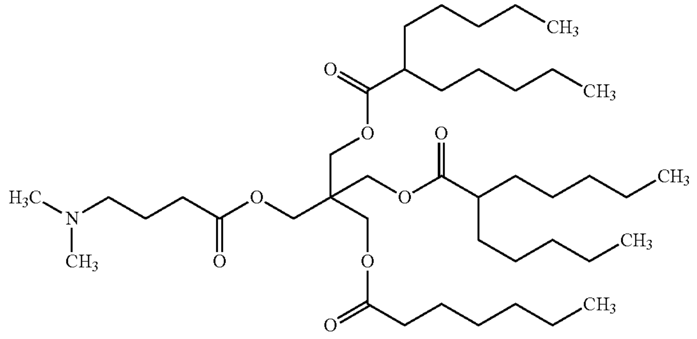

-continued
(compound 26)
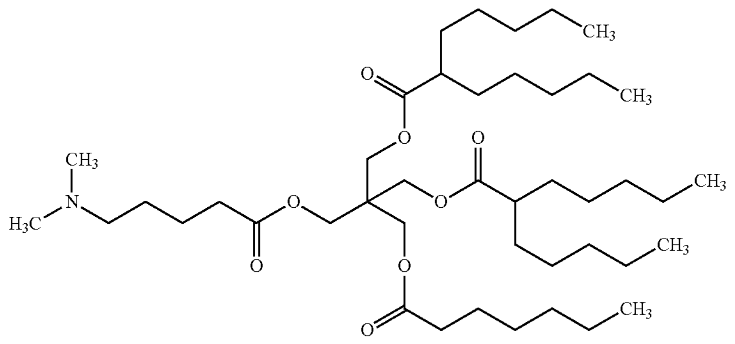
(compound 27)
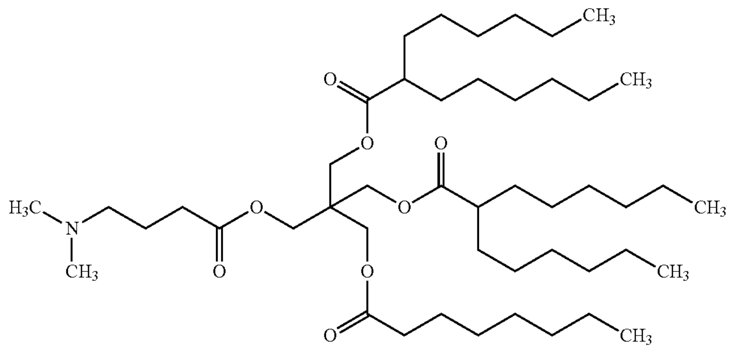
(compound 28)
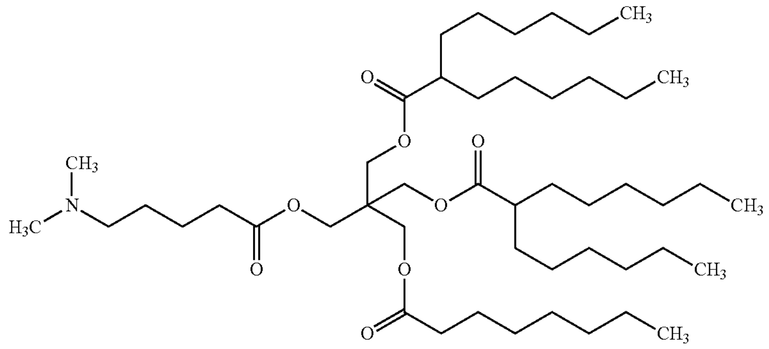
(compound 29)
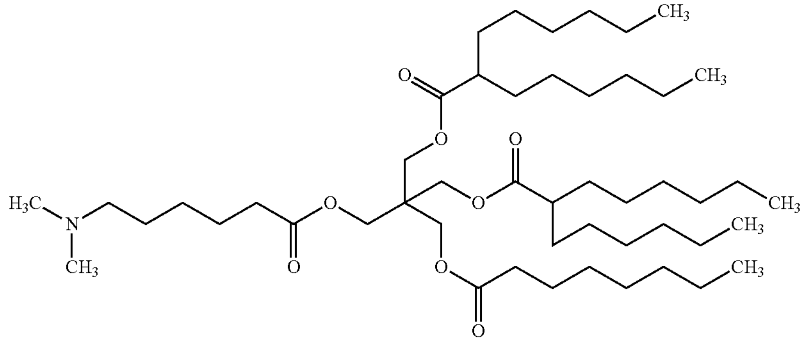

-continued
(compound 30)
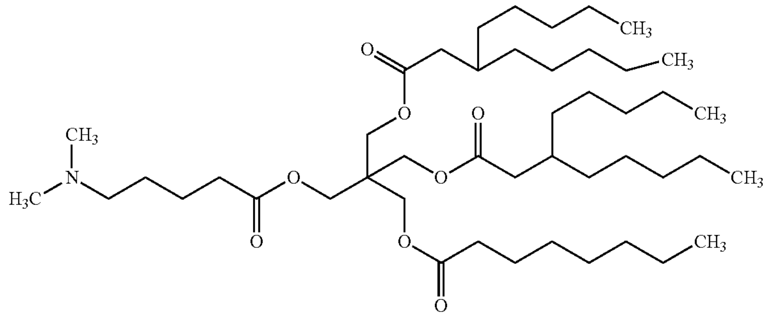
(compound 31)
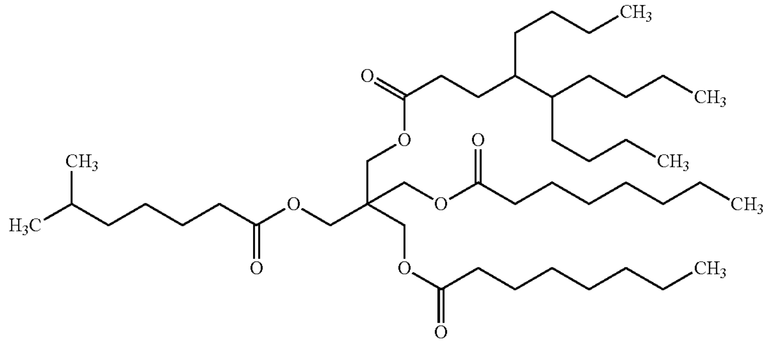
(compound 32)
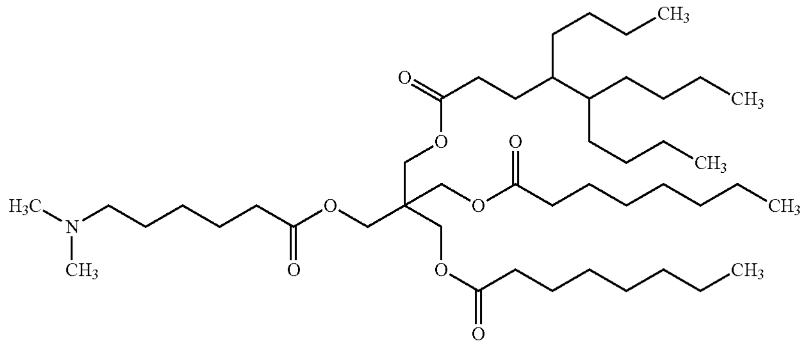
(compound 33)
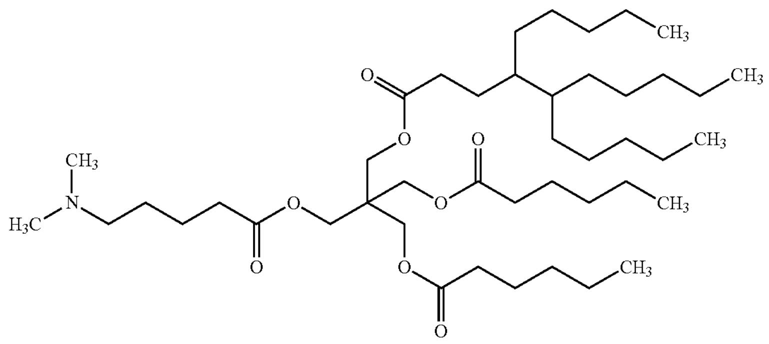

-continued
(compound 34)
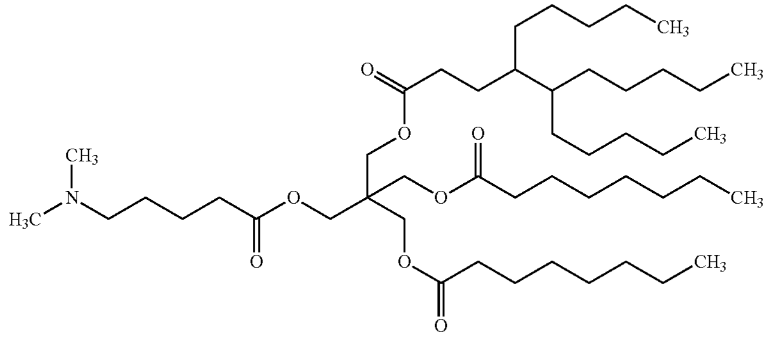
(compound 35)
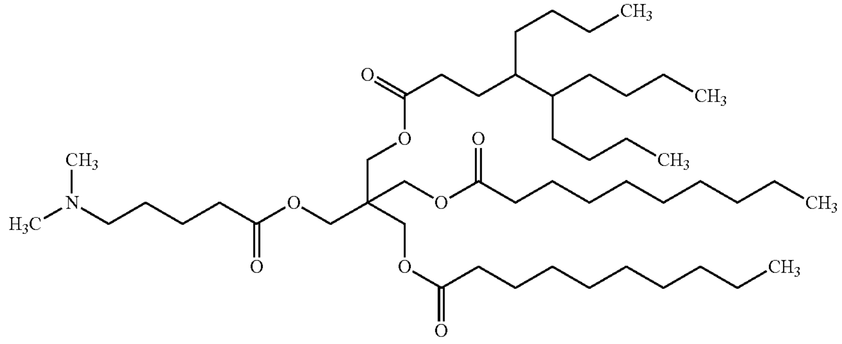
(compound 36)
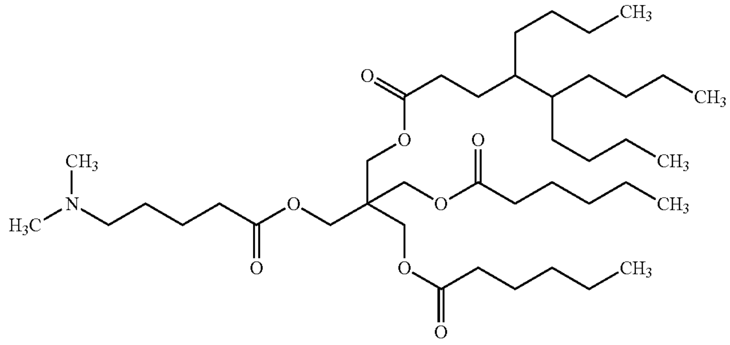
(compound 37)
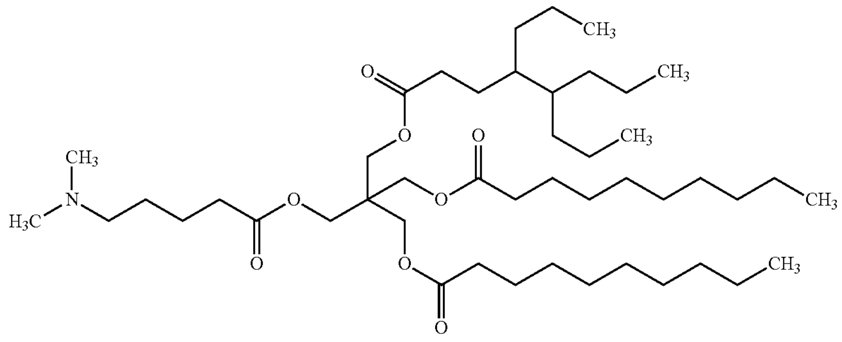

-continued
(compound 38)
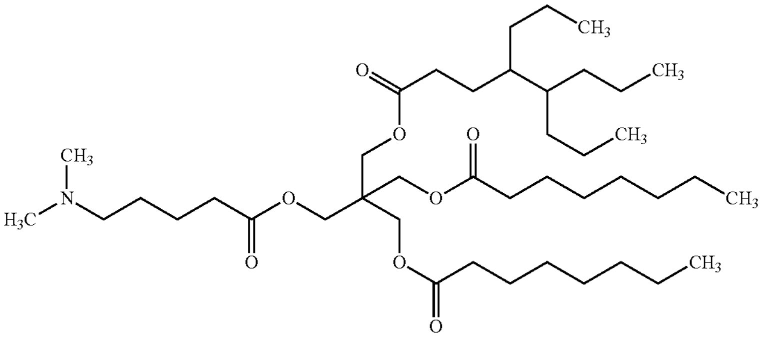
and
(compound 39)
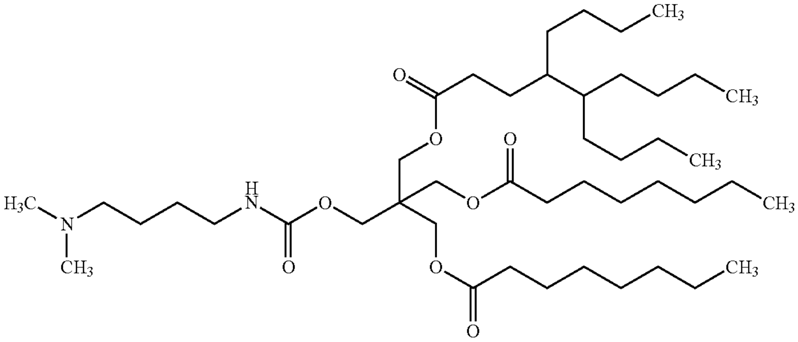
and salts thereof.
Among the above-mentioned cationic lipids, a cationic lipid represented by the following structural formula is more preferable.
(compound 31)
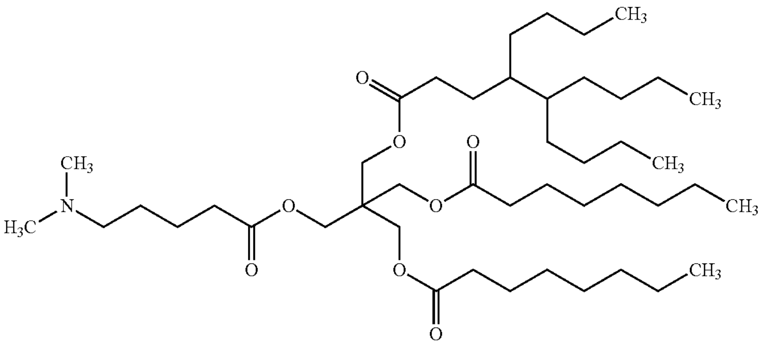
and -continued (compound 35)

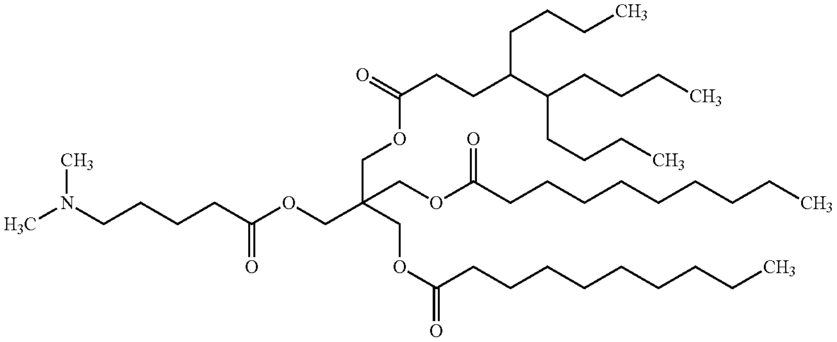

and salts thereof.

The compound (III) can be manufactured, for example, by the following production methods. Particularly, compound (I) with the desired structure can be synthesized using appropriate starting materials according to the structure of the desired compound (III) in the esterification process. The salt of compound (III) can be obtained by appropriate mixing with an inorganic base, an organic base, an organic acid, a basic or an acidic amino acid.

Production method A
(L is —C(O)O—)
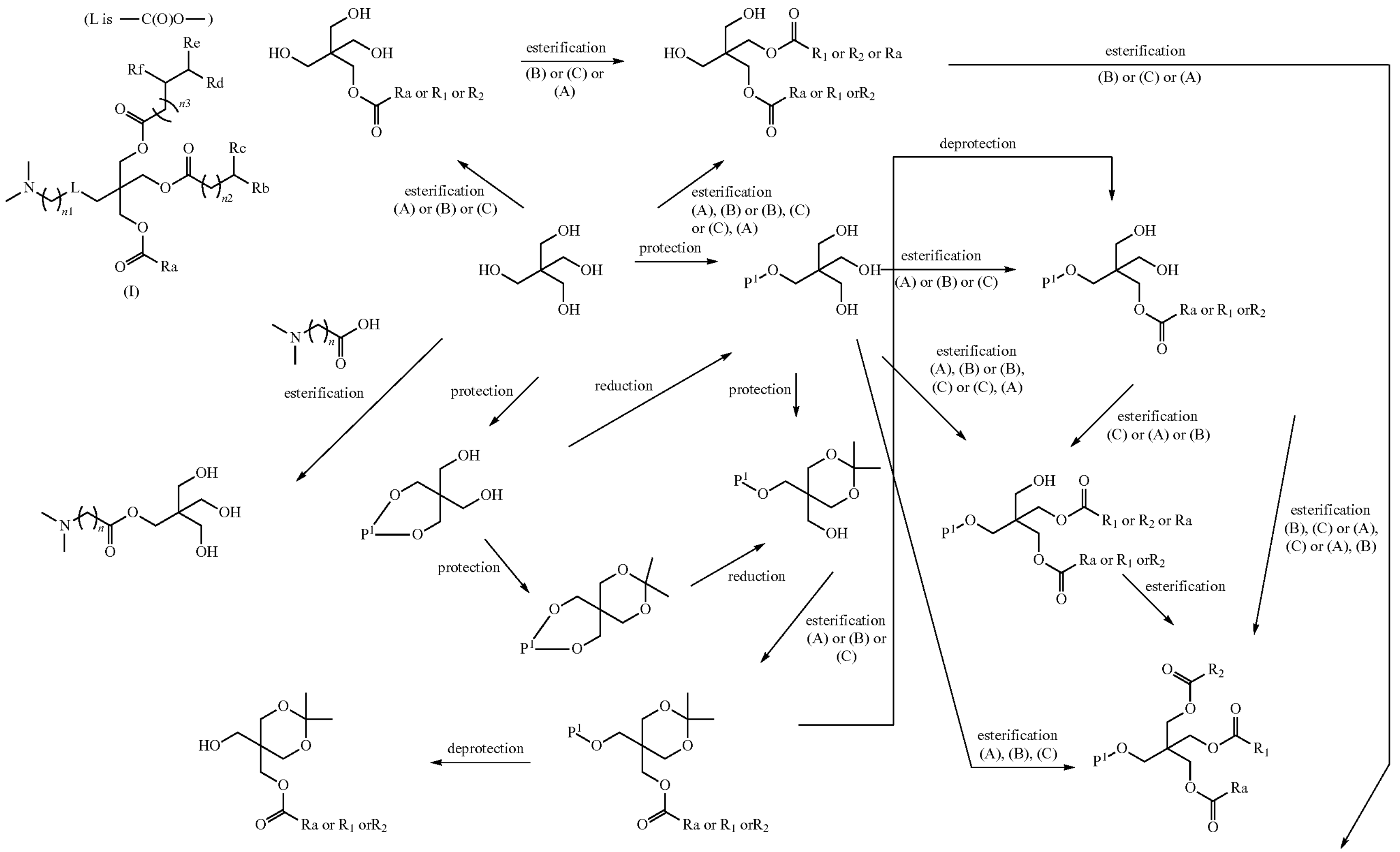
(I)

-continued
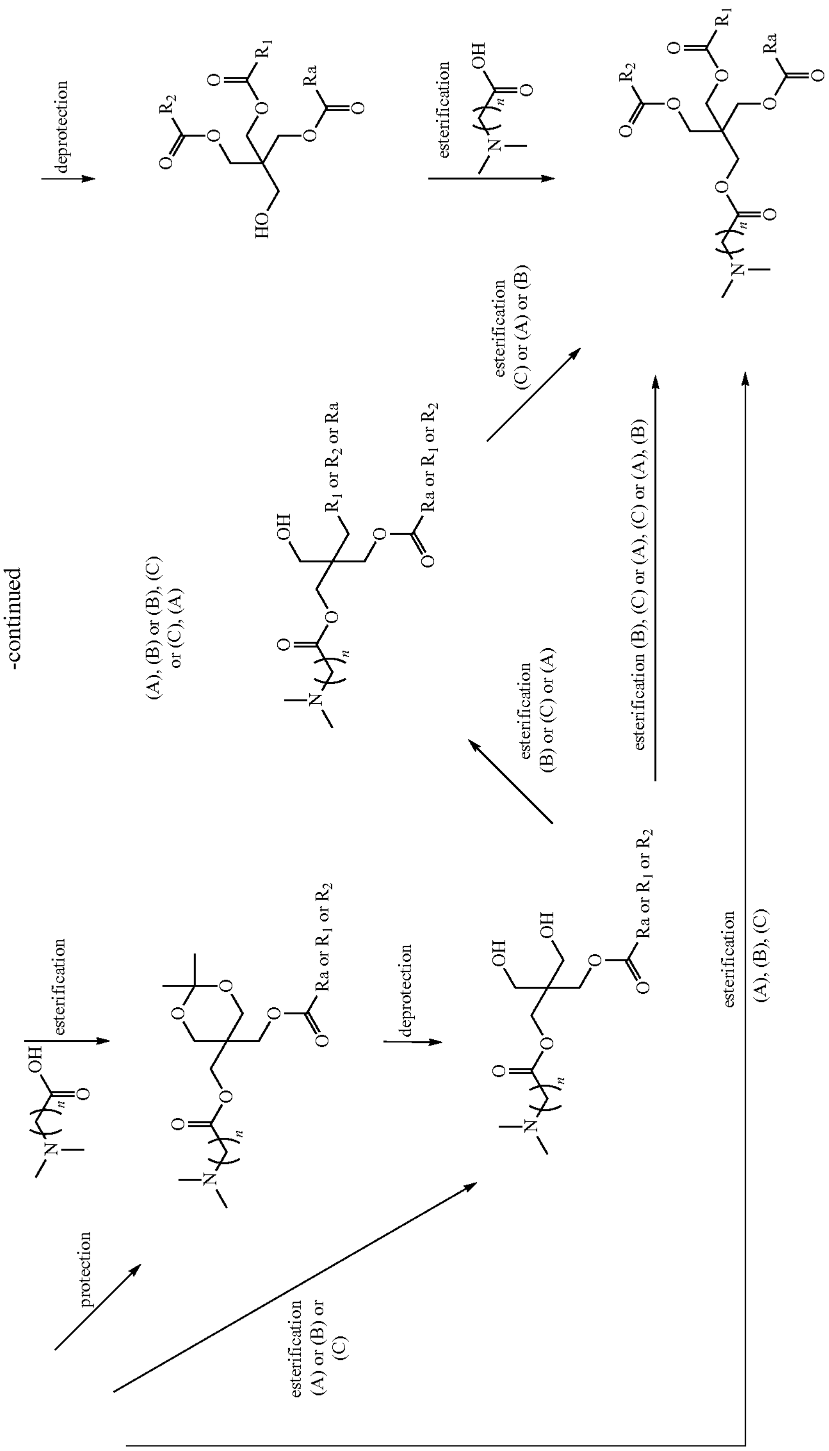

Production Method B (L is —NHC(O)O—)
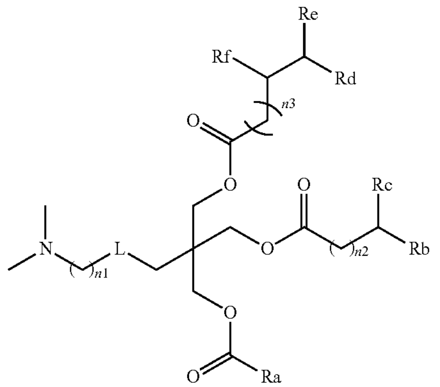
(I)
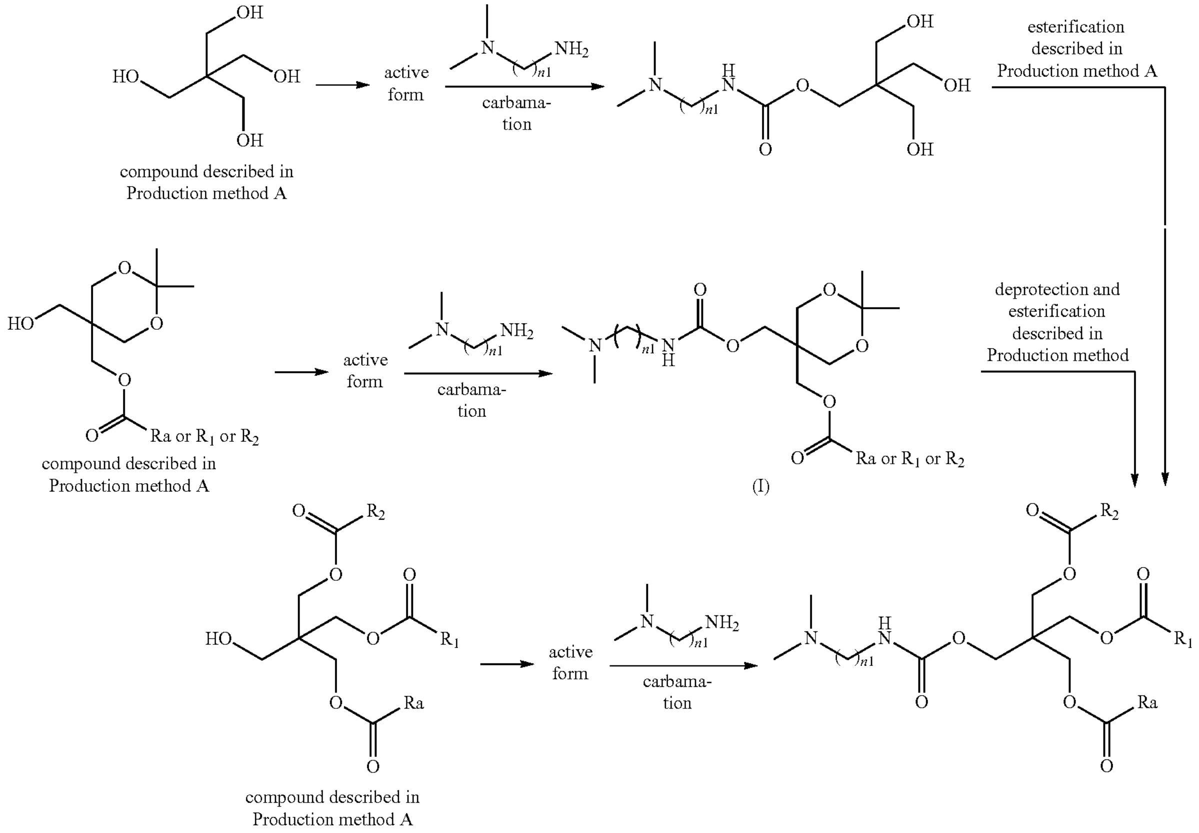

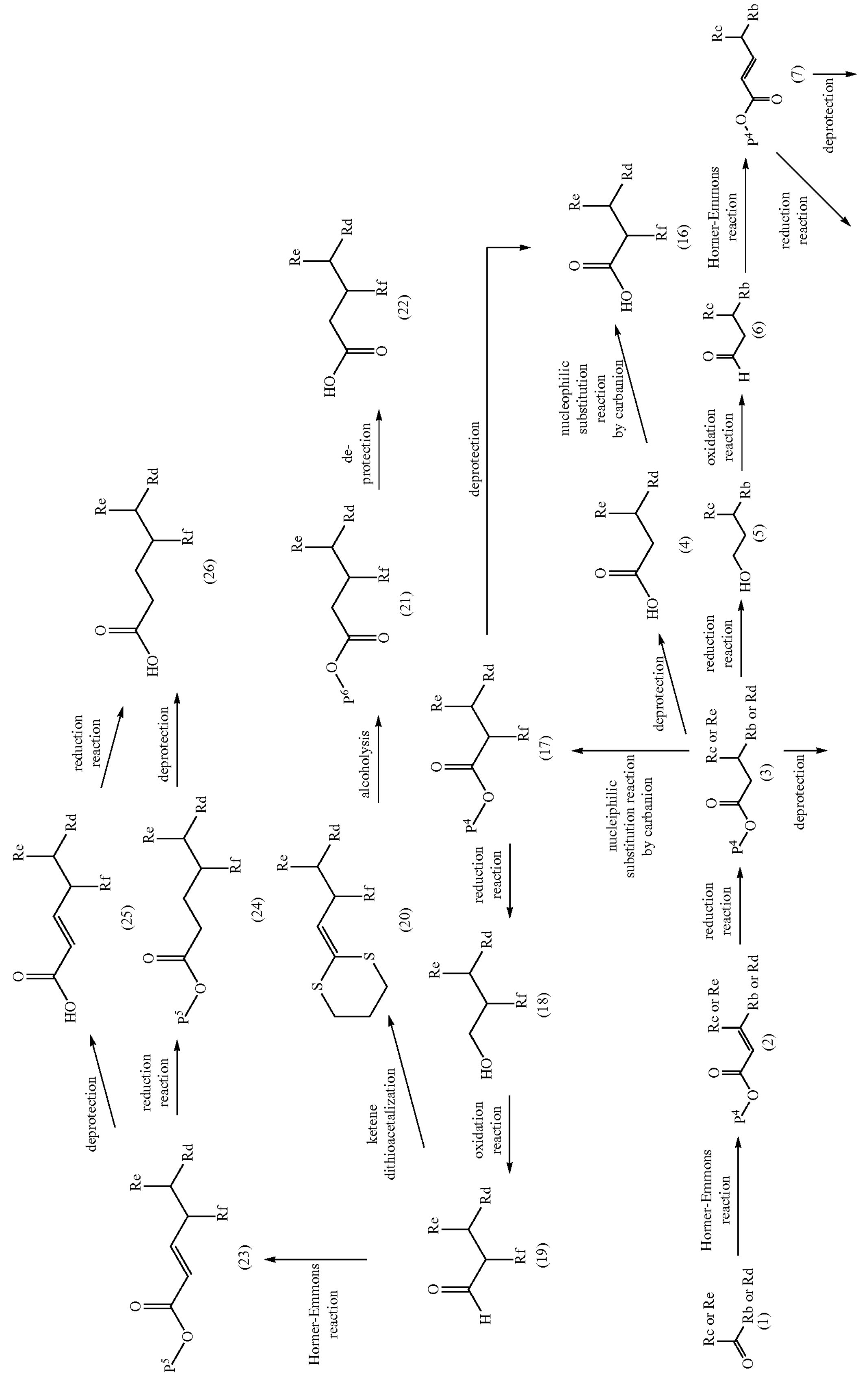
(1)
Horner-Emmons reaction
(2)
reduction reaction
(3)
deprotection
reduction reaction
(5)
oxidation reaction
(6)
Horner-Emmons reaction
(7)
deprotection
reduction reaction
deprotection
(4)
nucleiphilic substitution reaction by carbanion
(16)
nucleiphilic substitution reaction by carbanion
(17)
deprotection
reduction reaction
(18)
oxidation reaction
(19)
Horner-Emmons reaction
(23)
deprotection
(25)
reduction reaction
reduction reaction
(24)
deprotection
(26)
ketene dithioacetalization
(20)
alcoholysis
(21)
de-protection
(22)

-continued
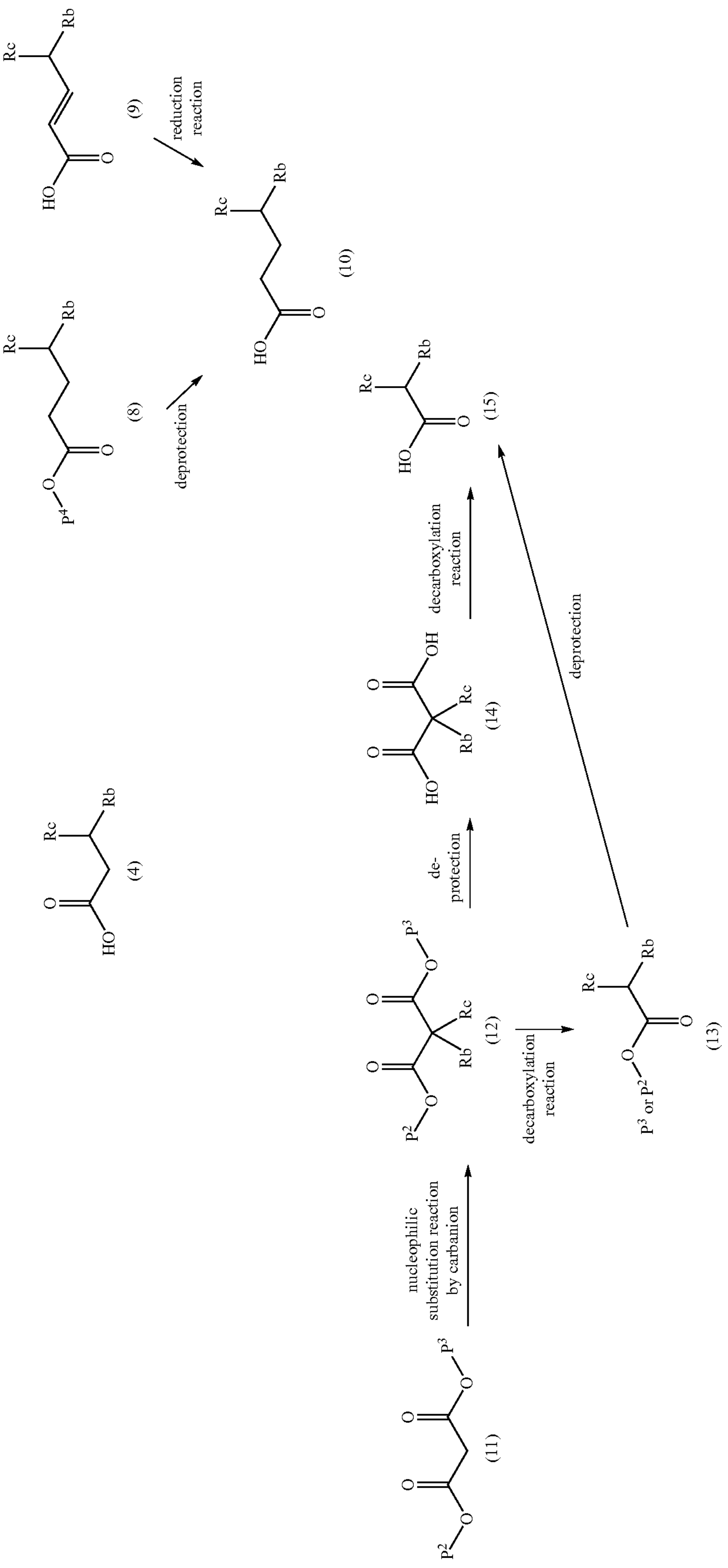

in the above formulas, $P^1$, $P^2$, $P^3$, $P^4$, $P^5$ and $P^6$ are each independently protecting groups, compound (A) is the formula:

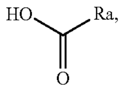

compound (B) is the formula:

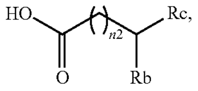

$R^2$ is

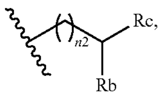

compound (C) is the formula:

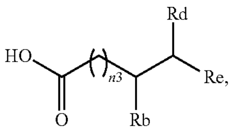

$R^2$ is

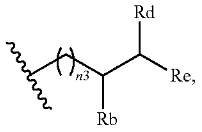

and other symbols are each as defined above.

The starting materials and reagents used in the reactions of each step in the above-mentioned production method, as well as the reaction conditions, may be the same as those described above in the production method for compound (II).

In another embodiment, cationic lipids represented by the following structural formulas and described in WO 2011/153493 can be mentioned.

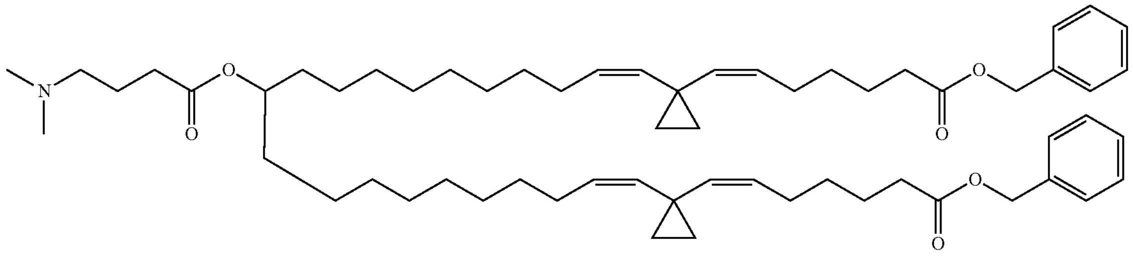

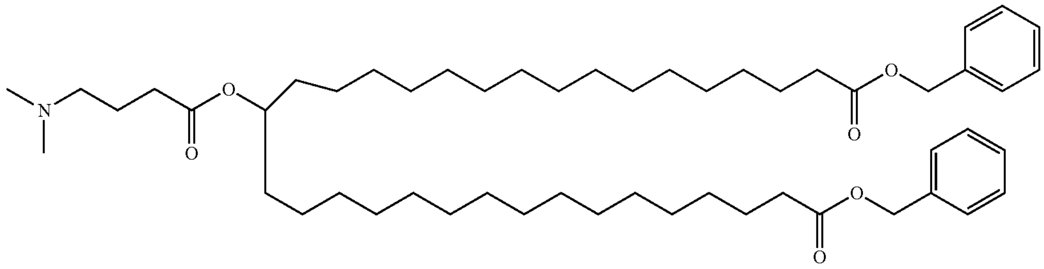

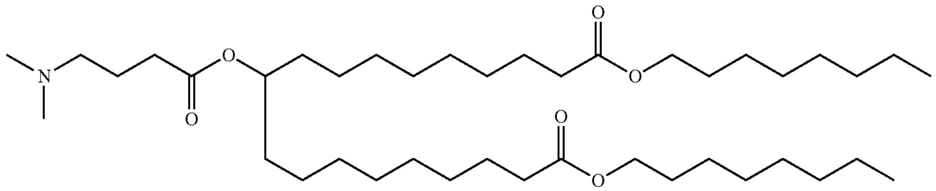

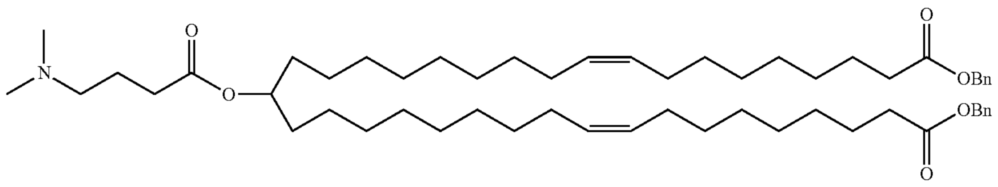

-continued
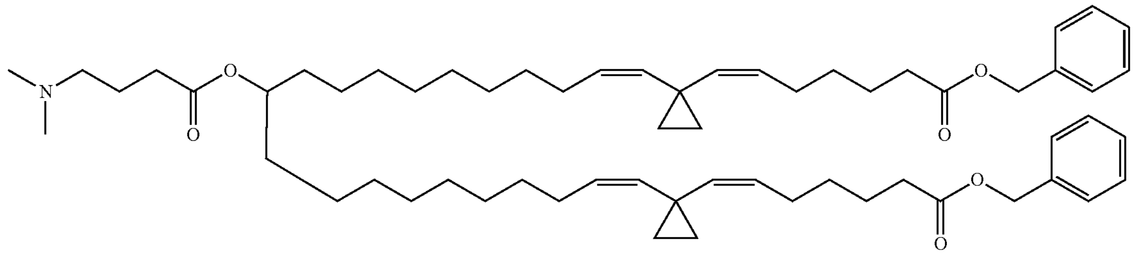
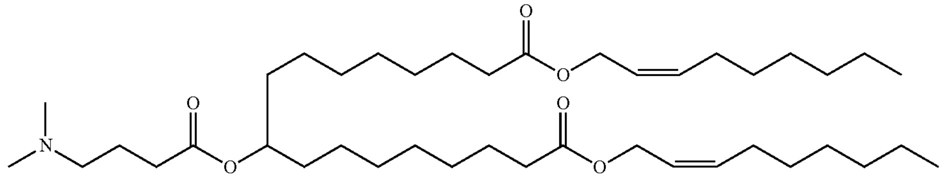
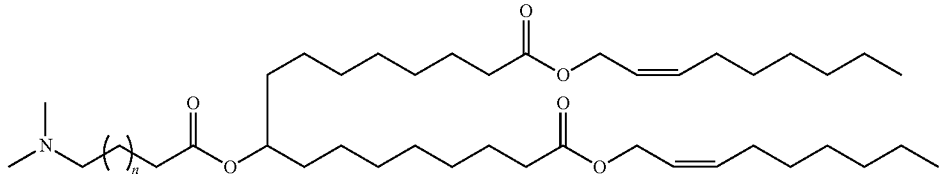
n = 0-2
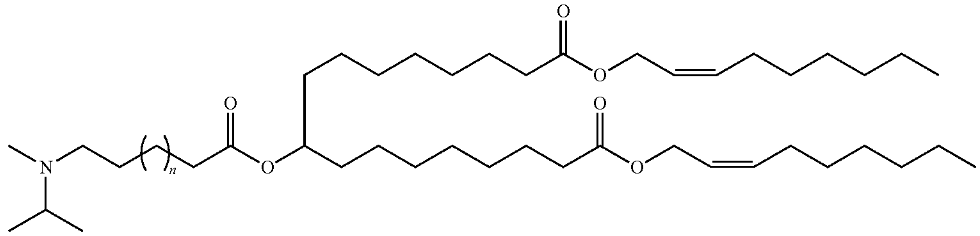
n = 0-2
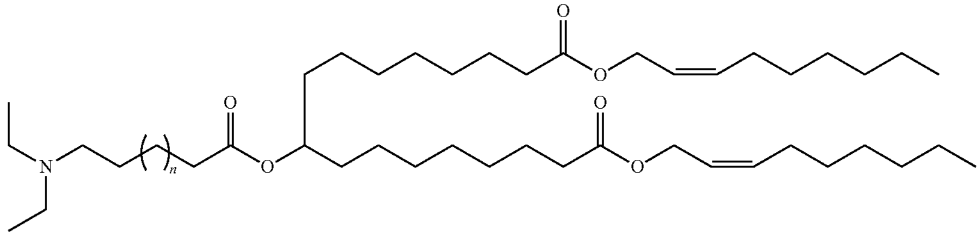
n = 0-2
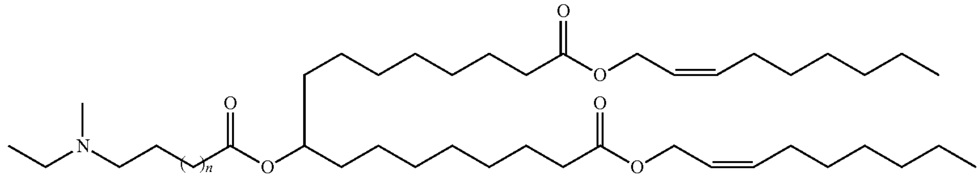
n = 0-2
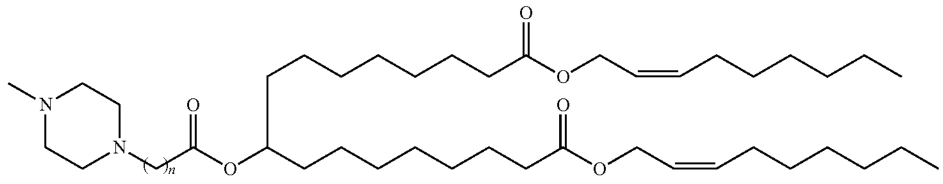
n = 1-3

-continued
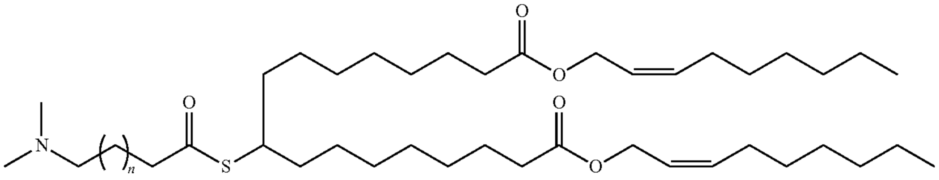
n = 0-2
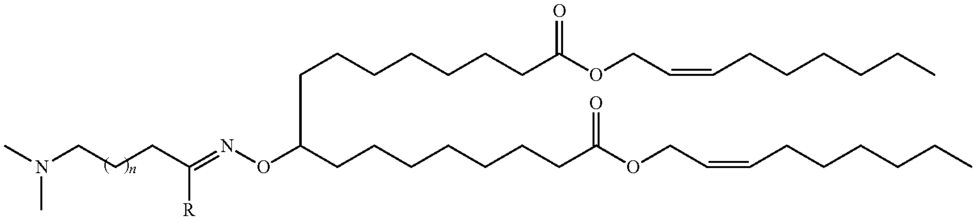
n = 0-2
R = H, Me
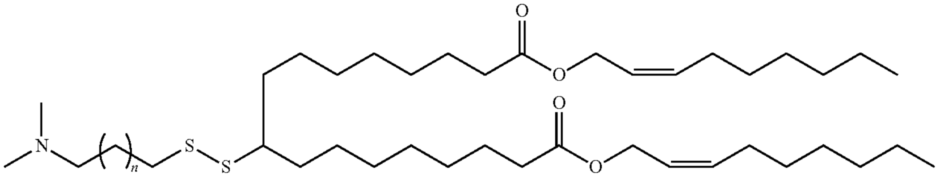
n = 0-2
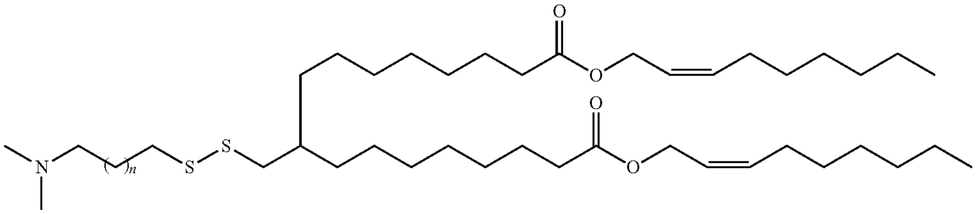
n = 0-2
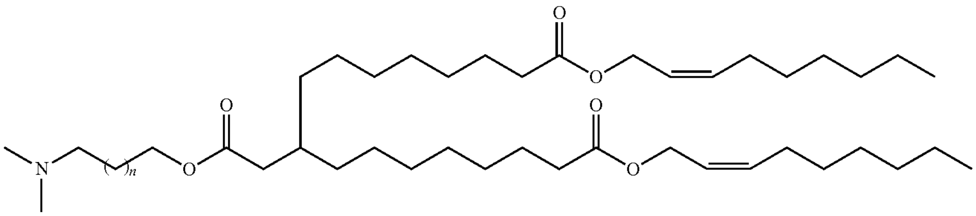
n = 0-2
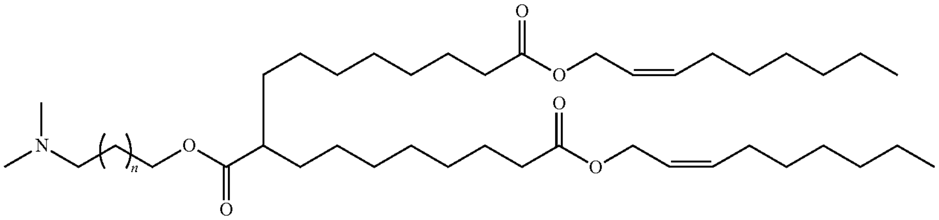
n = 0-2

-continued
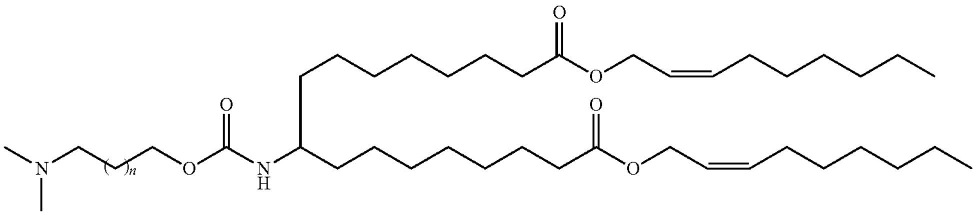
n = 0-2
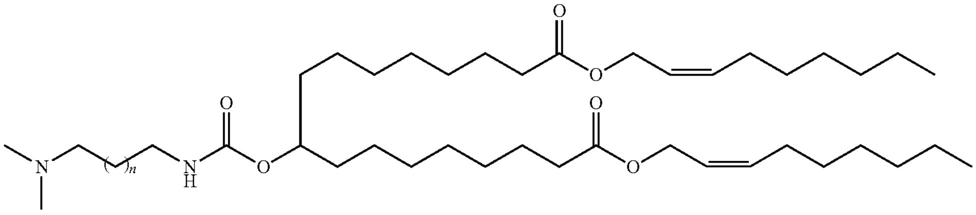
n = 0-2
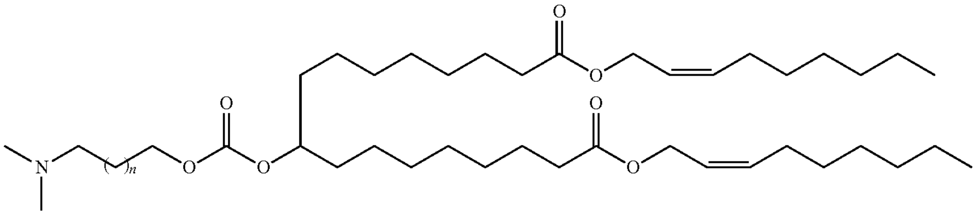
n = 0-2
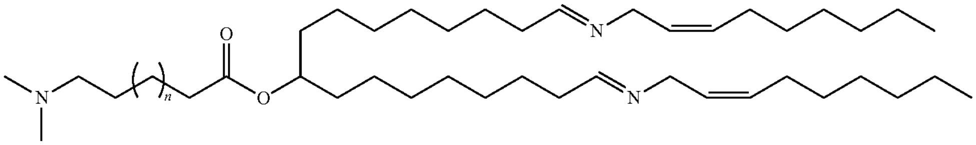
n = 0-2
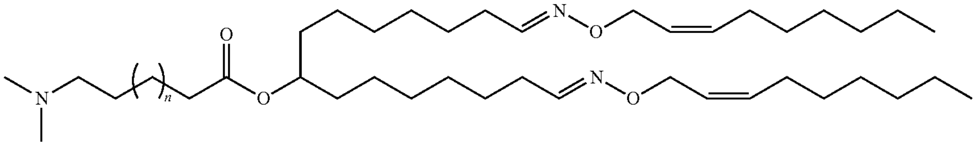
n = 0-2
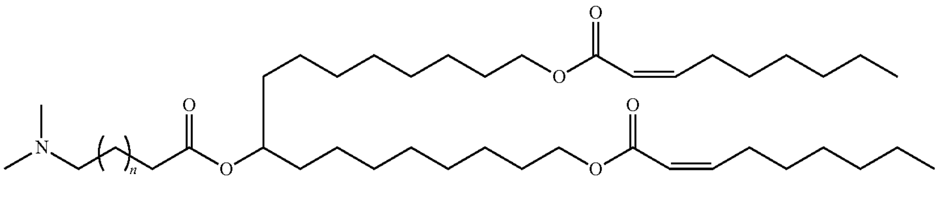
n = 0-2
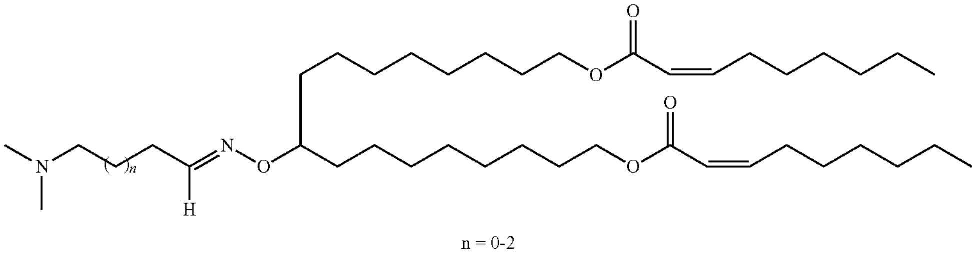
n = 0-2

-continued
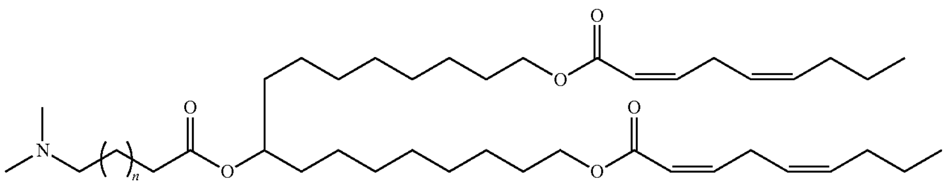
n = 0-2
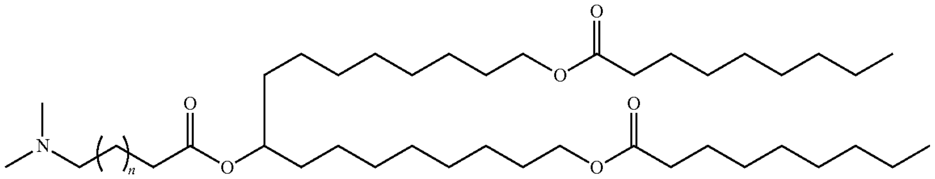
n = 0-2
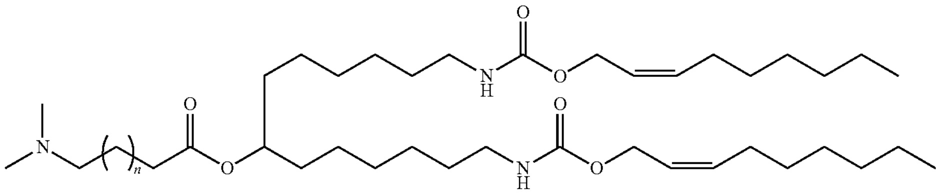
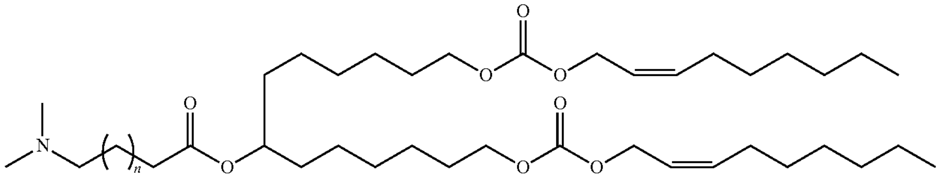
n = 0-2
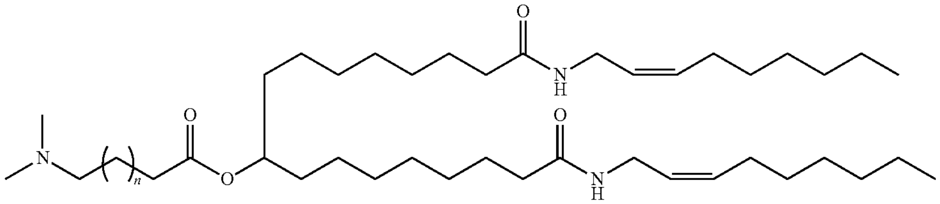
n = 0-2
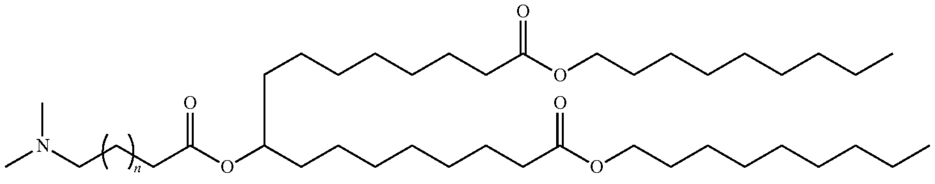
n = 0-2
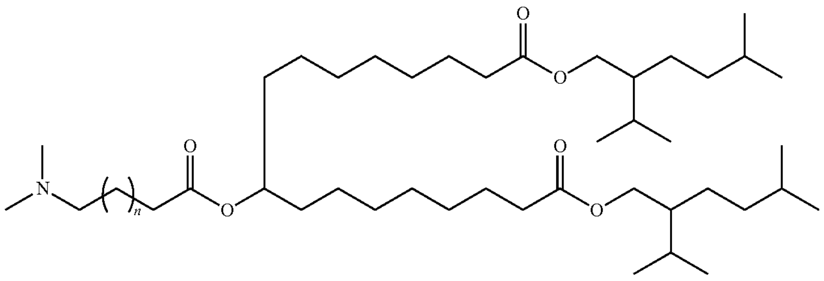
n = 0-2

-continued
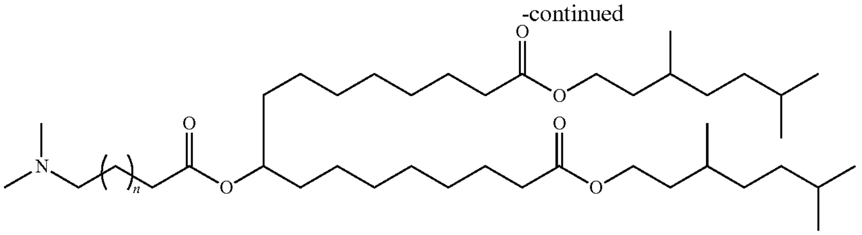
n = 0-2
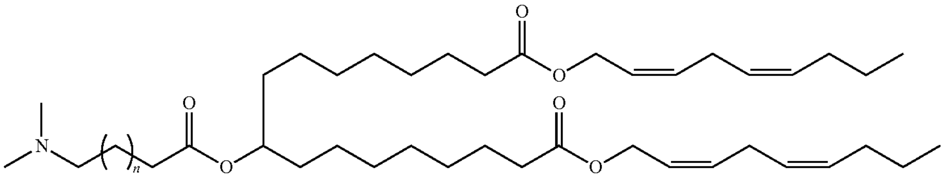
n = 0-2
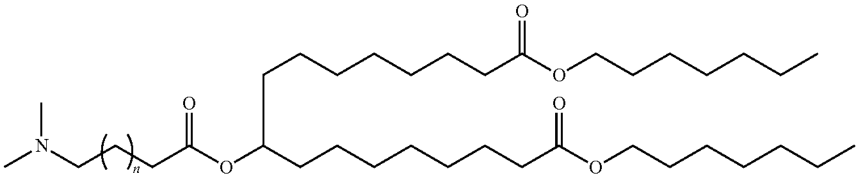
n = 0-2
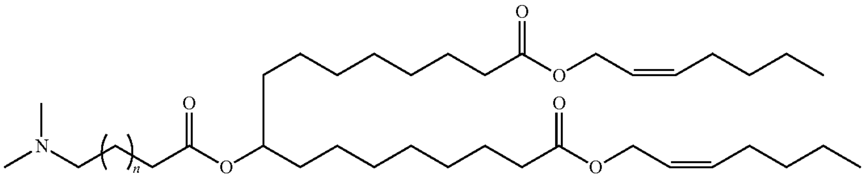
n = 0-2
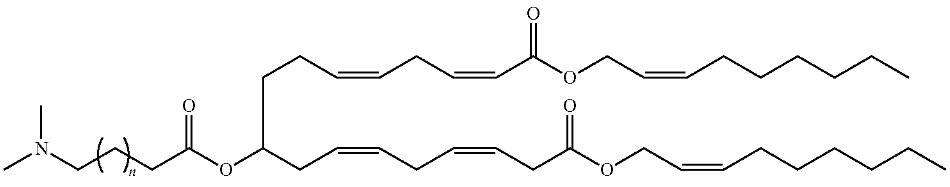
n = 0-2
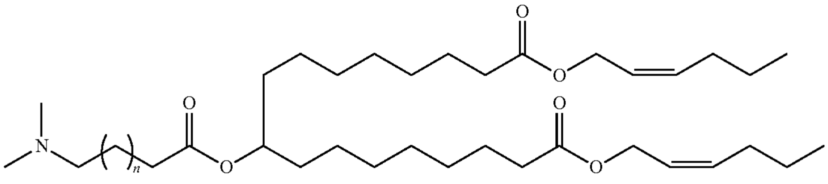
n = 0-2
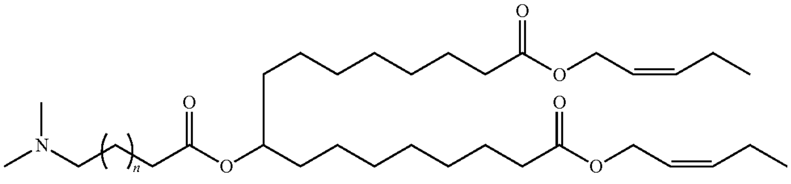
n = 0-2
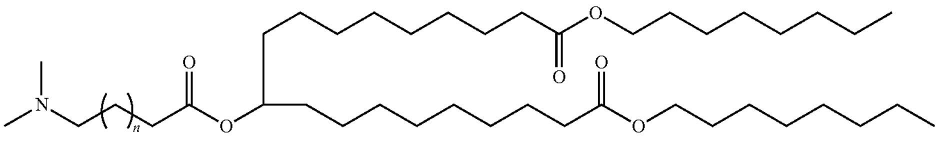
n = 0-2

-continued
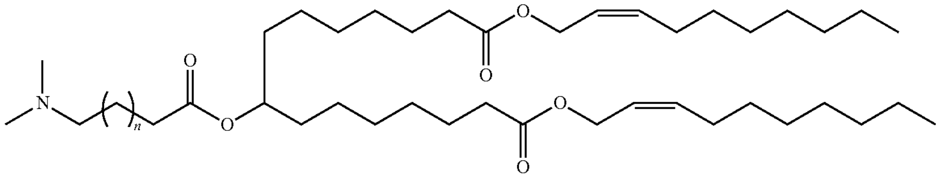
n = 0-2
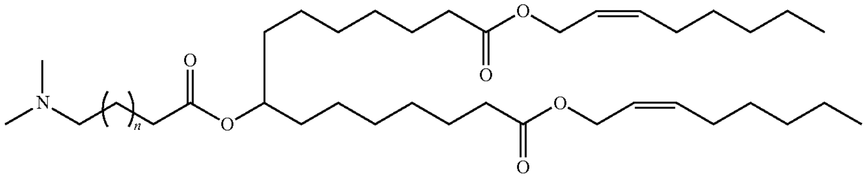
n = 0-2
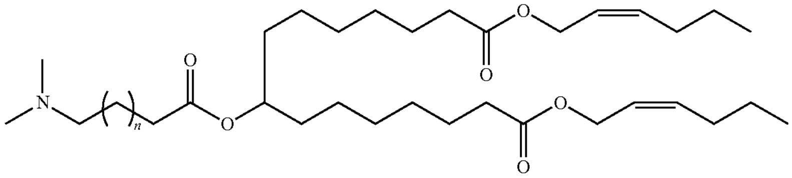
n = 0-2
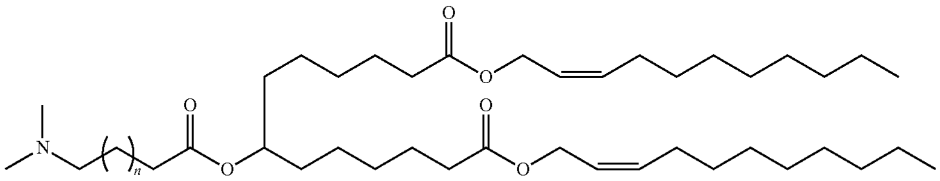
n = 0-2
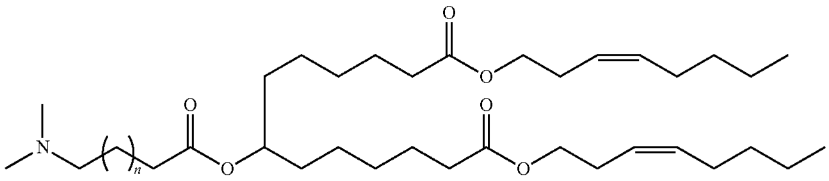
n = 0-2
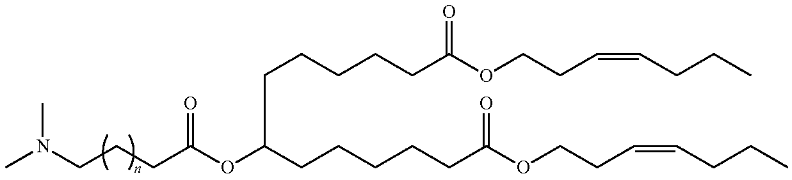
n = 0-2
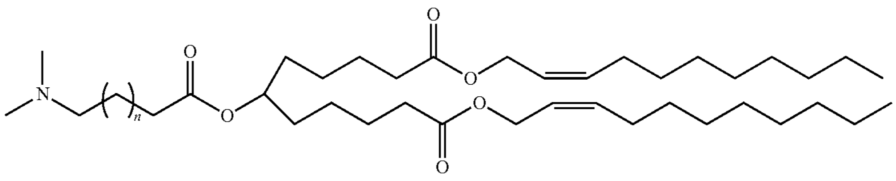
n = 0-2
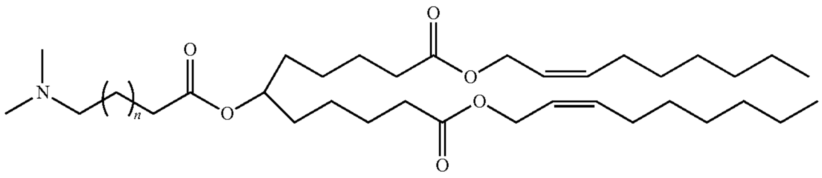
n = 0-2

-continued
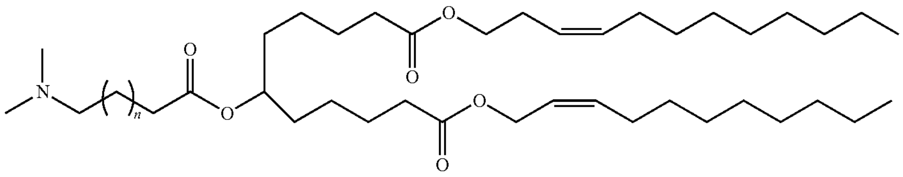
n = 0-2
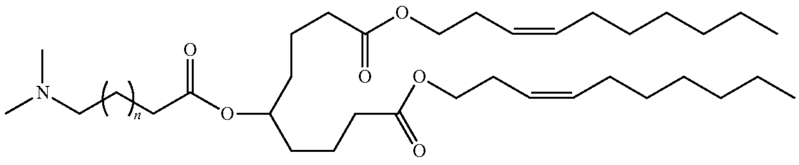
n = 0-2
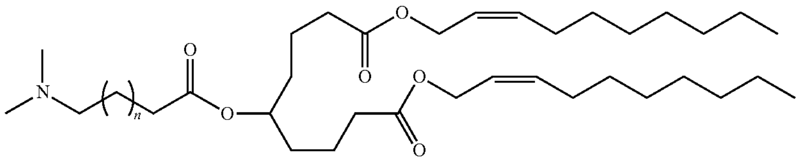
n = 0-2
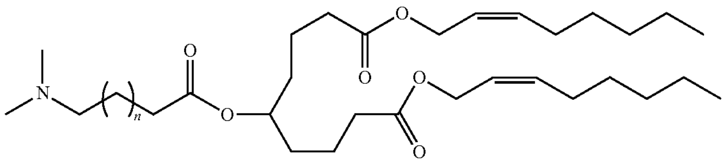
n = 0-2
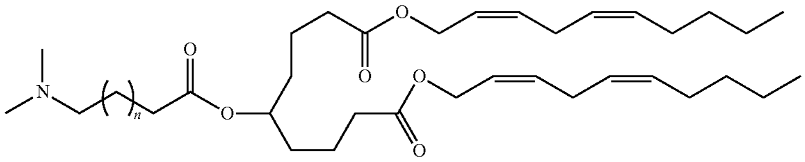
n = 0-2
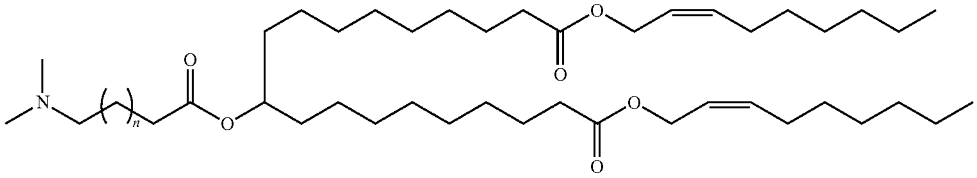
n = 0-2
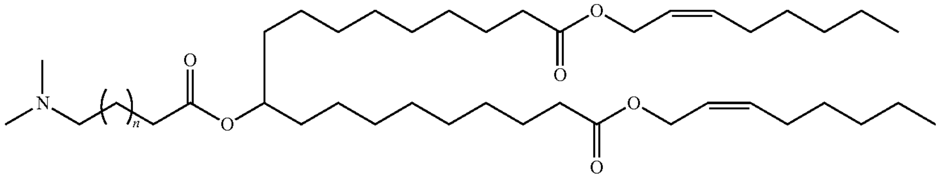
n = 0-2
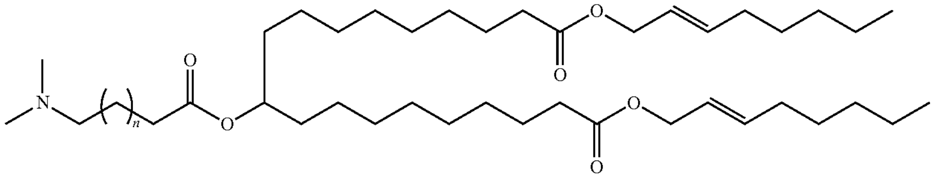
n = 0-2

-continued
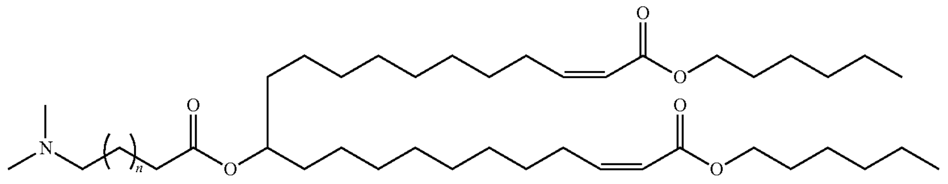
n = 0-2
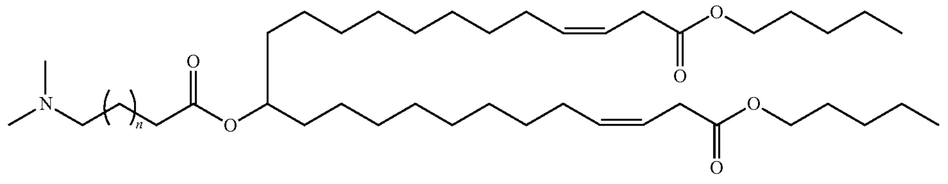
n = 0-2
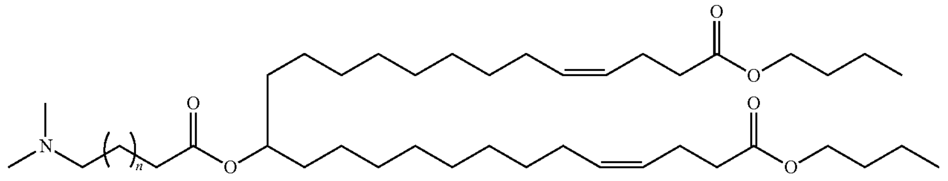
n = 0-2
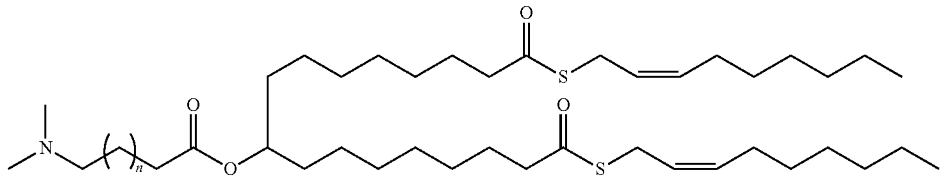
n = 0-2
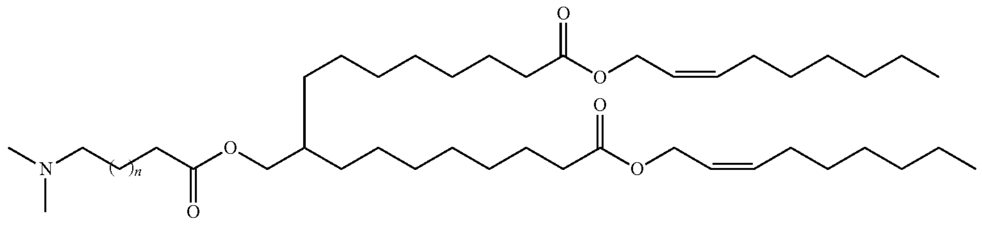
n = 0-2
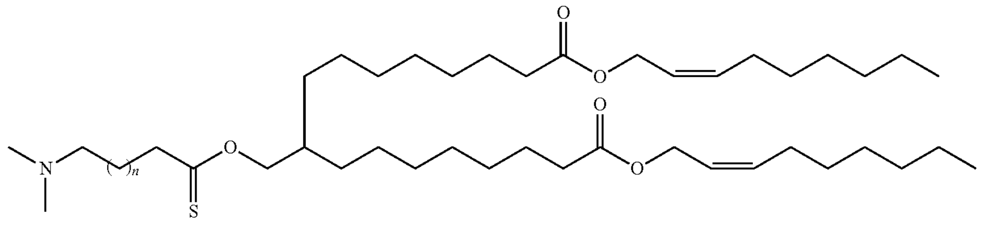
n = 0-2
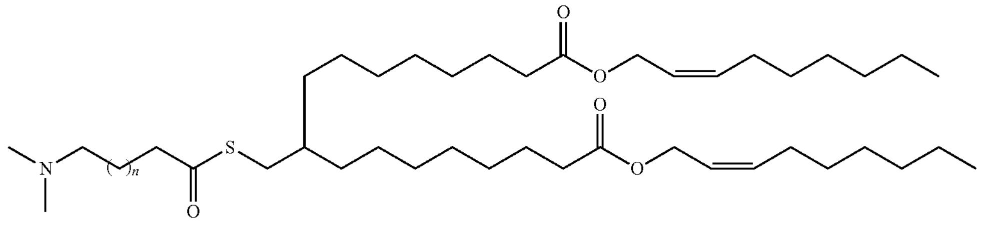
n = 0-2

-continued
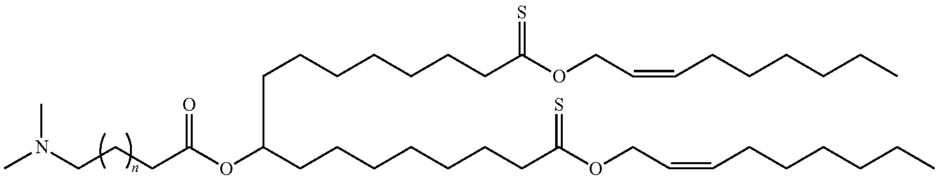
n = 0-2
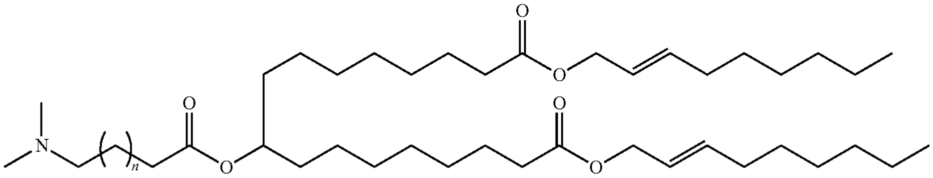
n = 0-2
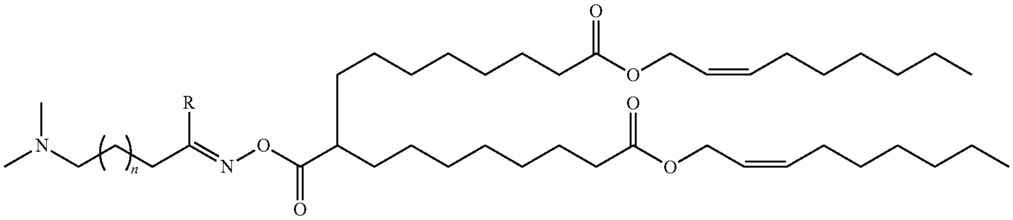
R = H, Me
n = 0-2
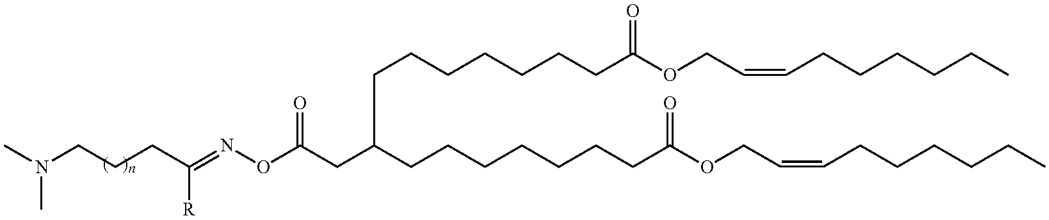
R = H, Me
n = 0-2
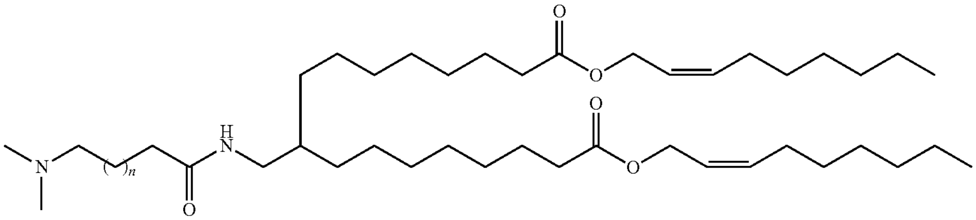
n = 0-2
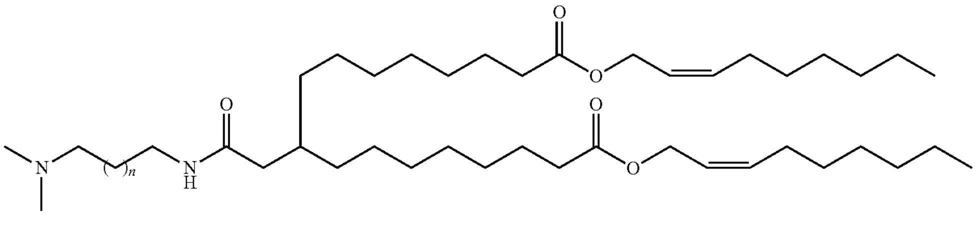
n = 0-2

-continued
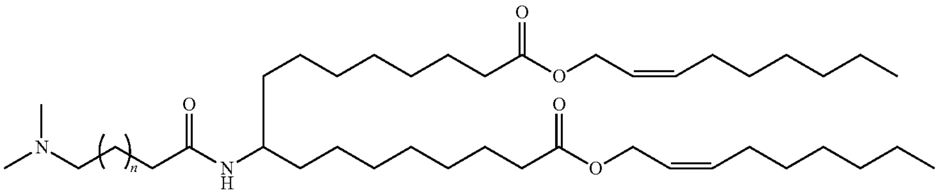
n = 0-2
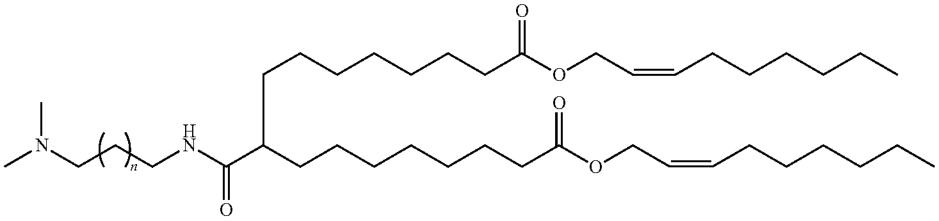
n = 0-2
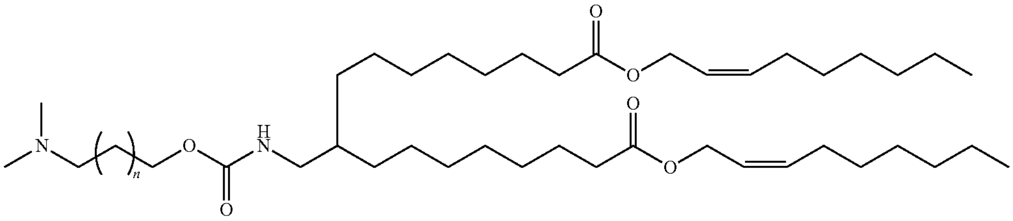
n = 0-2
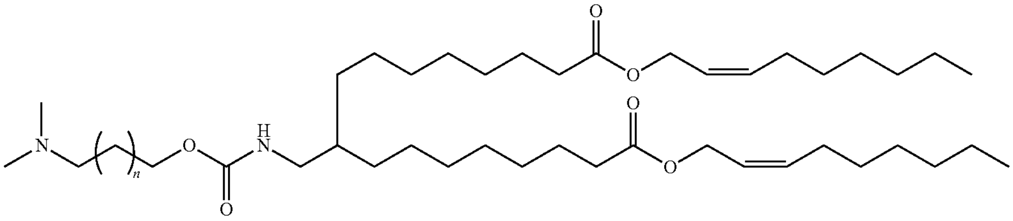
n = 0-2
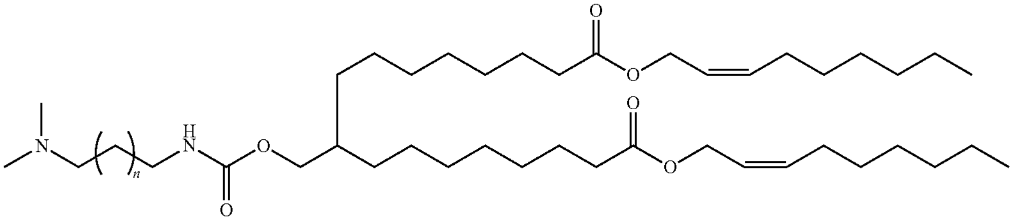
n = 0-2
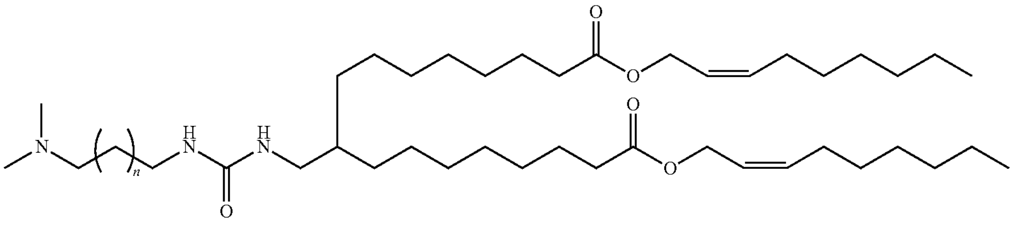
n = 0-2

-continued
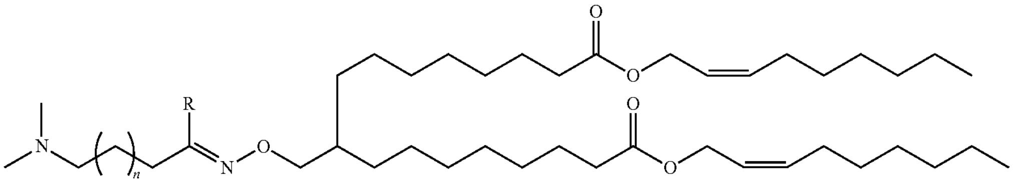
R = H, Me
n = 0-2
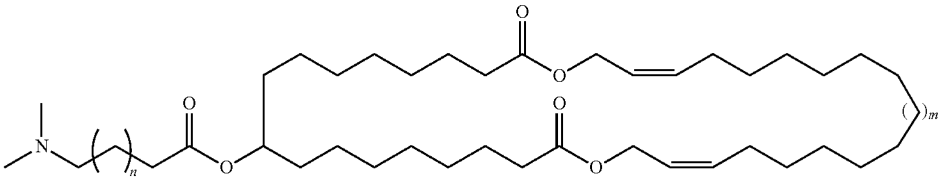
n = 0-2
m = 0-12
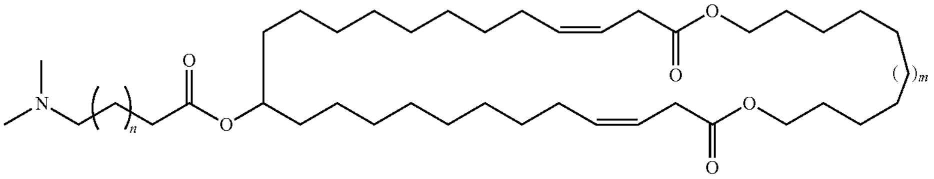
n = 0-2
m = 0-12
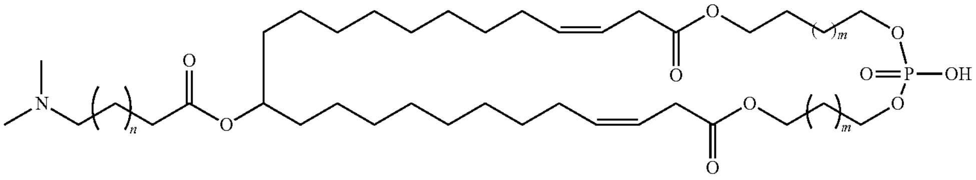
n = 0-2
m = 0-12
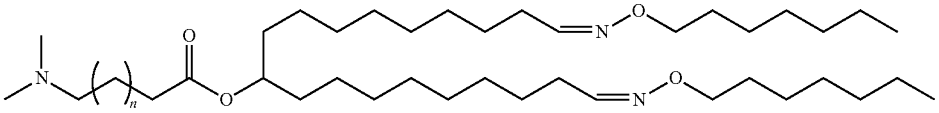
n = 0-2
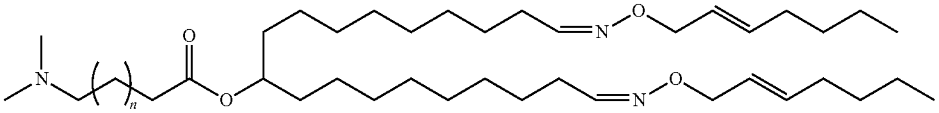
n = 0-2
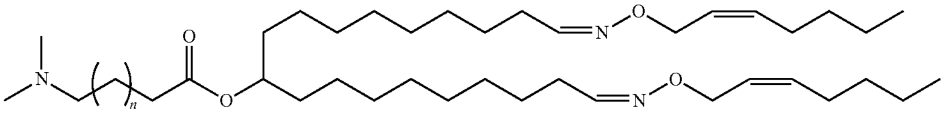
n = 0-2
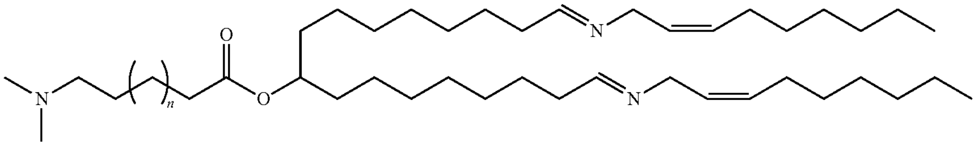
n = 0-2

-continued
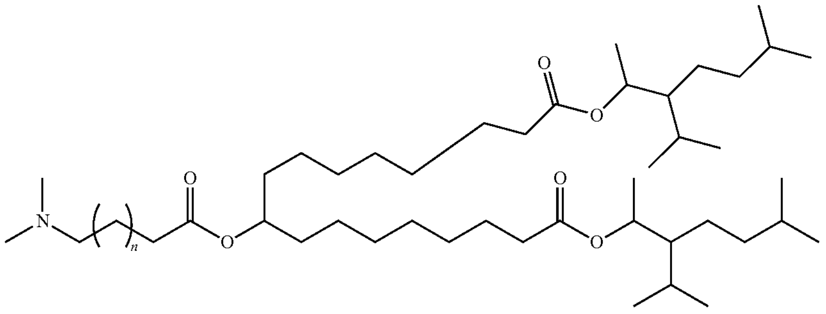
n = 0-2
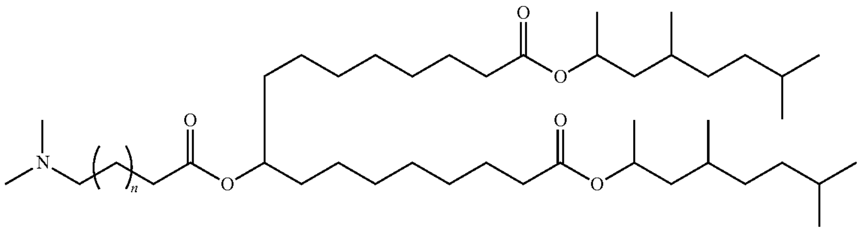
n = 0-2
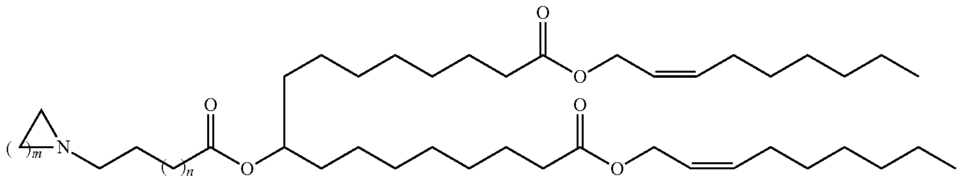
m = 1-6; n = 0-3
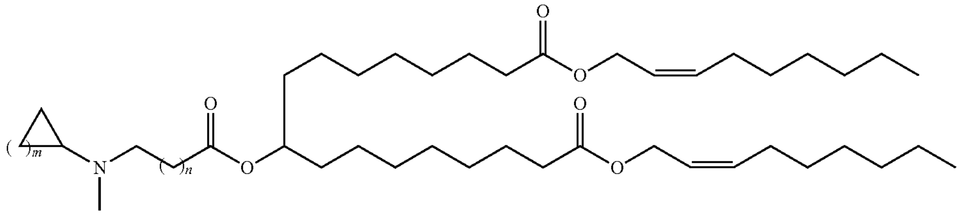
m = 1-6; n = 0-5
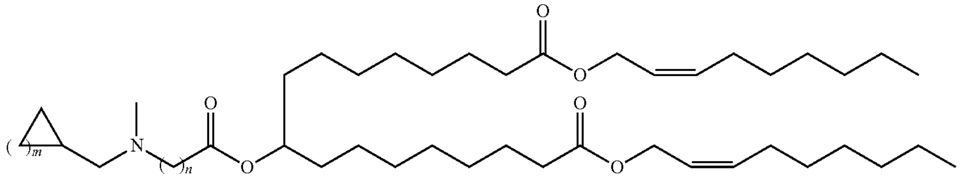
m = 1-6; n = 0-5
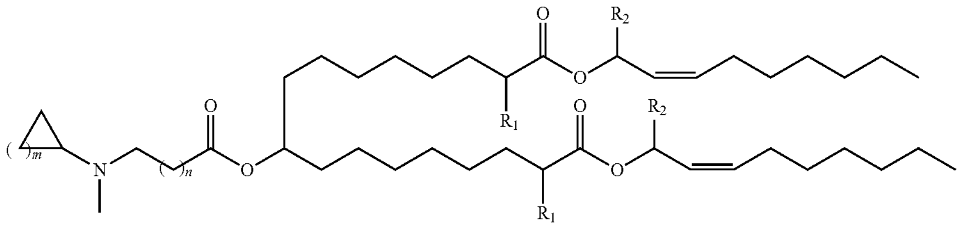
m = 1-6; n = 0-3
$R_1 = R_2 =$ Me, Et, iPr etc.
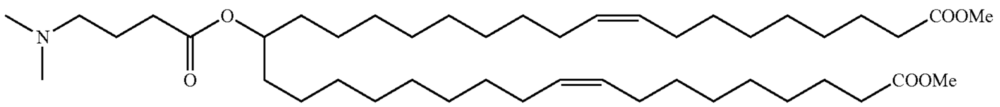

-continued
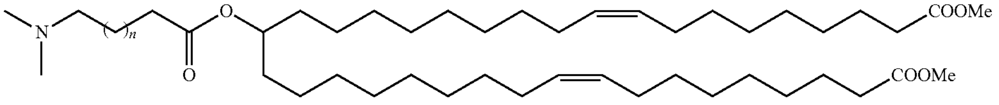
n = 0-2
(n = 1; ALNY-322
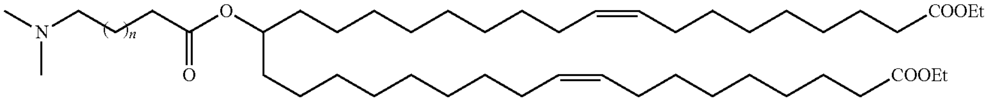
n = 0-2
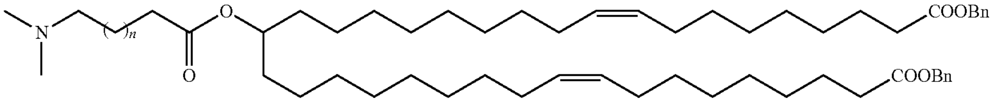
n = 0-2
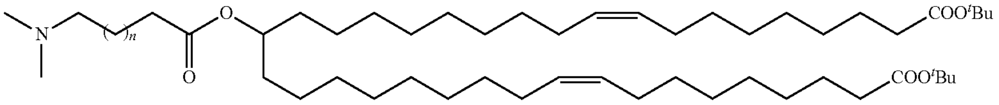
n = 0-2
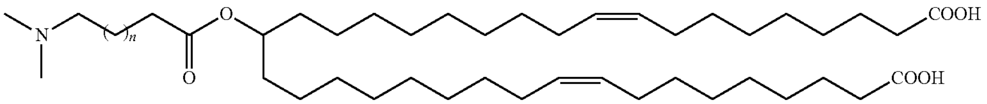
n = 0-2
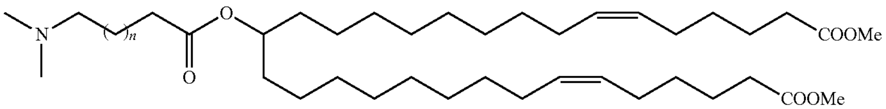
n = 0-2
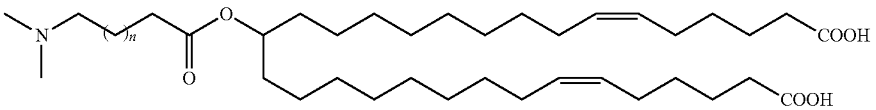
n = 0-2
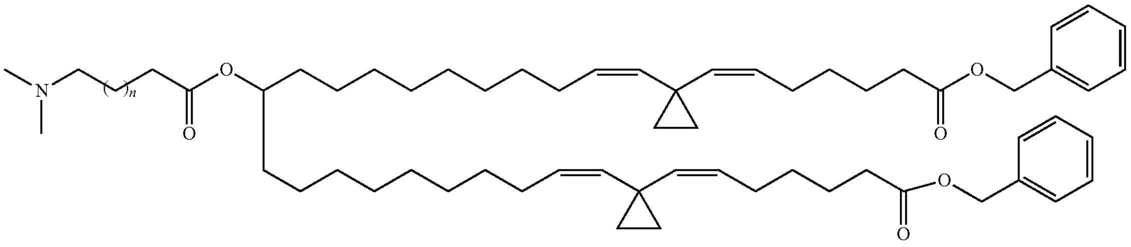
n = 0-2
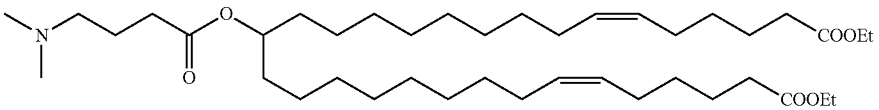
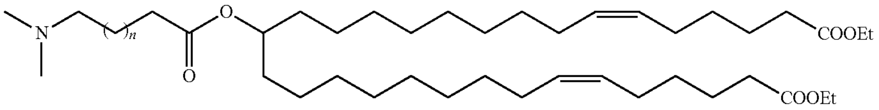
n = 0-2
(n = 1; ALNY-320
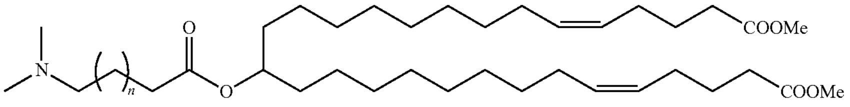
n = 0-2

-continued
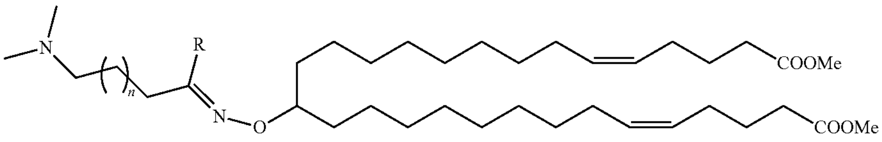
n = 0-2
R = H, Me
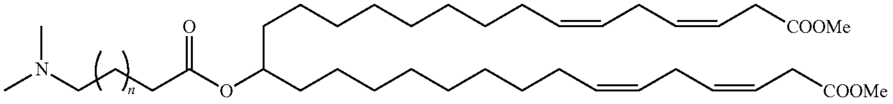
n = 0-2
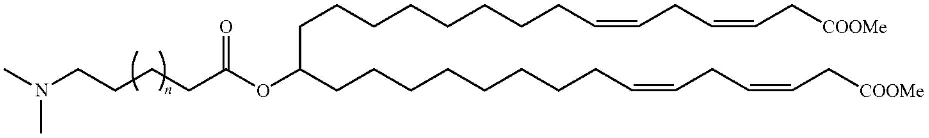
n = 0-2
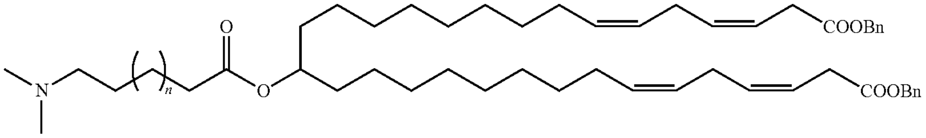
n = 0-2
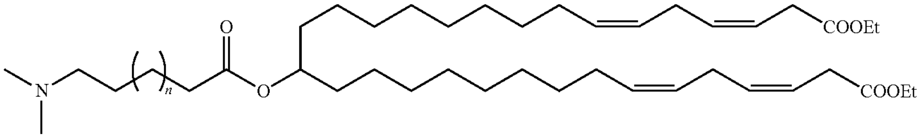
n = 0-2
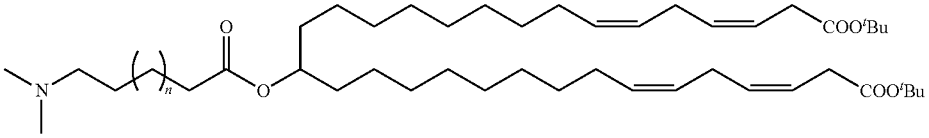
n = 0-2
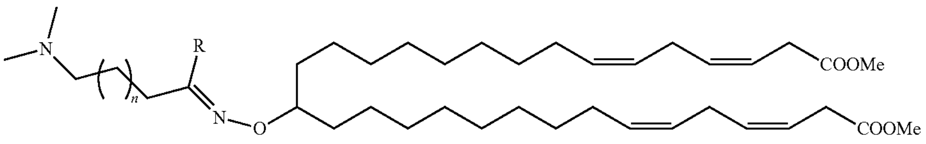
n = 0-2
R = H, Me
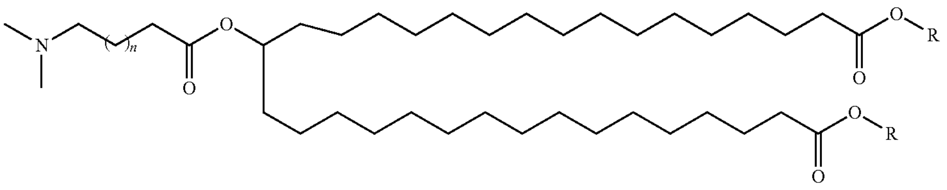
R = Me, Et, Pr, Bn, t-Bu. Ph, alkyl, aryl
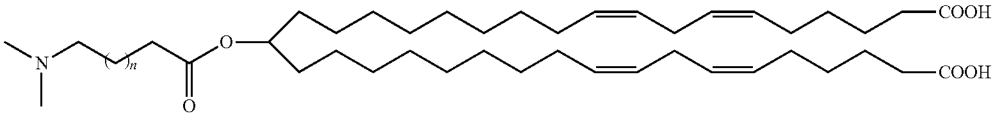
n = 0-2

-continued
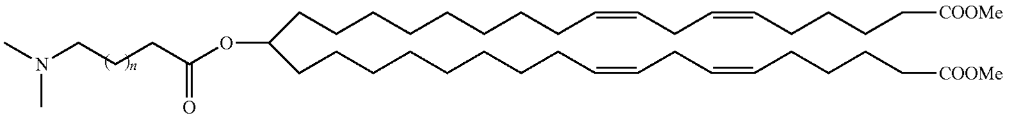
n = 0-2
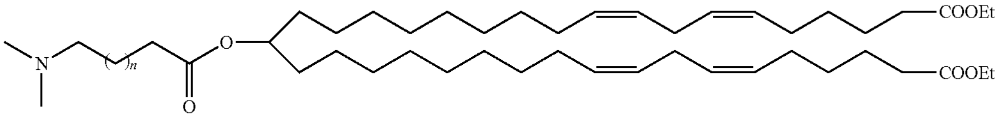
n = 0-2
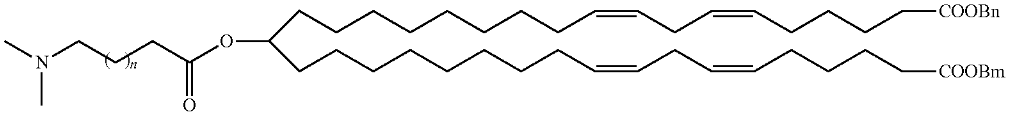
n = 0-2
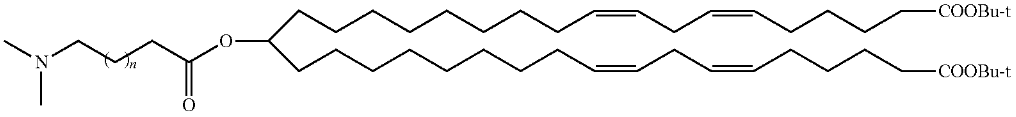
n = 0-2
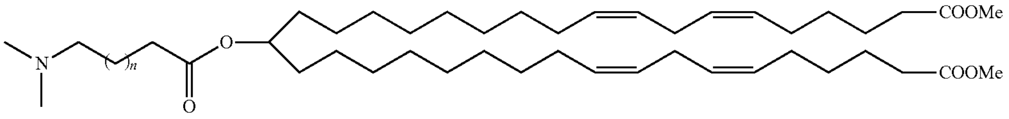
n = 0-2
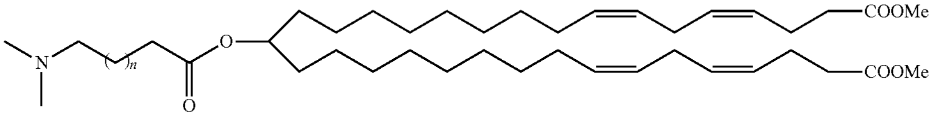
n = 0-2
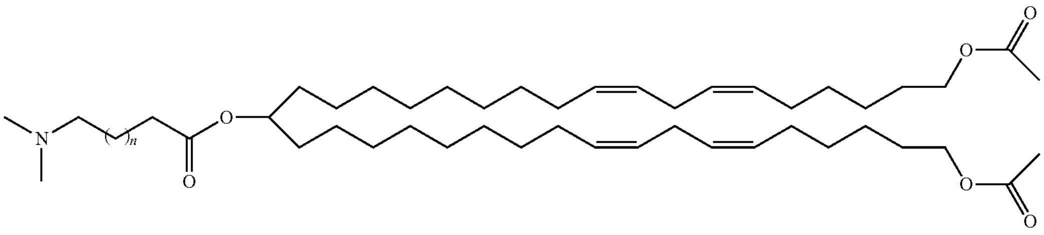
n = 0-2
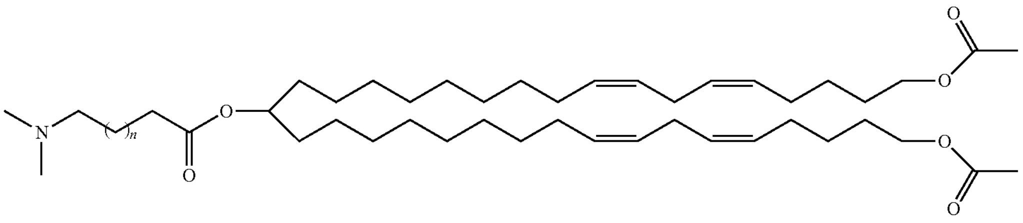
n = 0-2
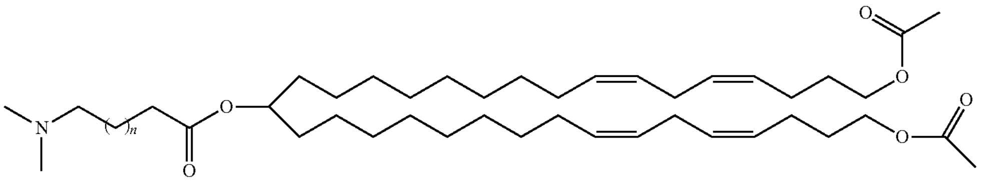
n = 0-2

-continued
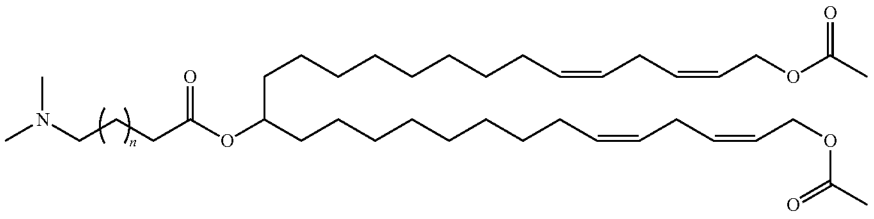
n = 0-2
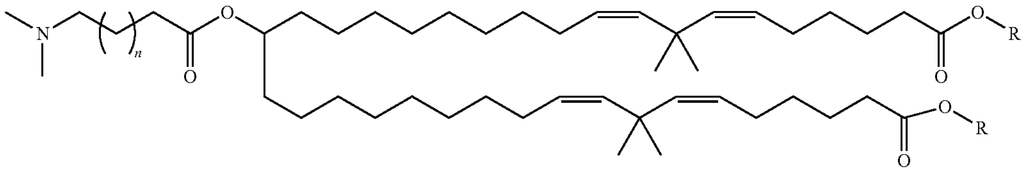
R = Me, Et, Pr, iPr, t-Bu, Bn, Ph, alkyl, aryl
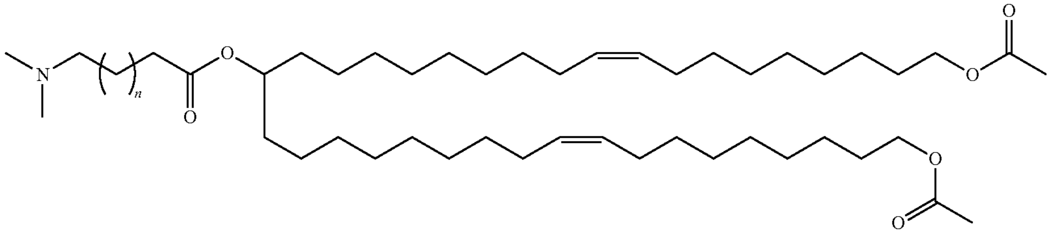
n = 0-2
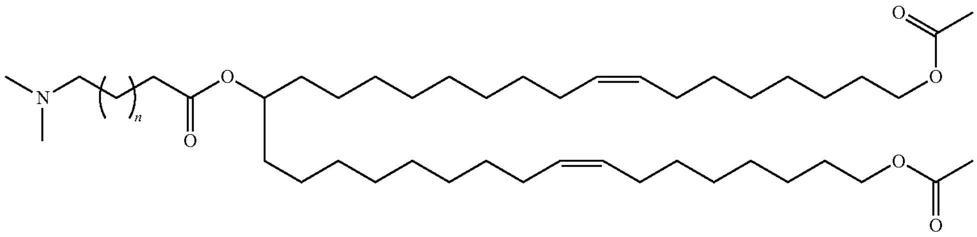
n = 0-2
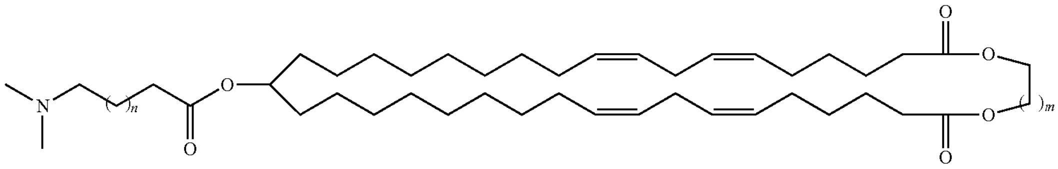
n = 0-2
m = 1-12
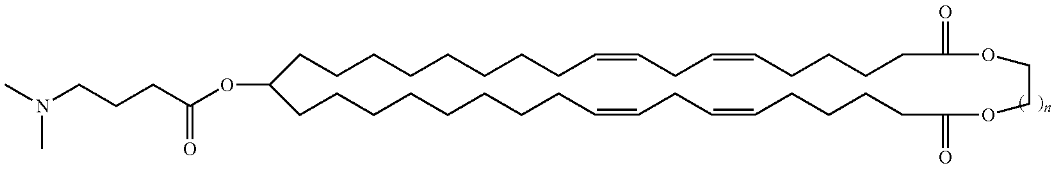
n = 1-12
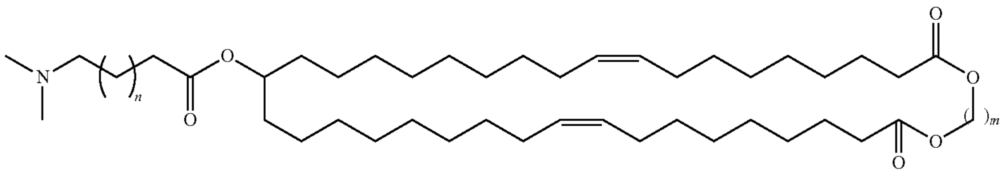
n = 0-2
m = 2-12

-continued
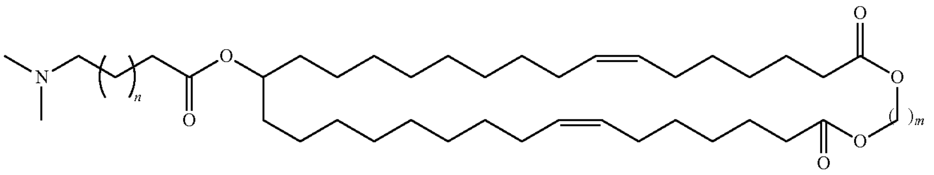
n = 0-2
m = 2-12
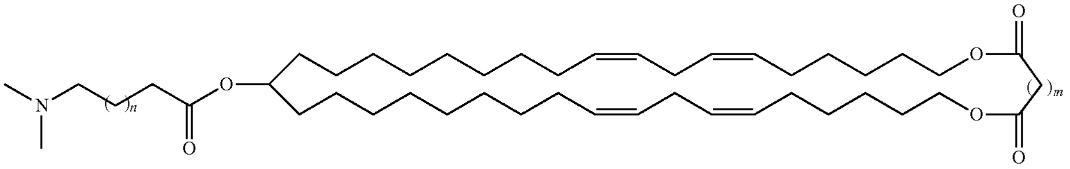
n = 0-2
m = 1-12
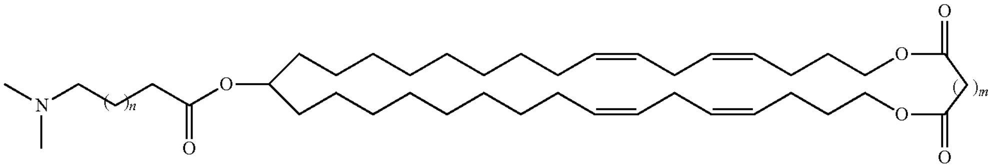
n = 0-2
m = 1-12
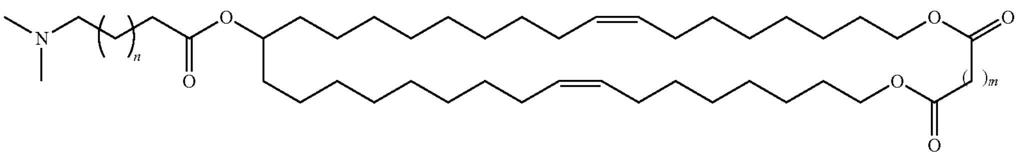
n = 0-2
m = 1-12
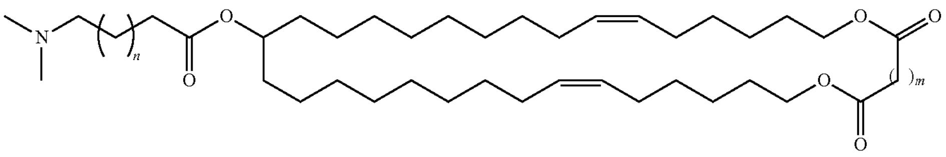
n = 0-2
m = 1-12
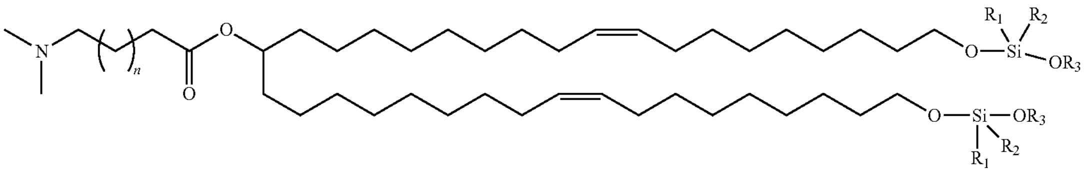
n = 0-2
$R_1 = R_2 = R_3 =$ Me, Et, iPr
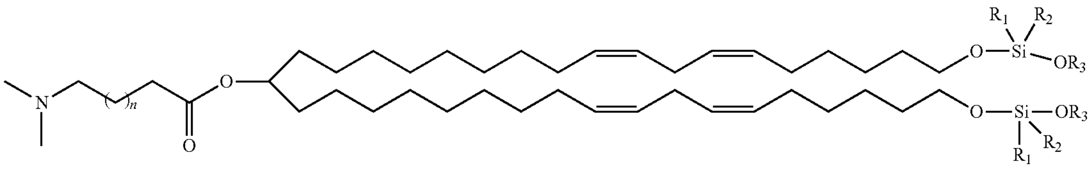
n = 0-2
$R_1 = R_2 = R_3 =$ Me, Et, iPr -continued
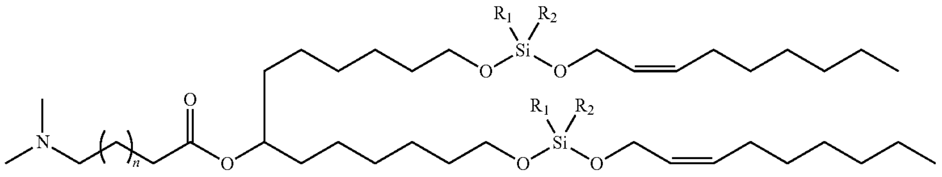
n = 0-2
$R_1 = R_2$ = Me, Et, iPr
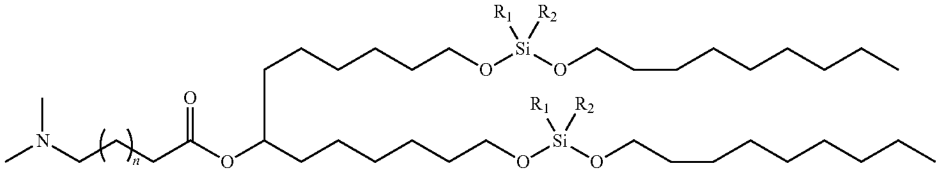
n = 0-2
$R_1 = R_2$ = Me, Et, iPr
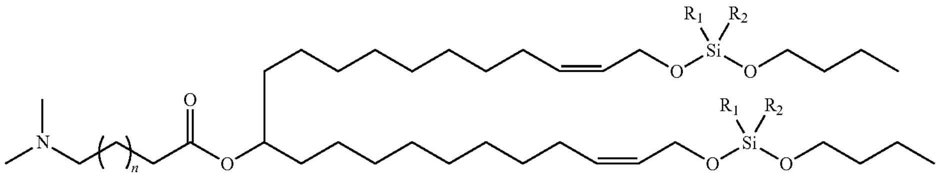
n = 0-2
$R_1 = R_2$ = Me, Et, iPr
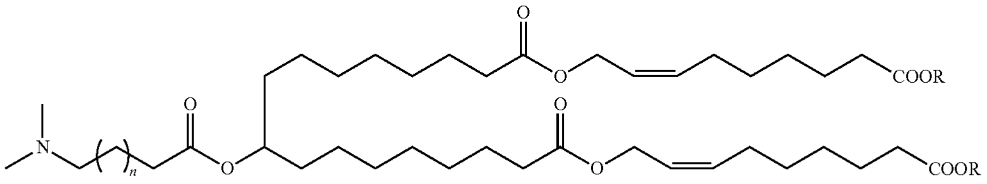
n = 0-2
R = Me, Et, Pr, iPr, t-Bu, Bn, Ph, alkyl, aryl
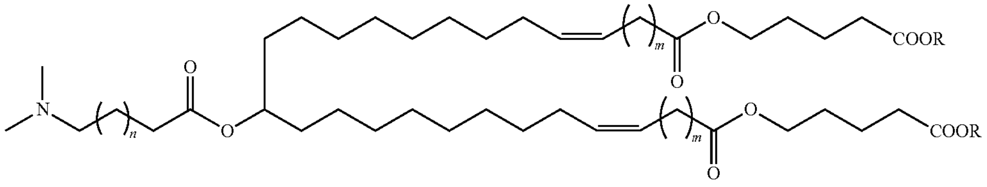
n = 0-2
R = Me, Et, Pr, iPr, t-Bu, Bn, Ph, alkyl, aryl
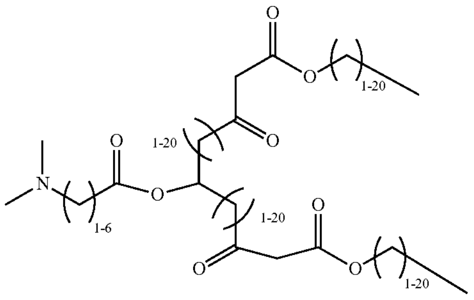
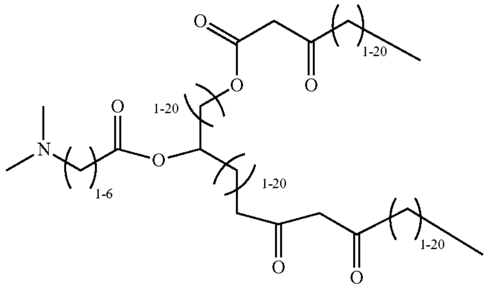
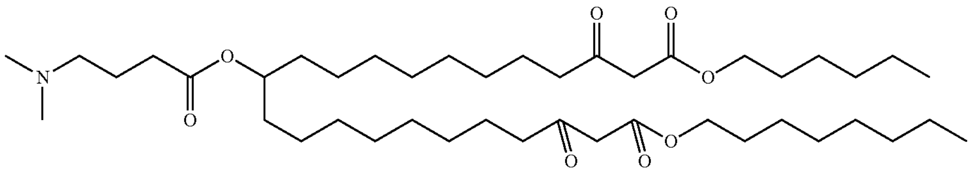

-continued
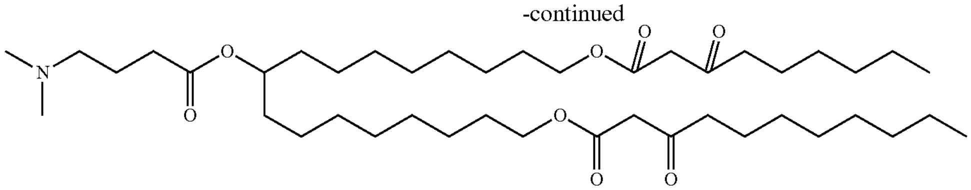
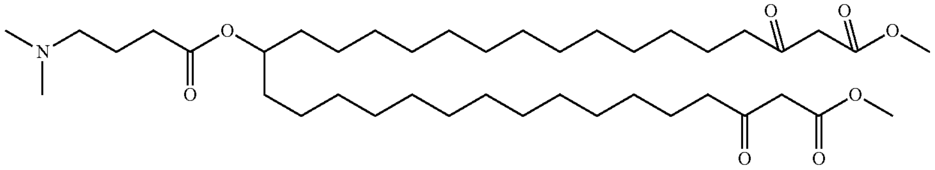
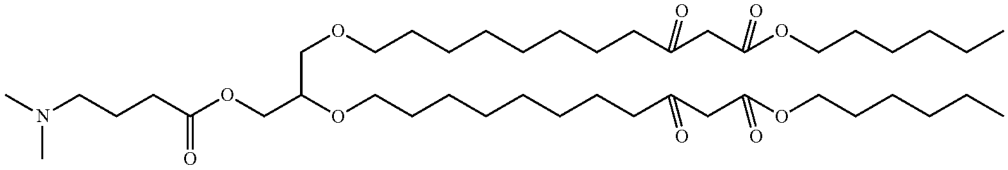
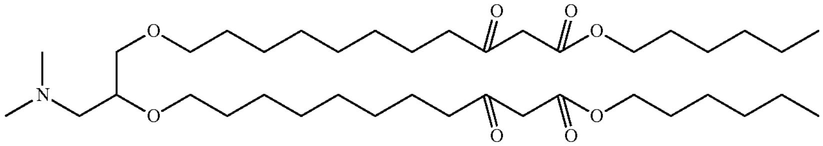
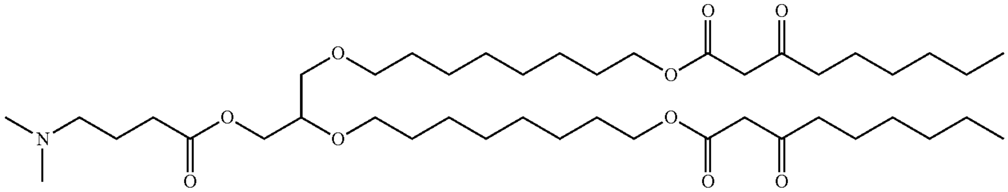
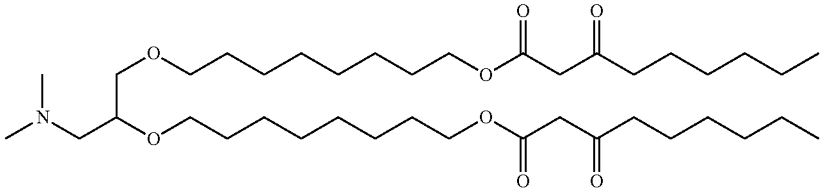
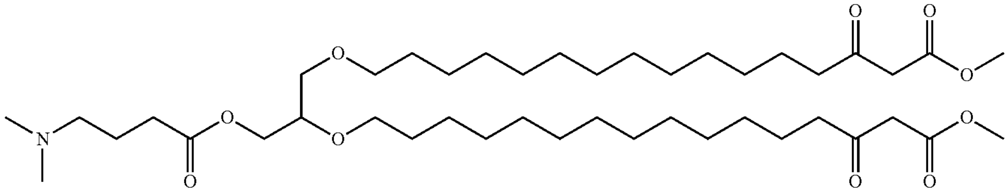
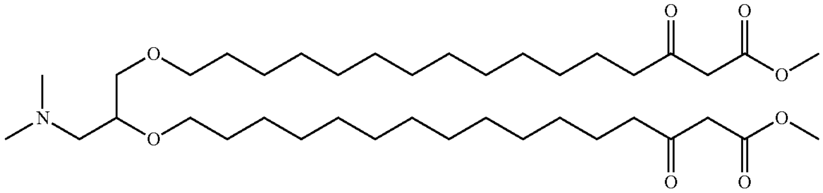

| 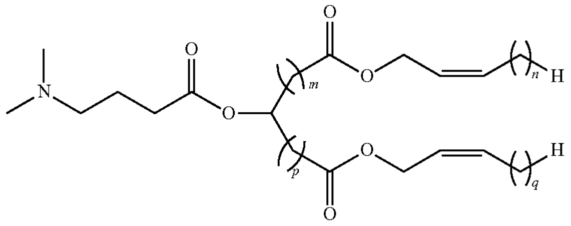 | | | | 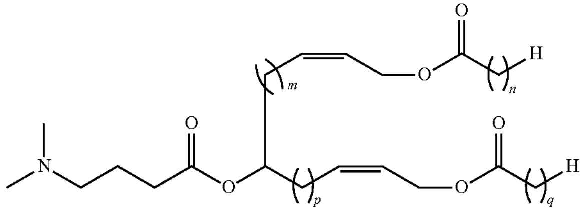 | | | |
|---|---|---|---|---|---|---|---|
| m | n | p | q | m | n | p | q |
| 1 | 12 | 1 | 12 | 12 | 1 | 12 | 1 |
| 2 | 11 | 2 | 11 | 11 | 2 | 11 | 2 |
| 3 | 10 | 3 | 10 | 10 | 3 | 10 | 3 |
| 4 | 9 | 4 | 9 | 9 | 4 | 9 | 4 |
| 5 | 8 | 5 | 8 | 8 | 5 | 8 | 5 |
| 6 | 7 | 6 | 7 | 7 | 6 | 7 | 6 |
| 7 | 6 | 7 | 6 | 6 | 7 | 6 | 7 |
| 8 | 5 | 8 | 5 | 5 | 8 | 5 | 8 |
| 9 | 4 | 9 | 4 | 4 | 9 | 4 | 9 |
| 10 | 3 | 10 | 3 | 3 | 10 | 3 | 10 |
| 11 | 2 | 11 | 2 | 2 | 11 | 2 | 11 |
| 12 | 1 | 12 | 1 | 1 | 12 | 1 | 12 |
| 1 | 12 | 2 | 11 | 12 | 1 | 11 | 2 |
| 2 | 11 | 3 | 10 | 11 | 2 | 10 | 3 |
| 3 | 10 | 4 | 9 | 10 | 3 | 9 | 4 |
| 4 | 9 | 5 | 8 | 9 | 4 | 8 | 5 |
| 5 | 8 | 6 | 7 | 8 | 5 | 7 | 6 |
| 6 | 7 | 7 | 6 | 7 | 6 | 6 | 7 |
| 7 | 6 | 8 | 5 | 6 | 7 | 5 | 8 |
| 8 | 5 | 9 | 4 | 5 | 8 | 4 | 9 |
| 9 | 4 | 10 | 3 | 4 | 9 | 3 | 10 |
| 10 | 3 | 11 | 2 | 3 | 10 | 2 | 11 |
| 11 | 2 | 12 | 1 | 2 | 11 | 1 | 12 |
| 12 | 1 | 1 | 12 | 1 | 12 | 12 | 1 |
| 1 | 12 | 3 | 10 | 12 | 1 | 10 | 3 |
| 2 | 11 | 4 | 9 | 11 | 2 | 9 | 4 |
| 3 | 10 | 5 | 8 | 10 | 3 | 8 | 5 |
| 4 | 9 | 6 | 7 | 9 | 4 | 7 | 6 |
| 5 | 8 | 7 | 6 | 8 | 5 | 6 | 7 |
| 6 | 7 | 8 | 5 | 7 | 6 | 5 | 8 |
| 7 | 6 | 9 | 4 | 6 | 7 | 4 | 9 |
| 8 | 5 | 10 | 3 | 5 | 8 | 3 | 10 |
| 9 | 4 | 11 | 2 | 4 | 9 | 2 | 11 |
| 10 | 3 | 12 | 1 | 3 | 10 | 1 | 12 |
| 11 | 2 | 2 | 11 | 2 | 11 | 11 | 2 |
| 12 | 1 | 4 | 9 | 1 | 12 | 10 | 3 |
| 1 | 12 | 4 | 9 | 12 | 1 | 9 | 4 |
| 2 | 11 | 5 | 8 | 11 | 2 | 8 | 5 |

-continued

| | | | | | | | |
|---|---|---|---|---|---|---|---|
| 3 | 10 | 6 | 7 | 10 | 3 | 7 | 6 |
| 4 | 9 | 7 | 6 | 9 | 4 | 6 | 7 |
| 5 | 8 | 8 | 5 | 8 | 5 | 5 | 8 |
| 6 | 7 | 9 | 4 | 7 | 6 | 4 | 9 |
| 7 | 6 | 10 | 3 | 6 | 7 | 3 | 10 |
| 8 | 5 | 11 | 2 | 5 | 8 | 2 | 11 |
| 9 | 4 | 12 | 1 | 4 | 9 | 1 | 12 |
| 10 | 3 | 2 | 11 | 3 | 10 | 11 | 2 |
| 11 | 2 | 3 | 10 | 2 | 11 | 10 | 3 |
| 12 | 1 | 4 | 9 | 1 | 12 | 11 | 2 |
| 1 | 12 | 5 | 8 | 12 | 1 | 8 | 5 |
| 2 | 11 | 6 | 7 | 11 | 2 | 7 | 6 |
| 3 | 10 | 7 | 6 | 10 | 3 | 6 | 7 |
| 4 | 9 | 8 | 5 | 9 | 4 | 5 | 8 |
| 5 | 8 | 9 | 4 | 8 | 5 | 4 | 9 |
| 6 | 7 | 10 | 3 | 7 | 6 | 3 | 10 |
| 7 | 6 | 11 | 2 | 6 | 7 | 2 | 11 |
| 8 | 5 | 12 | 1 | 5 | 8 | 1 | 12 |
| 9 | 4 | 2 | 11 | 4 | 9 | 11 | 2 |
| 10 | 3 | 3 | 10 | 3 | 10 | 10 | 3 |
| 11 | 2 | 4 | 9 | 2 | 11 | 11 | 2 |
| 12 | 1 | 5 | 8 | 1 | 12 | 12 | 1 |
| 1 | 12 | 6 | 7 | 12 | 1 | 7 | 6 |
| 2 | 11 | 7 | 6 | 11 | 2 | 6 | 7 |
| 3 | 10 | 8 | 5 | 10 | 3 | 5 | 8 |
| 4 | 9 | 9 | 4 | 9 | 4 | 4 | 9 |
| 5 | 8 | 10 | 3 | 8 | 5 | 3 | 10 |
| 6 | 7 | 11 | 2 | 7 | 6 | 2 | 11 |
| 7 | 6 | 12 | 1 | 6 | 7 | 1 | 12 |
| 8 | 5 | 2 | 11 | 5 | 8 | 11 | 2 |
| 9 | 4 | 3 | 10 | 4 | 9 | 10 | 3 |
| 10 | 3 | 4 | 9 | 3 | 10 | 11 | 2 |
| 11 | 2 | 5 | 8 | 2 | 11 | 12 | 1 |
| 12 | 1 | 6 | 7 | 1 | 12 | 1 | 12 |
| 1 | 12 | 7 | 6 | 12 | 1 | 6 | 7 |
| 2 | 11 | 8 | 5 | 11 | 2 | 5 | 8 |
| 3 | 10 | 9 | 4 | 10 | 3 | 4 | 9 |
| 4 | 9 | 8 | 5 | 9 | 4 | 3 | 10 |
| 5 | 8 | 9 | 4 | 8 | 5 | 2 | 11 |
| 6 | 7 | 10 | 3 | 7 | 6 | 1 | 12 |
| 7 | 6 | 11 | 2 | 6 | 7 | 11 | 2 |
| 8 | 5 | 12 | 1 | 5 | 8 | 10 | 3 |
| 9 | 4 | 2 | 11 | 4 | 9 | 11 | 2 |
| 10 | 3 | 3 | 10 | 3 | 10 | 12 | 1 |
| 11 | 2 | 4 | 9 | 2 | 11 | 1 | 12 |
| 12 | 1 | 5 | 8 | 1 | 12 | 2 | 11 |

-continued
| 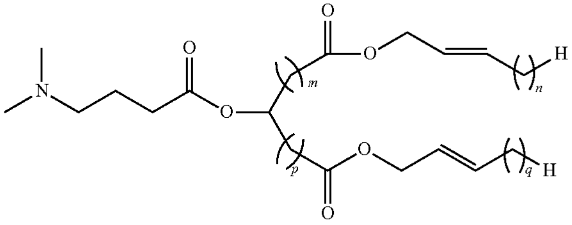 | | | | 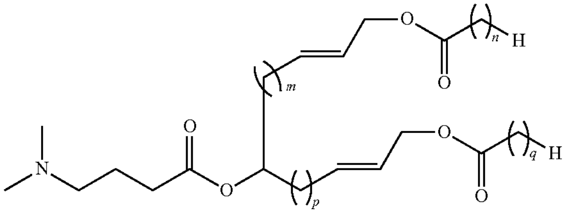 | | | |
|---|---|---|---|---|---|---|---|
| m | n | p | q | m | n | p | q |
| 1 | 12 | 1 | 12 | 12 | 1 | 12 | 1 |
| 2 | 11 | 2 | 11 | 11 | 2 | 11 | 2 |
| 3 | 10 | 3 | 10 | 10 | 3 | 10 | 3 |
| 4 | 9 | 4 | 9 | 9 | 4 | 9 | 4 |
| 5 | 8 | 5 | 8 | 8 | 5 | 8 | 5 |
| 6 | 7 | 6 | 7 | 7 | 6 | 7 | 6 |
| 7 | 6 | 7 | 6 | 6 | 7 | 6 | 7 |
| 8 | 5 | 8 | 5 | 5 | 8 | 5 | 8 |
| 9 | 4 | 9 | 4 | 4 | 9 | 4 | 9 |
| 10 | 3 | 10 | 3 | 3 | 10 | 3 | 10 |
| 11 | 2 | 11 | 2 | 2 | 11 | 2 | 11 |
| 12 | 1 | 12 | 1 | 1 | 12 | 1 | 12 |
| 1 | 12 | 2 | 11 | 12 | 1 | 11 | 2 |
| 2 | 11 | 3 | 10 | 11 | 2 | 10 | 3 |
| 3 | 10 | 4 | 9 | 10 | 3 | 9 | 4 |
| 4 | 9 | 5 | 8 | 9 | 4 | 8 | 5 |
| 5 | 8 | 6 | 7 | 8 | 5 | 7 | 6 |
| 6 | 7 | 7 | 6 | 7 | 6 | 6 | 7 |
| 7 | 6 | 8 | 5 | 6 | 7 | 5 | 8 |
| 8 | 5 | 9 | 4 | 5 | 8 | 4 | 9 |
| 9 | 4 | 10 | 3 | 4 | 9 | 3 | 10 |
| 10 | 3 | 11 | 2 | 3 | 10 | 2 | 11 |
| 11 | 2 | 12 | 1 | 2 | 11 | 1 | 12 |
| 12 | 1 | 1 | 12 | 1 | 12 | 12 | 1 |
| 1 | 12 | 3 | 10 | 12 | 1 | 10 | 3 |
| 2 | 11 | 4 | 9 | 11 | 2 | 9 | 4 |
| 3 | 10 | 5 | 8 | 10 | 3 | 8 | 5 |
| 4 | 9 | 6 | 7 | 9 | 4 | 7 | 6 |
| 5 | 8 | 7 | 6 | 8 | 5 | 6 | 7 |
| 6 | 7 | 8 | 5 | 7 | 6 | 5 | 8 |
| 7 | 6 | 9 | 4 | 6 | 7 | 4 | 9 |
| 8 | 5 | 10 | 3 | 5 | 8 | 3 | 10 |
| 9 | 4 | 11 | 2 | 4 | 9 | 2 | 11 |
| 10 | 3 | 12 | 1 | 3 | 10 | 1 | 12 |
| 11 | 2 | 2 | 11 | 2 | 11 | 11 | 2 |
| 12 | 1 | 4 | 9 | 1 | 12 | 10 | 3 |
| 1 | 12 | 4 | 9 | 12 | 1 | 9 | 4 |
| 2 | 11 | 5 | 8 | 11 | 2 | 8 | 5 |
| 3 | 10 | 6 | 7 | 10 | 3 | 7 | 6 |

-continued

| | | | | | | | |
|---|---|---|---|---|---|---|---|
| 4 | 9 | 7 | 6 | 9 | 4 | 6 | 7 |
| 5 | 8 | 8 | 5 | 8 | 5 | 5 | 8 |
| 6 | 7 | 9 | 4 | 7 | 6 | 4 | 9 |
| 7 | 6 | 10 | 3 | 6 | 7 | 3 | 10 |
| 8 | 5 | 11 | 2 | 5 | 8 | 2 | 11 |
| 9 | 4 | 12 | 1 | 4 | 9 | 1 | 12 |
| 10 | 3 | 2 | 11 | 3 | 10 | 11 | 2 |
| 11 | 2 | 3 | 10 | 2 | 11 | 10 | 3 |
| 12 | 1 | 4 | 9 | 1 | 12 | 11 | 2 |
| 1 | 12 | 5 | 8 | 12 | 1 | 8 | 5 |
| 2 | 11 | 6 | 7 | 11 | 2 | 7 | 6 |
| 3 | 10 | 7 | 6 | 10 | 3 | 6 | 7 |
| 4 | 9 | 8 | 5 | 9 | 4 | 5 | 8 |
| 5 | 8 | 9 | 4 | 8 | 5 | 4 | 9 |
| 6 | 7 | 10 | 3 | 7 | 6 | 3 | 10 |
| 7 | 6 | 11 | 2 | 6 | 7 | 2 | 11 |
| 8 | 5 | 12 | 1 | 5 | 8 | 1 | 12 |
| 9 | 4 | 2 | 11 | 4 | 9 | 11 | 2 |
| 10 | 3 | 3 | 10 | 3 | 10 | 10 | 3 |
| 11 | 2 | 4 | 9 | 2 | 11 | 11 | 2 |
| 12 | 1 | 5 | 8 | 1 | 12 | 12 | 1 |
| 1 | 12 | 6 | 7 | 12 | 1 | 7 | 6 |
| 2 | 11 | 7 | 6 | 11 | 2 | 6 | 7 |
| 3 | 10 | 8 | 5 | 10 | 3 | 5 | 8 |
| 4 | 9 | 9 | 4 | 9 | 4 | 4 | 9 |
| 5 | 8 | 10 | 3 | 8 | 5 | 3 | 10 |
| 6 | 7 | 11 | 2 | 7 | 6 | 2 | 11 |
| 7 | 6 | 12 | 1 | 6 | 7 | 1 | 12 |
| 8 | 5 | 2 | 11 | 5 | 8 | 11 | 2 |
| 9 | 4 | 3 | 10 | 4 | 9 | 10 | 3 |
| 10 | 3 | 4 | 9 | 3 | 10 | 11 | 2 |
| 11 | 2 | 5 | 8 | 2 | 11 | 12 | 1 |
| 12 | 1 | 6 | 7 | 1 | 12 | 1 | 12 |
| 1 | 12 | 7 | 6 | 12 | 1 | 6 | 7 |
| 2 | 11 | 8 | 5 | 11 | 2 | 5 | 8 |
| 3 | 10 | 9 | 4 | 10 | 3 | 4 | 9 |
| 4 | 9 | 8 | 5 | 9 | 4 | 3 | 10 |
| 5 | 8 | 9 | 4 | 8 | 5 | 2 | 11 |
| 6 | 7 | 10 | 3 | 7 | 6 | 1 | 12 |
| 7 | 6 | 11 | 2 | 6 | 7 | 11 | 2 |
| 8 | 5 | 12 | 1 | 5 | 8 | 10 | 3 |
| 9 | 4 | 2 | 11 | 4 | 9 | 11 | 2 |
| 10 | 3 | 3 | 10 | 3 | 10 | 12 | 1 |
| 11 | 2 | 4 | 9 | 2 | 11 | 1 | 12 |
| 12 | 1 | 5 | 8 | 1 | 12 | 2 | 11 |

-continued
| 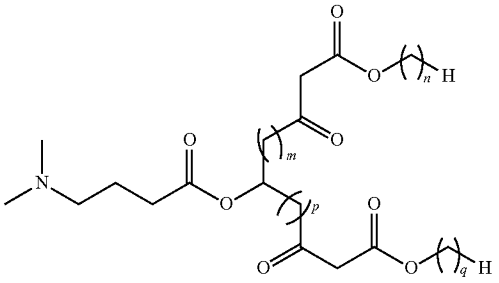 | | | | 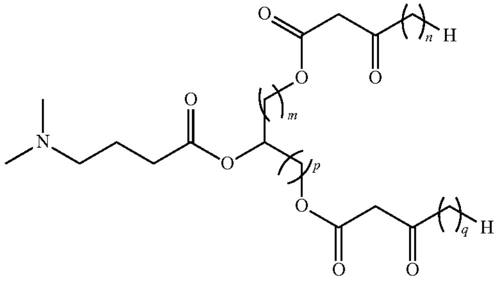 | | | |
|---|---|---|---|---|---|---|---|
| m | n | p | q | m | n | p | q |
| 1 | 13 | 1 | 13 | 1 | 13 | 1 | 13 |
| 2 | 12 | 2 | 12 | 2 | 12 | 2 | 12 |
| 3 | 11 | 3 | 11 | 3 | 11 | 3 | 11 |
| 4 | 10 | 4 | 10 | 4 | 10 | 4 | 10 |
| 5 | 9 | 5 | 9 | 5 | 9 | 5 | 9 |
| 6 | 8 | 6 | 8 | 6 | 8 | 6 | 8 |
| 7 | 7 | 7 | 7 | 7 | 7 | 7 | 7 |
| 8 | 6 | 8 | 6 | 8 | 6 | 8 | 6 |
| 9 | 5 | 9 | 5 | 9 | 5 | 9 | 5 |
| 10 | 4 | 10 | 4 | 10 | 4 | 10 | 4 |
| 11 | 3 | 11 | 3 | 11 | 3 | 11 | 3 |
| 12 | 2 | 12 | 2 | 12 | 2 | 12 | 2 |
| 13 | 1 | 13 | 1 | 13 | 1 | 13 | 1 |
| 1 | 13 | 2 | 12 | 1 | 13 | 2 | 12 |
| 2 | 12 | 3 | 11 | 2 | 12 | 3 | 11 |
| 3 | 11 | 4 | 10 | 3 | 11 | 4 | 10 |
| 4 | 10 | 5 | 9 | 4 | 10 | 5 | 9 |
| 5 | 9 | 6 | 8 | 5 | 9 | 6 | 8 |
| 6 | 8 | 7 | 7 | 6 | 8 | 7 | 7 |
| 7 | 7 | 8 | 6 | 7 | 7 | 8 | 6 |
| 8 | 6 | 9 | 5 | 8 | 6 | 9 | 5 |
| 9 | 5 | 10 | 4 | 9 | 5 | 10 | 4 |
| 10 | 4 | 11 | 3 | 10 | 4 | 11 | 3 |
| 11 | 3 | 12 | 2 | 11 | 3 | 12 | 2 |
| 12 | 2 | 13 | 1 | 12 | 2 | 13 | 1 |
| 13 | 1 | 1 | 13 | 13 | 1 | 1 | 13 |
| 1 | 13 | 3 | 11 | 1 | 13 | 3 | 11 |
| 2 | 12 | 4 | 10 | 2 | 12 | 4 | 10 |
| 3 | 11 | 5 | 9 | 3 | 11 | 5 | 9 |
| 4 | 10 | 6 | 8 | 4 | 10 | 6 | 8 |
| 5 | 9 | 7 | 7 | 5 | 9 | 7 | 7 |
| 6 | 8 | 8 | 6 | 6 | 8 | 8 | 6 |
| 7 | 7 | 9 | 5 | 7 | 7 | 9 | 5 |
| 8 | 6 | 10 | 4 | 8 | 6 | 10 | 4 |
| 9 | 5 | 11 | 3 | 9 | 5 | 11 | 3 |
| 10 | 4 | 12 | 2 | 10 | 4 | 12 | 2 |
| 11 | 3 | 13 | 1 | 11 | 3 | 13 | 1 |

-continued
| | | | | | | | |
|---|---|---|---|---|---|---|---|
| 12 | 2 | 1 | 13 | 12 | 2 | 1 | 13 |
| 13 | 1 | 2 | 12 | 13 | 1 | 2 | 14 |
| 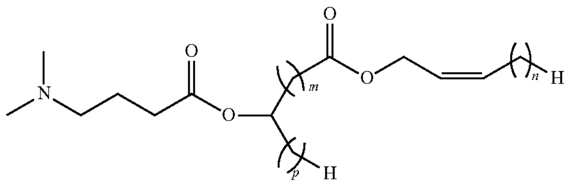 | | | 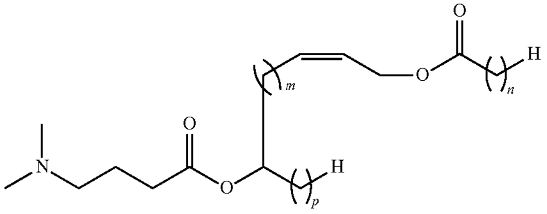 | | |
|---|---|---|---|---|---|
| m | n | p | m | n | p |
| 1 | 2 | 18 | 12 | 1 | 18 |
| 2 | 11 | 18 | 11 | 2 | 18 |
| 3 | 10 | 18 | 10 | 3 | 18 |
| 4 | 9 | 18 | 9 | 4 | 18 |
| 5 | 8 | 18 | 8 | 5 | 18 |
| 6 | 7 | 18 | 7 | 6 | 18 |
| 7 | 6 | 18 | 6 | 7 | 18 |
| 8 | 5 | 18 | 5 | 8 | 18 |
| 9 | 4 | 18 | 4 | 9 | 18 |
| 10 | 3 | 18 | 3 | 10 | 18 |
| 11 | 2 | 18 | 2 | 11 | 18 |
| 12 | 1 | 18 | 1 | 12 | 18 |
| 1 | 12 | 17 | 12 | 1 | 17 |
| 2 | 11 | 17 | 11 | 2 | 17 |
| 3 | 10 | 17 | 10 | 3 | 17 |
| 4 | 9 | 17 | 9 | 4 | 17 |
| 5 | 8 | 17 | 8 | 5 | 17 |
| 6 | 7 | 17 | 7 | 6 | 17 |
| 7 | 6 | 17 | 6 | 7 | 17 |
| 8 | 5 | 17 | 5 | 8 | 17 |
| 9 | 4 | 17 | 4 | 9 | 17 |
| 10 | 3 | 17 | 3 | 10 | 17 |
| 11 | 2 | 17 | 2 | 11 | 17 |
| 12 | 1 | 17 | 1 | 12 | 17 |
| 1 | 12 | 16 | 12 | 1 | 16 |
| 2 | 11 | 16 | 11 | 2 | 16 |
| 3 | 10 | 16 | 10 | 3 | 16 |
| 4 | 9 | 16 | 9 | 4 | 16 |
| 5 | 8 | 16 | 8 | 5 | 16 |
| 6 | 7 | 16 | 7 | 6 | 16 |
| 7 | 6 | 16 | 6 | 7 | 16 |
| 8 | 5 | 16 | 5 | 8 | 16 |
| 9 | 4 | 16 | 4 | 9 | 16 |
| 10 | 3 | 16 | 3 | 10 | 16 |
| 11 | 2 | 16 | 2 | 11 | 16 |
| 12 | 1 | 16 | 1 | 12 | 16 |
| 1 | 12 | 15 | 12 | 1 | 15 |

-continued

| | | | | | |
|---|---|---|---|---|---|
| 2 | 11 | 15 | 11 | 2 | 16 |
| 3 | 10 | 15 | 10 | 3 | 15 |
| 4 | 9 | 15 | 9 | 4 | 15 |
| 5 | 8 | 15 | 8 | 5 | 15 |
| 6 | 7 | 15 | 7 | 6 | 15 |
| 7 | 6 | 15 | 6 | 7 | 15 |
| 8 | 5 | 15 | 5 | 8 | 16 |
| 9 | 4 | 15 | 4 | 9 | 15 |
| 10 | 3 | 15 | 3 | 10 | 15 |
| 11 | 2 | 15 | 2 | 11 | 15 |
| 12 | 1 | 15 | 1 | 12 | 15 |
| 1 | 12 | 14 | 12 | 1 | 14 |
| 2 | 11 | 14 | 11 | 2 | 14 |
| 3 | 10 | 14 | 10 | 3 | 14 |
| 4 | 9 | 14 | 9 | 4 | 14 |
| 5 | 8 | 14 | 8 | 5 | 14 |
| 6 | 7 | 14 | 7 | 6 | 14 |
| 7 | 6 | 14 | 6 | 7 | 14 |
| 8 | 5 | 14 | 5 | 8 | 14 |
| 9 | 4 | 14 | 4 | 9 | 14 |
| 10 | 3 | 14 | 3 | 10 | 14 |
| 11 | 2 | 14 | 2 | 11 | 14 |
| 12 | 1 | 14 | 1 | 12 | 14 |
| 1 | 12 | 13 | 12 | 1 | 13 |
| 2 | 11 | 13 | 11 | 2 | 13 |
| 3 | 10 | 13 | 10 | 3 | 13 |
| 4 | 9 | 13 | 9 | 4 | 13 |
| 5 | 8 | 13 | 8 | 5 | 13 |
| 6 | 7 | 13 | 7 | 6 | 13 |
| 7 | 6 | 13 | 6 | 7 | 13 |
| 8 | 5 | 13 | 5 | 8 | 13 |
| 9 | 4 | 13 | 4 | 9 | 13 |
| 10 | 3 | 13 | 3 | 10 | 13 |
| 11 | 2 | 13 | 2 | 11 | 13 |
| 12 | 1 | 13 | 1 | 12 | 13 |
| 1 | 12 | 12 | 12 | 1 | 12 |
| 2 | 11 | 12 | 11 | 2 | 12 |
| 3 | 10 | 12 | 10 | 3 | 12 |
| 4 | 9 | 12 | 9 | 4 | 12 |
| 5 | 8 | 12 | 8 | 5 | 12 |
| 6 | 7 | 12 | 7 | 6 | 12 |
| 7 | 6 | 12 | 6 | 7 | 12 |
| 8 | 5 | 12 | 5 | 8 | 12 |
| 9 | 4 | 12 | 4 | 9 | 12 |
| 10 | 3 | 12 | 3 | 10 | 12 |
| 11 | 2 | 12 | 2 | 11 | 12 |
| 12 | 1 | 12 | 1 | 12 | 12 |
| 1 | 12 | 11 | 12 | 1 | 11 |
| 2 | 11 | 11 | 11 | 2 | 11 |
| 3 | 10 | 11 | 10 | 3 | 11 |
| 4 | 9 | 11 | 9 | 4 | 11 |
| 5 | 8 | 11 | 8 | 5 | 11 |
| 6 | 7 | 11 | 7 | 6 | 11 |

-continued

| | | | | | |
|---|---|---|---|---|---|
| 7 | 6 | 11 | 6 | 7 | 11 |
| 8 | 5 | 11 | 5 | 8 | 11 |
| 9 | 4 | 11 | 4 | 9 | 11 |
| 10 | 3 | 11 | 3 | 10 | 11 |
| 11 | 2 | 11 | 2 | 11 | 11 |
| 12 | 1 | 11 | 1 | 12 | 11 |
| 12 | 1 | 10 | 12 | 1 | 10 |
| 1 | 12 | 10 | 11 | 2 | 10 |
| 2 | 11 | 10 | 10 | 3 | 10 |
| 3 | 10 | 10 | 9 | 4 | 10 |
| 4 | 9 | 10 | 8 | 5 | 10 |
| 5 | 8 | 10 | 7 | 6 | 10 |
| 6 | 7 | 10 | 6 | 7 | 10 |
| 7 | 6 | 10 | 5 | 8 | 10 |
| 8 | 5 | 10 | 4 | 9 | 10 |
| 9 | 4 | 10 | 3 | 10 | 10 |
| 10 | 3 | 10 | 2 | 11 | 10 |
| 11 | 2 | 10 | 1 | 12 | 10 |
| 12 | 1 | 10 | 12 | 1 | 10 |
| 1 | 12 | 9 | 11 | 2 | 9 |
| 2 | 11 | 9 | 10 | 3 | 9 |
| 3 | 10 | 9 | 9 | 4 | 9 |
| 4 | 9 | 9 | 8 | 5 | 9 |
| 5 | 8 | 9 | 7 | 6 | 9 |
| 6 | 7 | 9 | 6 | 7 | 9 |
| 7 | 6 | 9 | 5 | 8 | 9 |
| 8 | 5 | 9 | 4 | 9 | 9 |
| 9 | 4 | 9 | 3 | 10 | 9 |
| 10 | 3 | 9 | 2 | 11 | 9 |
| 11 | 2 | 9 | 1 | 12 | 9 |
| 12 | 1 | 9 | 12 | 1 | 9 |
| 1 | 12 | 8 | 11 | 2 | 8 |
| 2 | 11 | 8 | 10 | 3 | 8 |
| 3 | 10 | 8 | 9 | 4 | 8 |
| 4 | 9 | 8 | 8 | 5 | 8 |
| 5 | 8 | 8 | 7 | 6 | 8 |
| 6 | 7 | 8 | 6 | 7 | 8 |
| 7 | 6 | 8 | 5 | 8 | 8 |
| 8 | 5 | 8 | 4 | 9 | 8 |
| 9 | 4 | 8 | 3 | 10 | 8 |
| 10 | 3 | 8 | 2 | 11 | 8 |
| 11 | 2 | 8 | 1 | 12 | 8 |
| 12 | 1 | 8 | 12 | 1 | 8 |

-continued
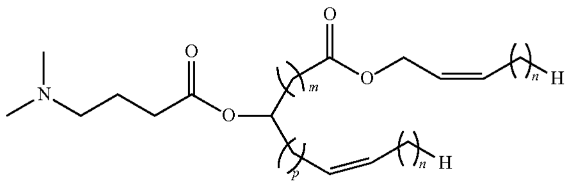 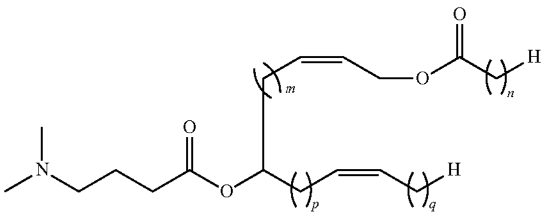
| m | n | p | q | m | n | p | q |
|---|---|---|---|---|---|---|---|
| 1 | 12 | 8 | 8 | 12 | 1 | 8 | 8 |
| 2 | 11 | 8 | 8 | 11 | 2 | 8 | 8 |
| 3 | 10 | 8 | 8 | 10 | 3 | 8 | 8 |
| 4 | 9 | 8 | 8 | 9 | 4 | 8 | 8 |
| 5 | 8 | 8 | 8 | 8 | 5 | 8 | 8 |
| 6 | 7 | 8 | 8 | 7 | 6 | 8 | 8 |
| 7 | 6 | 8 | 8 | 6 | 7 | 8 | 8 |
| 8 | 5 | 8 | 8 | 5 | 8 | 8 | 8 |
| 9 | 4 | 8 | 8 | 4 | 9 | 8 | 8 |
| 10 | 3 | 8 | 8 | 3 | 10 | 8 | 8 |
| 11 | 2 | 8 | 8 | 2 | 11 | 8 | 8 |
| 12 | 1 | 8 | 8 | 1 | 12 | 8 | 8 |
| 1 | 12 | 9 | 7 | 12 | 1 | 9 | 7 |
| 2 | 11 | 9 | 7 | 11 | 2 | 9 | 7 |
| 3 | 10 | 9 | 7 | 10 | 3 | 9 | 7 |
| 4 | 9 | 9 | 7 | 9 | 4 | 9 | 7 |
| 5 | 8 | 9 | 7 | 8 | 5 | 9 | 7 |
| 6 | 7 | 9 | 7 | 7 | 6 | 9 | 7 |
| 7 | 6 | 9 | 7 | 6 | 7 | 9 | 7 |
| 8 | 5 | 9 | 7 | 5 | 8 | 9 | 7 |
| 9 | 4 | 9 | 7 | 4 | 9 | 9 | 7 |
| 10 | 3 | 9 | 7 | 3 | 10 | 9 | 7 |
| 11 | 2 | 9 | 7 | 2 | 11 | 9 | 7 |
| 12 | 1 | 9 | 7 | 1 | 12 | 9 | 7 |
| 1 | 12 | 10 | 6 | 12 | 1 | 10 | 6 |
| 2 | 11 | 10 | 6 | 11 | 2 | 10 | 6 |
| 3 | 10 | 10 | 6 | 10 | 3 | 10 | 6 |
| 4 | 9 | 10 | 6 | 9 | 4 | 10 | 6 |
| 5 | 8 | 10 | 6 | 8 | 5 | 10 | 6 |
| 6 | 7 | 10 | 6 | 7 | 6 | 10 | 6 |
| 7 | 6 | 10 | 6 | 6 | 7 | 10 | 6 |
| 8 | 5 | 10 | 6 | 5 | 8 | 10 | 6 |
| 9 | 4 | 10 | 6 | 4 | 9 | 10 | 6 |
| 10 | 3 | 10 | 6 | 3 | 10 | 10 | 6 |
| 11 | 2 | 10 | 6 | 2 | 11 | 10 | 6 |
| 12 | 1 | 10 | 6 | 1 | 12 | 10 | 6 |
| 1 | 12 | 11 | 5 | 12 | 1 | 11 | 5 |
| 2 | 11 | 11 | 5 | 11 | 2 | 11 | 5 |
| 3 | 10 | 11 | 5 | 10 | 3 | 11 | 5 |
| 4 | 9 | 11 | 5 | 9 | 4 | 11 | 5 |

-continued

| | | | | | | | |
|---|---|---|---|---|---|---|---|
| 5 | 8 | 11 | 5 | 8 | 5 | 11 | 5 |
| 6 | 7 | 11 | 5 | 7 | 6 | 11 | 5 |
| 7 | 6 | 11 | 5 | 6 | 7 | 11 | 5 |
| 8 | 5 | 11 | 5 | 5 | 8 | 11 | 5 |
| 9 | 4 | 11 | 5 | 4 | 9 | 11 | 5 |
| 10 | 3 | 11 | 5 | 3 | 10 | 11 | 5 |
| 11 | 2 | 11 | 5 | 2 | 11 | 11 | 5 |
| 12 | 1 | 11 | 5 | 1 | 12 | 11 | 5 |
| 1 | 12 | 12 | 4 | 12 | 1 | 12 | 4 |
| 2 | 11 | 12 | 4 | 11 | 2 | 12 | 4 |
| 3 | 10 | 12 | 4 | 10 | 3 | 12 | 4 |
| 4 | 9 | 12 | 4 | 9 | 4 | 12 | 4 |
| 5 | 8 | 12 | 4 | 8 | 5 | 12 | 4 |
| 6 | 7 | 12 | 4 | 7 | 6 | 12 | 4 |
| 7 | 6 | 12 | 4 | 6 | 7 | 12 | 4 |
| 8 | 5 | 12 | 4 | 5 | 8 | 12 | 4 |
| 9 | 4 | 12 | 4 | 4 | 9 | 12 | 4 |
| 10 | 3 | 12 | 4 | 3 | 10 | 12 | 4 |
| 11 | 2 | 12 | 4 | 2 | 11 | 12 | 4 |
| 12 | 1 | 12 | 4 | 1 | 12 | 12 | 4 |
| 1 | 12 | 13 | 3 | 12 | 1 | 13 | 3 |
| 2 | 11 | 13 | 3 | 11 | 2 | 13 | 3 |
| 3 | 10 | 13 | 3 | 10 | 3 | 13 | 3 |
| 4 | 9 | 13 | 3 | 9 | 4 | 13 | 3 |
| 5 | 8 | 13 | 3 | 8 | 5 | 13 | 3 |
| 6 | 7 | 13 | 3 | 7 | 6 | 13 | 3 |
| 7 | 6 | 13 | 3 | 6 | 7 | 13 | 3 |
| 8 | 5 | 13 | 3 | 5 | 8 | 13 | 3 |
| 9 | 4 | 13 | 3 | 4 | 9 | 13 | 3 |
| 10 | 3 | 13 | 3 | 3 | 10 | 13 | 3 |
| 11 | 2 | 13 | 3 | 2 | 11 | 13 | 3 |
| 12 | 1 | 13 | 3 | 1 | 12 | 13 | 3 |
| 1 | 12 | 14 | 2 | 12 | 1 | 14 | 2 |
| 2 | 11 | 14 | 2 | 11 | 2 | 14 | 2 |
| 3 | 10 | 14 | 2 | 10 | 3 | 14 | 2 |
| 4 | 9 | 14 | 2 | 9 | 4 | 14 | 2 |
| 5 | 8 | 14 | 2 | 8 | 5 | 14 | 2 |
| 6 | 7 | 14 | 2 | 7 | 6 | 14 | 2 |
| 7 | 6 | 14 | 2 | 6 | 7 | 14 | 2 |
| 8 | 5 | 14 | 2 | 5 | 8 | 14 | 2 |
| 9 | 4 | 14 | 2 | 4 | 9 | 14 | 2 |
| 10 | 3 | 14 | 2 | 3 | 10 | 14 | 2 |
| 11 | 2 | 14 | 2 | 2 | 11 | 14 | 2 |
| 12 | 1 | 14 | 2 | 1 | 12 | 14 | 2 |
| 1 | 12 | 7 | 9 | 12 | 1 | 7 | 9 |
| 2 | 11 | 7 | 9 | 11 | 2 | 7 | 9 |
| 3 | 10 | 7 | 9 | 10 | 3 | 7 | 9 |
| 4 | 9 | 7 | 9 | 9 | 4 | 7 | 9 |
| 5 | 8 | 7 | 9 | 8 | 5 | 7 | 9 |
| 6 | 7 | 7 | 9 | 7 | 6 | 7 | 9 |
| 7 | 6 | 7 | 9 | 6 | 7 | 7 | 9 |
| 8 | 5 | 7 | 9 | 5 | 8 | 7 | 9 |
| 9 | 4 | 7 | 9 | 4 | 9 | 7 | 9 |

-continued
| | | | | | | | |
|---|---|---|---|---|---|---|---|
| 10 | 3 | 7 | 9 | 3 | 10 | 7 | 9 |
| 11 | 2 | 7 | 9 | 2 | 11 | 7 | 9 |
| 12 | 1 | 7 | 9 | 1 | 12 | 7 | 9 |
| 12 | 1 | 6 | 10 | 12 | 1 | 6 | 10 |
| 1 | 12 | 6 | 10 | 11 | 2 | 6 | 10 |
| 2 | 11 | 6 | 10 | 10 | 3 | 6 | 10 |
| 3 | 10 | 6 | 10 | 9 | 4 | 6 | 10 |
| 4 | 9 | 6 | 10 | 8 | 5 | 6 | 10 |
| 5 | 8 | 6 | 10 | 7 | 6 | 6 | 10 |
| 6 | 7 | 6 | 10 | 6 | 7 | 6 | 10 |
| 7 | 6 | 6 | 10 | 5 | 8 | 6 | 10 |
| 8 | 5 | 6 | 10 | 4 | 9 | 6 | 10 |
| 9 | 4 | 6 | 10 | 3 | 10 | 6 | 10 |
| 10 | 3 | 6 | 10 | 2 | 11 | 6 | 10 |
| 11 | 2 | 6 | 10 | 1 | 12 | 6 | 10 |
| 12 | 1 | 6 | 10 | 12 | 1 | 6 | 10 |
| 1 | 12 | 5 | 11 | 11 | 2 | 5 | 11 |
| 2 | 11 | 5 | 11 | 10 | 3 | 5 | 11 |
| 3 | 10 | 5 | 11 | 9 | 4 | 5 | 11 |
| 4 | 9 | 5 | 11 | 8 | 5 | 5 | 11 |
| 5 | 8 | 5 | 11 | 7 | 6 | 6 | 11 |
| 6 | 7 | 5 | 11 | 6 | 7 | 5 | 11 |
| 7 | 6 | 5 | 11 | 5 | 8 | 5 | 11 |
| 8 | 5 | 5 | 11 | 4 | 9 | 5 | 11 |
| 9 | 4 | 5 | 11 | 3 | 10 | 5 | 11 |
| 10 | 3 | 5 | 11 | 2 | 11 | 5 | 11 |
| 11 | 2 | 5 | 11 | 1 | 12 | 5 | 11 |
| 12 | 1 | 5 | 11 | 12 | 1 | 5 | 11 |
| 1 | 12 | 4 | 12 | 11 | 2 | 4 | 12 |
| 2 | 11 | 4 | 12 | 10 | 3 | 4 | 12 |
| 3 | 10 | 4 | 12 | 9 | 4 | 4 | 12 |
| 4 | 9 | 4 | 12 | 8 | 5 | 4 | 12 |
| 5 | 8 | 4 | 12 | 7 | 6 | 4 | 12 |
| 6 | 7 | 4 | 12 | 6 | 7 | 4 | 12 |
| 7 | 6 | 4 | 12 | 5 | 8 | 4 | 12 |
| 8 | 5 | 4 | 12 | 4 | 9 | 4 | 12 |
| 9 | 4 | 4 | 12 | 3 | 10 | 4 | 12 |
| 10 | 3 | 4 | 12 | 2 | 11 | 4 | 12 |
| 11 | 2 | 4 | 12 | 1 | 12 | 4 | 12 |
| 12 | 1 | 4 | 12 | 12 | 1 | 4 | 12 |
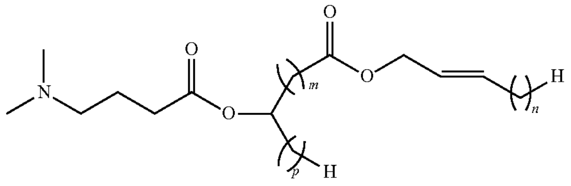
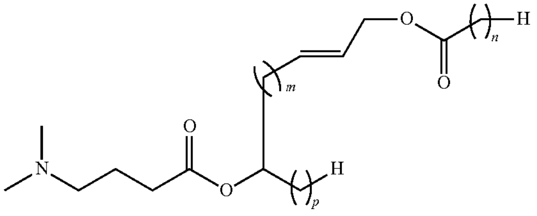
m n p m n p -continued

| | | | | | |
|---|---|---|---|---|---|
| 1 | 12 | 18 | 12 | 1 | 18 |
| 2 | 11 | 18 | 11 | 2 | 18 |
| 3 | 10 | 18 | 10 | 3 | 18 |
| 4 | 9 | 18 | 9 | 4 | 18 |
| 5 | 8 | 18 | 8 | 5 | 18 |
| 6 | 7 | 18 | 7 | 6 | 18 |
| 7 | 6 | 18 | 6 | 7 | 18 |
| 8 | 5 | 18 | 5 | 8 | 18 |
| 9 | 4 | 18 | 4 | 9 | 18 |
| 10 | 3 | 18 | 3 | 10 | 18 |
| 11 | 2 | 18 | 2 | 11 | 18 |
| 12 | 1 | 18 | 1 | 12 | 18 |
| 1 | 12 | 17 | 12 | 1 | 17 |
| 2 | 11 | 17 | 11 | 2 | 17 |
| 3 | 10 | 17 | 10 | 3 | 17 |
| 4 | 9 | 17 | 9 | 4 | 17 |
| 5 | 8 | 17 | 8 | 5 | 17 |
| 6 | 7 | 17 | 7 | 6 | 17 |
| 7 | 6 | 17 | 6 | 7 | 17 |
| 8 | 5 | 17 | 5 | 8 | 17 |
| 9 | 4 | 17 | 4 | 9 | 17 |
| 10 | 3 | 17 | 3 | 10 | 17 |
| 11 | 2 | 17 | 2 | 11 | 17 |
| 12 | 1 | 17 | 1 | 12 | 17 |
| 1 | 12 | 16 | 12 | 1 | 16 |
| 2 | 11 | 16 | 11 | 2 | 16 |
| 3 | 10 | 16 | 10 | 3 | 16 |
| 4 | 9 | 16 | 9 | 4 | 16 |
| 5 | 8 | 16 | 8 | 5 | 16 |
| 6 | 7 | 16 | 7 | 6 | 16 |
| 7 | 6 | 16 | 6 | 7 | 16 |
| 8 | 5 | 16 | 5 | 8 | 16 |
| 9 | 4 | 16 | 4 | 9 | 16 |
| 10 | 3 | 16 | 3 | 10 | 16 |
| 11 | 2 | 16 | 2 | 11 | 16 |
| 12 | 1 | 16 | 1 | 12 | 16 |
| 1 | 12 | 15 | 12 | 1 | 15 |
| 2 | 11 | 15 | 11 | 2 | 15 |
| 3 | 10 | 15 | 10 | 3 | 15 |
| 4 | 9 | 15 | 9 | 4 | 15 |
| 5 | 8 | 15 | 8 | 5 | 15 |
| 6 | 7 | 15 | 7 | 6 | 15 |
| 7 | 6 | 15 | 6 | 7 | 15 |
| 8 | 5 | 15 | 5 | 8 | 15 |
| 9 | 4 | 15 | 4 | 9 | 15 |
| 10 | 3 | 15 | 3 | 10 | 15 |
| 11 | 2 | 15 | 2 | 11 | 15 |
| 12 | 1 | 15 | 1 | 12 | 15 |
| 1 | 12 | 14 | 12 | 1 | 14 |
| 2 | 11 | 14 | 11 | 2 | 14 |
| 3 | 10 | 14 | 10 | 3 | 14 |
| 4 | 9 | 14 | 9 | 4 | 14 |

-continued

| | | | | | |
|---|---|---|---|---|---|
| 5 | 8 | 14 | 8 | 5 | 14 |
| 6 | 7 | 14 | 7 | 6 | 14 |
| 7 | 6 | 14 | 6 | 7 | 14 |
| 8 | 5 | 14 | 5 | 8 | 14 |
| 9 | 4 | 14 | 4 | 9 | 14 |
| 10 | 3 | 14 | 3 | 10 | 14 |
| 11 | 2 | 14 | 2 | 11 | 14 |
| 12 | 1 | 14 | 1 | 12 | 14 |
| 1 | 12 | 13 | 12 | 1 | 13 |
| 2 | 11 | 13 | 11 | 2 | 13 |
| 3 | 10 | 13 | 10 | 3 | 13 |
| 4 | 9 | 13 | 9 | 4 | 13 |
| 5 | 8 | 13 | 8 | 5 | 13 |
| 6 | 7 | 13 | 7 | 6 | 13 |
| 7 | 6 | 13 | 6 | 7 | 13 |
| 8 | 5 | 13 | 5 | 8 | 13 |
| 9 | 4 | 13 | 4 | 9 | 13 |
| 10 | 3 | 13 | 3 | 10 | 13 |
| 11 | 2 | 13 | 2 | 11 | 13 |
| 12 | 1 | 13 | 1 | 12 | 13 |
| 1 | 12 | 12 | 12 | 1 | 12 |
| 2 | 11 | 12 | 11 | 2 | 12 |
| 3 | 10 | 12 | 10 | 3 | 12 |
| 4 | 9 | 12 | 9 | 4 | 12 |
| 5 | 8 | 12 | 8 | 5 | 12 |
| 6 | 7 | 12 | 7 | 6 | 12 |
| 7 | 6 | 12 | 6 | 7 | 12 |
| 8 | 5 | 12 | 5 | 8 | 12 |
| 9 | 4 | 12 | 4 | 9 | 12 |
| 10 | 3 | 12 | 3 | 10 | 12 |
| 11 | 2 | 12 | 2 | 11 | 12 |
| 12 | 1 | 12 | 1 | 12 | 12 |
| 1 | 12 | 11 | 12 | 1 | 11 |
| 2 | 11 | 11 | 11 | 2 | 11 |
| 3 | 10 | 11 | 10 | 3 | 11 |
| 4 | 9 | 11 | 9 | 4 | 11 |
| 5 | 8 | 11 | 8 | 5 | 11 |
| 6 | 7 | 11 | 7 | 6 | 11 |
| 7 | 6 | 11 | 6 | 7 | 11 |
| 8 | 5 | 11 | 5 | 8 | 11 |
| 9 | 4 | 11 | 4 | 9 | 11 |
| 10 | 3 | 11 | 3 | 10 | 11 |
| 11 | 2 | 11 | 2 | 11 | 11 |
| 12 | 1 | 11 | 1 | 12 | 11 |
| 12 | 1 | 10 | 12 | 1 | 10 |
| 1 | 12 | 10 | 11 | 2 | 10 |
| 2 | 11 | 10 | 10 | 3 | 10 |
| 3 | 10 | 10 | 9 | 4 | 10 |
| 4 | 9 | 10 | 8 | 5 | 10 |
| 5 | 8 | 10 | 7 | 6 | 10 |
| 6 | 7 | 10 | 6 | 7 | 10 |
| 7 | 6 | 10 | 5 | 8 | 10 |
| 8 | 5 | 10 | 4 | 9 | 10 |

-continued
| | | | | | |
|---|---|---|---|---|---|
| 9 | 4 | 10 | 3 | 10 | 10 |
| 10 | 3 | 10 | 2 | 11 | 10 |
| 11 | 2 | 10 | 1 | 12 | 10 |
| 12 | 1 | 10 | 12 | 1 | 10 |
| 1 | 12 | 9 | 11 | 2 | 9 |
| 2 | 11 | 9 | 10 | 3 | 9 |
| 3 | 10 | 9 | 9 | 4 | 9 |
| 4 | 9 | 9 | 8 | 5 | 9 |
| 5 | 8 | 9 | 7 | 6 | 9 |
| 6 | 7 | 9 | 6 | 7 | 9 |
| 7 | 6 | 9 | 5 | 8 | 9 |
| 8 | 5 | 9 | 4 | 9 | 9 |
| 9 | 4 | 9 | 3 | 10 | 9 |
| 10 | 3 | 9 | 2 | 11 | 9 |
| 11 | 2 | 9 | 1 | 12 | 9 |
| 12 | 1 | 9 | 12 | 1 | 9 |
| 1 | 12 | 8 | 11 | 2 | 8 |
| 2 | 11 | 8 | 10 | 3 | 8 |
| 3 | 10 | 8 | 9 | 4 | 8 |
| 4 | 9 | 8 | 8 | 5 | 8 |
| 5 | 8 | 8 | 7 | 6 | 8 |
| 6 | 7 | 8 | 6 | 7 | 8 |
| 7 | 6 | 8 | 5 | 8 | 8 |
| 8 | 5 | 8 | 4 | 9 | 8 |
| 9 | 4 | 8 | 3 | 10 | 8 |
| 10 | 3 | 8 | 2 | 11 | 8 |
| 11 | 2 | 8 | 1 | 12 | 8 |
| 12 | 1 | 8 | 12 | 1 | 8 |
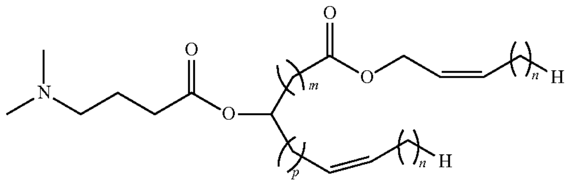
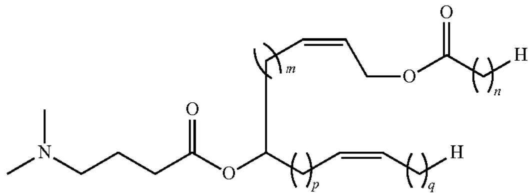
| m | n | p | q | m | n | p | q |
|---|---|---|---|---|---|---|---|
| 1 | 12 | 8 | 8 | 12 | 1 | 8 | 8 |
| 2 | 11 | 8 | 8 | 11 | 2 | 8 | 8 |
| 3 | 10 | 8 | 8 | 10 | 3 | 8 | 8 |
| 4 | 9 | 8 | 8 | 9 | 4 | 8 | 8 |
| 5 | 8 | 8 | 8 | 8 | 5 | 8 | 8 |
| 6 | 7 | 8 | 8 | 7 | 6 | 8 | 8 |
| 7 | 6 | 8 | 8 | 6 | 7 | 8 | 8 |
| 8 | 5 | 8 | 8 | 5 | 8 | 8 | 8 |
| 9 | 4 | 8 | 8 | 4 | 9 | 8 | 8 |
| 10 | 3 | 8 | 8 | 3 | 10 | 8 | 8 |
| 11 | 2 | 8 | 8 | 2 | 11 | 8 | 8 |
| 12 | 1 | 8 | 8 | 1 | 12 | 8 | 8 |

-continued

| | | | | | | | |
|---|---|---|---|---|---|---|---|
| 1 | 12 | 9 | 7 | 12 | 1 | 9 | 7 |
| 2 | 11 | 9 | 7 | 11 | 2 | 9 | 7 |
| 3 | 10 | 9 | 7 | 10 | 3 | 9 | 7 |
| 4 | 9 | 9 | 7 | 9 | 4 | 9 | 7 |
| 5 | 8 | 9 | 7 | 8 | 5 | 9 | 7 |
| 6 | 7 | 9 | 7 | 7 | 6 | 9 | 7 |
| 7 | 6 | 9 | 7 | 6 | 7 | 9 | 7 |
| 8 | 5 | 9 | 7 | 5 | 8 | 9 | 7 |
| 9 | 4 | 9 | 7 | 4 | 9 | 9 | 7 |
| 10 | 3 | 9 | 7 | 3 | 10 | 9 | 7 |
| 11 | 2 | 9 | 7 | 2 | 11 | 9 | 7 |
| 12 | 1 | 9 | 7 | 1 | 12 | 9 | 7 |
| 1 | 12 | 10 | 6 | 12 | 1 | 10 | 6 |
| 2 | 11 | 10 | 6 | 11 | 2 | 10 | 6 |
| 3 | 10 | 10 | 6 | 10 | 3 | 10 | 6 |
| 4 | 9 | 10 | 6 | 9 | 4 | 10 | 6 |
| 5 | 8 | 10 | 6 | 8 | 5 | 10 | 6 |
| 6 | 7 | 10 | 6 | 7 | 6 | 10 | 6 |
| 7 | 6 | 10 | 6 | 6 | 7 | 10 | 6 |
| 8 | 5 | 10 | 6 | 5 | 8 | 10 | 6 |
| 9 | 4 | 10 | 6 | 4 | 9 | 10 | 6 |
| 10 | 3 | 10 | 6 | 3 | 10 | 10 | 6 |
| 11 | 2 | 10 | 6 | 2 | 11 | 10 | 6 |
| 12 | 1 | 10 | 6 | 1 | 12 | 10 | 6 |
| 1 | 12 | 11 | 5 | 12 | 1 | 11 | 5 |
| 2 | 11 | 11 | 5 | 11 | 2 | 11 | 5 |
| 3 | 10 | 11 | 5 | 10 | 3 | 11 | 5 |
| 4 | 9 | 11 | 5 | 9 | 4 | 11 | 5 |
| 5 | 8 | 11 | 5 | 8 | 5 | 11 | 5 |
| 6 | 7 | 11 | 5 | 7 | 6 | 11 | 5 |
| 7 | 6 | 11 | 5 | 6 | 7 | 11 | 5 |
| 8 | 5 | 11 | 5 | 5 | 8 | 11 | 5 |
| 9 | 4 | 11 | 5 | 4 | 9 | 11 | 5 |
| 10 | 3 | 11 | 5 | 3 | 10 | 11 | 5 |
| 11 | 2 | 11 | 5 | 2 | 11 | 11 | 5 |
| 12 | 1 | 11 | 5 | 1 | 12 | 11 | 5 |
| 1 | 12 | 12 | 4 | 12 | 1 | 12 | 4 |
| 2 | 11 | 12 | 4 | 11 | 2 | 12 | 4 |
| 3 | 10 | 12 | 4 | 10 | 3 | 12 | 4 |
| 4 | 9 | 12 | 4 | 9 | 4 | 12 | 4 |
| 5 | 8 | 12 | 4 | 8 | 5 | 12 | 4 |
| 6 | 7 | 12 | 4 | 7 | 6 | 12 | 4 |
| 7 | 6 | 12 | 4 | 6 | 7 | 12 | 4 |
| 8 | 5 | 12 | 4 | 5 | 8 | 12 | 4 |
| 9 | 4 | 12 | 4 | 4 | 9 | 12 | 4 |
| 10 | 3 | 12 | 4 | 3 | 10 | 12 | 4 |
| 11 | 2 | 12 | 4 | 2 | 11 | 12 | 4 |
| 12 | 1 | 12 | 4 | 1 | 12 | 12 | 4 |
| 1 | 12 | 13 | 3 | 12 | 1 | 13 | 3 |
| 2 | 11 | 13 | 3 | 11 | 2 | 13 | 3 |
| 3 | 10 | 13 | 3 | 10 | 3 | 13 | 3 |
| 4 | 9 | 13 | 3 | 9 | 4 | 13 | 3 |
| 5 | 8 | 13 | 3 | 8 | 5 | 13 | 3 |

-continued

| | | | | | | | |
|---|---|---|---|---|---|---|---|
| 6 | 7 | 13 | 3 | 7 | 6 | 13 | 3 |
| 7 | 6 | 13 | 3 | 6 | 7 | 13 | 3 |
| 8 | 5 | 13 | 3 | 5 | 8 | 13 | 3 |
| 9 | 4 | 13 | 3 | 4 | 9 | 13 | 3 |
| 10 | 3 | 13 | 3 | 3 | 10 | 13 | 3 |
| 11 | 2 | 13 | 3 | 2 | 11 | 13 | 3 |
| 12 | 1 | 13 | 3 | 1 | 12 | 13 | 3 |
| 1 | 12 | 14 | 2 | 12 | 1 | 14 | 2 |
| 2 | 11 | 14 | 2 | 11 | 2 | 14 | 2 |
| 3 | 10 | 14 | 2 | 10 | 3 | 14 | 2 |
| 4 | 9 | 14 | 2 | 9 | 4 | 14 | 2 |
| 5 | 8 | 14 | 2 | 8 | 5 | 14 | 2 |
| 6 | 7 | 14 | 2 | 7 | 6 | 14 | 2 |
| 7 | 6 | 14 | 2 | 6 | 7 | 14 | 2 |
| 8 | 5 | 14 | 2 | 5 | 8 | 14 | 2 |
| 9 | 4 | 14 | 2 | 4 | 9 | 14 | 2 |
| 10 | 3 | 14 | 2 | 3 | 10 | 14 | 2 |
| 11 | 2 | 14 | 2 | 2 | 11 | 14 | 2 |
| 12 | 1 | 14 | 2 | 1 | 12 | 14 | 2 |
| 1 | 12 | 7 | 9 | 12 | 1 | 7 | 9 |
| 2 | 11 | 7 | 9 | 11 | 2 | 7 | 9 |
| 3 | 10 | 7 | 9 | 10 | 3 | 7 | 9 |
| 4 | 9 | 7 | 9 | 9 | 4 | 7 | 9 |
| 5 | 8 | 7 | 9 | 8 | 5 | 7 | 9 |
| 6 | 7 | 7 | 9 | 7 | 6 | 7 | 9 |
| 7 | 6 | 7 | 9 | 6 | 7 | 7 | 9 |
| 8 | 5 | 7 | 9 | 5 | 8 | 7 | 9 |
| 9 | 4 | 7 | 9 | 4 | 9 | 7 | 9 |
| 10 | 3 | 7 | 9 | 3 | 10 | 7 | 9 |
| 11 | 2 | 7 | 9 | 2 | 11 | 7 | 9 |
| 12 | 1 | 7 | 9 | 1 | 12 | 7 | 9 |
| 12 | 1 | 6 | 10 | 12 | 1 | 6 | 10 |
| 1 | 12 | 6 | 10 | 11 | 2 | 6 | 10 |
| 2 | 11 | 6 | 10 | 10 | 3 | 6 | 10 |
| 3 | 10 | 6 | 10 | 9 | 4 | 6 | 10 |
| 4 | 9 | 6 | 10 | 8 | 5 | 6 | 10 |
| 5 | 8 | 6 | 10 | 7 | 6 | 6 | 10 |
| 6 | 7 | 6 | 10 | 6 | 7 | 6 | 10 |
| 7 | 6 | 6 | 10 | 5 | 8 | 6 | 10 |
| 8 | 5 | 6 | 10 | 4 | 9 | 6 | 10 |
| 9 | 4 | 6 | 10 | 3 | 10 | 6 | 10 |
| 10 | 3 | 6 | 10 | 2 | 11 | 6 | 10 |
| 11 | 2 | 6 | 10 | 1 | 12 | 6 | 10 |
| 12 | 1 | 6 | 10 | 12 | 1 | 6 | 10 |
| 1 | 12 | 5 | 11 | 11 | 2 | 5 | 11 |
| 2 | 11 | 5 | 11 | 10 | 3 | 5 | 11 |
| 3 | 10 | 5 | 11 | 9 | 4 | 5 | 11 |
| 4 | 9 | 5 | 11 | 8 | 5 | 5 | 11 |
| 5 | 8 | 5 | 11 | 7 | 6 | 5 | 11 |
| 6 | 7 | 5 | 11 | 6 | 7 | 5 | 11 |
| 7 | 6 | 5 | 11 | 5 | 8 | 5 | 11 |
| 8 | 5 | 5 | 11 | 4 | 9 | 5 | 11 |
| 9 | 4 | 5 | 11 | 3 | 10 | 5 | 11 |

-continued
| | | | | | | | |
|---|---|---|---|---|---|---|---|
| 10 | 3 | 5 | 11 | 2 | 11 | 5 | 11 |
| 11 | 2 | 5 | 11 | 1 | 12 | 5 | 11 |
| 12 | 1 | 5 | 11 | 12 | 1 | 5 | 11 |
| 1 | 12 | 4 | 12 | 11 | 2 | 4 | 12 |
| 2 | 11 | 4 | 12 | 10 | 3 | 4 | 12 |
| 3 | 10 | 4 | 12 | 9 | 4 | 4 | 12 |
| 4 | 9 | 4 | 12 | 8 | 5 | 4 | 12 |
| 5 | 8 | 4 | 12 | 7 | 6 | 4 | 12 |
| 6 | 7 | 4 | 12 | 6 | 7 | 4 | 12 |
| 7 | 6 | 4 | 12 | 5 | 8 | 4 | 12 |
| 8 | 5 | 4 | 12 | 4 | 9 | 4 | 12 |
| 9 | 4 | 4 | 12 | 3 | 10 | 4 | 12 |
| 10 | 3 | 4 | 12 | 2 | 11 | 4 | 12 |
| 11 | 2 | 4 | 12 | 1 | 12 | 4 | 12 |
| 12 | 1 | 4 | 12 | 12 | 1 | 4 | 12 |
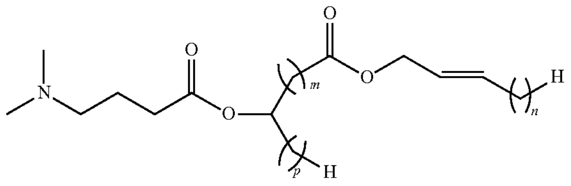
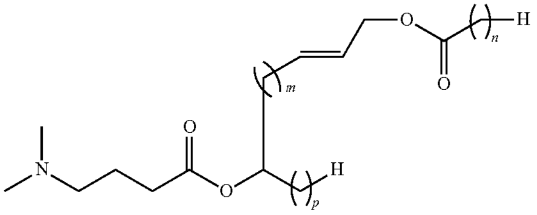
| m | n | p | m | n | p |
|---|---|---|---|---|---|
| 1 | 12 | 18 | 12 | 1 | 18 |
| 2 | 11 | 18 | 11 | 2 | 18 |
| 3 | 10 | 18 | 10 | 3 | 18 |
| 4 | 9 | 18 | 9 | 4 | 18 |
| 5 | 8 | 18 | 8 | 5 | 18 |
| 6 | 7 | 18 | 7 | 6 | 18 |
| 7 | 6 | 18 | 6 | 7 | 18 |
| 8 | 5 | 18 | 5 | 8 | 18 |
| 9 | 4 | 18 | 4 | 9 | 18 |
| 10 | 3 | 18 | 3 | 10 | 18 |
| 11 | 2 | 18 | 2 | 11 | 18 |
| 12 | 1 | 18 | 1 | 12 | 18 |
| 1 | 12 | 17 | 12 | 1 | 17 |
| 2 | 11 | 17 | 11 | 2 | 17 |
| 3 | 10 | 17 | 10 | 3 | 17 |
| 4 | 9 | 17 | 9 | 4 | 17 |
| 5 | 8 | 17 | 8 | 5 | 17 |
| 6 | 7 | 17 | 7 | 6 | 17 |
| 7 | 6 | 17 | 6 | 7 | 17 |
| 8 | 5 | 17 | 5 | 8 | 17 |
| 9 | 4 | 17 | 4 | 9 | 17 |
| 10 | 3 | 17 | 3 | 10 | 17 |
| 11 | 2 | 17 | 2 | 11 | 17 |
| 12 | 1 | 17 | 1 | 12 | 17 |

-continued

| | | | | | |
|---|---|---|---|---|---|
| 1 | 12 | 16 | 12 | 1 | 16 |
| 2 | 11 | 16 | 11 | 2 | 16 |
| 3 | 10 | 16 | 10 | 3 | 16 |
| 4 | 9 | 16 | 9 | 4 | 16 |
| 5 | 8 | 16 | 8 | 5 | 16 |
| 6 | 7 | 16 | 7 | 6 | 16 |
| 7 | 6 | 16 | 6 | 7 | 16 |
| 8 | 5 | 16 | 5 | 8 | 16 |
| 9 | 4 | 16 | 4 | 9 | 16 |
| 10 | 3 | 16 | 3 | 10 | 16 |
| 11 | 2 | 16 | 2 | 11 | 16 |
| 12 | 1 | 16 | 1 | 12 | 16 |
| 1 | 12 | 15 | 12 | 1 | 15 |
| 2 | 11 | 15 | 11 | 2 | 15 |
| 3 | 10 | 15 | 10 | 3 | 15 |
| 4 | 9 | 15 | 9 | 4 | 15 |
| 5 | 8 | 15 | 8 | 5 | 15 |
| 6 | 7 | 15 | 7 | 6 | 15 |
| 7 | 6 | 15 | 6 | 7 | 15 |
| 8 | 5 | 15 | 5 | 8 | 15 |
| 9 | 4 | 15 | 4 | 9 | 15 |
| 10 | 3 | 15 | 3 | 10 | 15 |
| 11 | 2 | 15 | 2 | 11 | 15 |
| 12 | 1 | 15 | 1 | 12 | 15 |
| 1 | 12 | 14 | 12 | 1 | 14 |
| 2 | 11 | 14 | 11 | 2 | 14 |
| 3 | 10 | 14 | 10 | 3 | 14 |
| 4 | 9 | 14 | 9 | 4 | 14 |
| 5 | 8 | 14 | 8 | 5 | 14 |
| 6 | 7 | 14 | 7 | 6 | 14 |
| 7 | 6 | 14 | 6 | 7 | 14 |
| 8 | 5 | 14 | 5 | 8 | 14 |
| 9 | 4 | 14 | 4 | 9 | 14 |
| 10 | 3 | 14 | 3 | 10 | 14 |
| 11 | 2 | 14 | 2 | 11 | 14 |
| 12 | 1 | 14 | 1 | 12 | 14 |
| 1 | 12 | 13 | 12 | 1 | 13 |
| 2 | 11 | 13 | 11 | 2 | 13 |
| 3 | 10 | 13 | 10 | 3 | 13 |
| 4 | 9 | 13 | 9 | 4 | 13 |
| 5 | 8 | 13 | 8 | 5 | 13 |
| 6 | 7 | 13 | 7 | 6 | 13 |
| 7 | 6 | 13 | 6 | 7 | 13 |
| 8 | 5 | 13 | 5 | 8 | 13 |
| 9 | 4 | 13 | 4 | 9 | 13 |
| 10 | 3 | 13 | 3 | 10 | 13 |
| 11 | 2 | 13 | 2 | 11 | 13 |
| 12 | 1 | 13 | 1 | 12 | 13 |
| 1 | 12 | 12 | 12 | 1 | 12 |
| 2 | 11 | 12 | 11 | 2 | 12 |
| 3 | 10 | 12 | 10 | 3 | 12 |
| 4 | 9 | 12 | 9 | 4 | 12 |
| 5 | 8 | 12 | 8 | 5 | 12 |

-continued

| | | | | | |
|---|---|---|---|---|---|
| 6 | 7 | 12 | 7 | 6 | 12 |
| 7 | 6 | 12 | 6 | 7 | 12 |
| 8 | 5 | 12 | 5 | 8 | 12 |
| 9 | 4 | 12 | 4 | 9 | 12 |
| 10 | 3 | 12 | 3 | 10 | 12 |
| 11 | 2 | 12 | 2 | 11 | 12 |
| 12 | 1 | 12 | 1 | 12 | 12 |
| 1 | 12 | 11 | 12 | 1 | 11 |
| 2 | 11 | 11 | 11 | 2 | 11 |
| 3 | 10 | 11 | 10 | 3 | 11 |
| 4 | 9 | 11 | 9 | 4 | 11 |
| 5 | 8 | 11 | 8 | 5 | 11 |
| 6 | 7 | 11 | 7 | 6 | 11 |
| 7 | 6 | 11 | 6 | 7 | 11 |
| 8 | 5 | 11 | 5 | 8 | 11 |
| 9 | 4 | 11 | 4 | 9 | 11 |
| 10 | 3 | 11 | 3 | 10 | 11 |
| 11 | 2 | 11 | 2 | 11 | 11 |
| 12 | 1 | 11 | 1 | 12 | 11 |
| 12 | 1 | 10 | 12 | 1 | 10 |
| 1 | 12 | 10 | 11 | 2 | 10 |
| 2 | 11 | 10 | 10 | 3 | 10 |
| 3 | 10 | 10 | 9 | 4 | 10 |
| 4 | 9 | 10 | 8 | 5 | 10 |
| 5 | 8 | 10 | 7 | 6 | 10 |
| 6 | 7 | 10 | 6 | 7 | 10 |
| 7 | 6 | 10 | 5 | 8 | 10 |
| 8 | 5 | 10 | 4 | 9 | 10 |
| 9 | 4 | 10 | 3 | 10 | 10 |
| 10 | 3 | 10 | 2 | 11 | 10 |
| 11 | 2 | 10 | 1 | 12 | 10 |
| 12 | 1 | 10 | 12 | 1 | 10 |
| 1 | 12 | 9 | 11 | 2 | 9 |
| 2 | 11 | 9 | 10 | 3 | 9 |
| 3 | 10 | 9 | 9 | 4 | 9 |
| 4 | 9 | 9 | 8 | 5 | 9 |
| 5 | 8 | 9 | 7 | 6 | 9 |
| 6 | 7 | 9 | 6 | 7 | 9 |
| 7 | 6 | 9 | 5 | 8 | 9 |
| 8 | 5 | 9 | 4 | 9 | 9 |
| 9 | 4 | 9 | 3 | 10 | 9 |
| 10 | 3 | 9 | 2 | 11 | 9 |
| 11 | 2 | 9 | 1 | 12 | 9 |
| 12 | 1 | 9 | 12 | 1 | 9 |
| 1 | 12 | 8 | 11 | 2 | 8 |
| 2 | 11 | 8 | 10 | 3 | 8 |
| 3 | 10 | 8 | 9 | 4 | 8 |
| 4 | 9 | 8 | 8 | 5 | 8 |
| 5 | 8 | 8 | 7 | 6 | 8 |
| 6 | 7 | 8 | 6 | 7 | 8 |
| 7 | 6 | 8 | 5 | 8 | 8 |
| 8 | 5 | 8 | 4 | 9 | 8 |
| 9 | 4 | 8 | 3 | 10 | 8 |

-continued
| | | | | | |
|---|---|---|---|---|---|
| 10 | 3 | 8 | 2 | 11 | 8 |
| 11 | 2 | 8 | 1 | 12 | 8 |
| 12 | 1 | 8 | 12 | 1 | 8 |
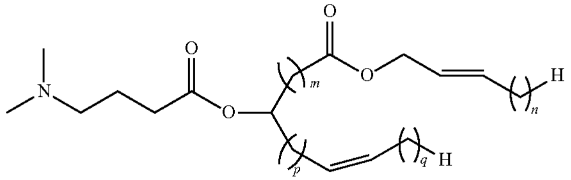
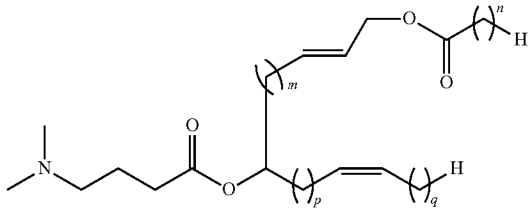
| m | n | p | q | m | n | p | q |
|---|---|---|---|---|---|---|---|
| 1 | 12 | 8 | 8 | 12 | 1 | 8 | 8 |
| 2 | 11 | 8 | 8 | 11 | 2 | 8 | 8 |
| 3 | 10 | 8 | 8 | 10 | 3 | 8 | 8 |
| 4 | 9 | 8 | 8 | 9 | 4 | 8 | 8 |
| 5 | 8 | 8 | 8 | 8 | 5 | 8 | 8 |
| 6 | 7 | 8 | 8 | 7 | 6 | 8 | 8 |
| 7 | 6 | 8 | 8 | 6 | 7 | 8 | 8 |
| 8 | 5 | 8 | 8 | 5 | 8 | 8 | 8 |
| 9 | 4 | 8 | 8 | 4 | 9 | 8 | 8 |
| 10 | 3 | 8 | 8 | 3 | 10 | 8 | 8 |
| 11 | 2 | 8 | 8 | 2 | 11 | 8 | 8 |
| 12 | 1 | 8 | 8 | 1 | 12 | 8 | 8 |
| 1 | 12 | 9 | 7 | 12 | 1 | 9 | 7 |
| 2 | 11 | 9 | 7 | 11 | 2 | 9 | 7 |
| 3 | 10 | 9 | 7 | 10 | 3 | 9 | 7 |
| 4 | 9 | 9 | 7 | 9 | 4 | 9 | 7 |
| 5 | 8 | 9 | 7 | 8 | 5 | 9 | 7 |
| 6 | 7 | 9 | 7 | 7 | 6 | 9 | 7 |
| 7 | 6 | 9 | 7 | 6 | 7 | 9 | 7 |
| 8 | 5 | 9 | 7 | 5 | 8 | 9 | 7 |
| 9 | 4 | 9 | 7 | 4 | 9 | 9 | 7 |
| 10 | 3 | 9 | 7 | 3 | 10 | 9 | 7 |
| 11 | 2 | 9 | 7 | 2 | 11 | 9 | 7 |
| 12 | 1 | 9 | 7 | 1 | 12 | 9 | 7 |
| 1 | 12 | 10 | 6 | 12 | 1 | 10 | 6 |
| 2 | 11 | 10 | 6 | 11 | 2 | 10 | 6 |
| 3 | 10 | 10 | 6 | 10 | 3 | 10 | 6 |
| 4 | 9 | 10 | 6 | 9 | 4 | 10 | 6 |
| 5 | 8 | 10 | 6 | 8 | 5 | 10 | 6 |
| 6 | 7 | 10 | 6 | 7 | 6 | 10 | 6 |
| 7 | 6 | 10 | 6 | 6 | 7 | 10 | 6 |
| 8 | 5 | 10 | 6 | 5 | 8 | 10 | 6 |
| 9 | 4 | 10 | 6 | 4 | 9 | 10 | 6 |
| 10 | 3 | 10 | 6 | 3 | 10 | 10 | 6 |
| 11 | 2 | 10 | 6 | 2 | 11 | 10 | 6 |

-continued

| | | | | | | | |
|---|---|---|---|---|---|---|---|
| 12 | 1 | 10 | 6 | 1 | 12 | 10 | 6 |
| 1 | 12 | 11 | 5 | 12 | 1 | 11 | 5 |
| 2 | 11 | 11 | 5 | 11 | 2 | 11 | 5 |
| 3 | 10 | 11 | 5 | 10 | 3 | 11 | 5 |
| 4 | 9 | 11 | 5 | 9 | 4 | 11 | 5 |
| 5 | 8 | 11 | 5 | 8 | 5 | 11 | 5 |
| 6 | 7 | 11 | 5 | 7 | 6 | 11 | 5 |
| 7 | 6 | 11 | 5 | 6 | 7 | 11 | 5 |
| 8 | 5 | 11 | 5 | 5 | 8 | 11 | 5 |
| 9 | 4 | 11 | 5 | 4 | 9 | 11 | 5 |
| 10 | 3 | 11 | 5 | 3 | 10 | 11 | 5 |
| 11 | 2 | 11 | 5 | 2 | 11 | 11 | 5 |
| 12 | 1 | 11 | 5 | 1 | 12 | 11 | 5 |
| 1 | 12 | 12 | 4 | 12 | 1 | 12 | 4 |
| 2 | 11 | 12 | 4 | 11 | 2 | 12 | 4 |
| 3 | 10 | 12 | 4 | 10 | 3 | 12 | 4 |
| 4 | 9 | 12 | 4 | 9 | 4 | 12 | 4 |
| 5 | 8 | 12 | 4 | 8 | 5 | 12 | 4 |
| 6 | 7 | 12 | 4 | 7 | 6 | 12 | 4 |
| 7 | 6 | 12 | 4 | 6 | 7 | 12 | 4 |
| 8 | 5 | 12 | 4 | 5 | 8 | 12 | 4 |
| 9 | 4 | 12 | 4 | 4 | 9 | 12 | 4 |
| 10 | 3 | 12 | 4 | 3 | 10 | 12 | 4 |
| 11 | 2 | 12 | 4 | 2 | 11 | 12 | 4 |
| 12 | 1 | 12 | 4 | 1 | 12 | 12 | 4 |
| 1 | 12 | 13 | 3 | 12 | 1 | 13 | 3 |
| 2 | 11 | 13 | 3 | 11 | 2 | 13 | 3 |
| 3 | 10 | 13 | 3 | 10 | 3 | 13 | 3 |
| 4 | 9 | 13 | 3 | 9 | 4 | 13 | 3 |
| 5 | 8 | 13 | 3 | 8 | 5 | 13 | 3 |
| 6 | 7 | 13 | 3 | 7 | 6 | 13 | 3 |
| 7 | 6 | 13 | 3 | 6 | 7 | 13 | 3 |
| 8 | 5 | 13 | 3 | 5 | 8 | 13 | 3 |
| 9 | 4 | 13 | 3 | 4 | 9 | 13 | 3 |
| 10 | 3 | 13 | 3 | 3 | 10 | 13 | 3 |
| 11 | 2 | 13 | 3 | 2 | 11 | 13 | 3 |
| 12 | 1 | 13 | 3 | 1 | 12 | 13 | 3 |
| 1 | 12 | 14 | 2 | 12 | 1 | 14 | 2 |
| 2 | 11 | 14 | 2 | 11 | 2 | 14 | 2 |
| 3 | 10 | 14 | 2 | 10 | 3 | 14 | 2 |
| 4 | 9 | 14 | 2 | 9 | 4 | 14 | 2 |
| 5 | 8 | 14 | 2 | 8 | 5 | 14 | 2 |
| 6 | 7 | 14 | 2 | 7 | 6 | 14 | 2 |
| 7 | 6 | 14 | 2 | 6 | 7 | 14 | 2 |
| 8 | 5 | 14 | 2 | 5 | 8 | 14 | 2 |
| 9 | 4 | 14 | 2 | 4 | 9 | 14 | 2 |
| 10 | 3 | 14 | 2 | 3 | 10 | 14 | 2 |
| 11 | 2 | 14 | 2 | 2 | 11 | 14 | 2 |
| 12 | 1 | 14 | 2 | 1 | 12 | 14 | 2 |
| 1 | 12 | 7 | 9 | 12 | 1 | 7 | 9 |
| 2 | 11 | 7 | 9 | 11 | 2 | 7 | 9 |
| 3 | 10 | 7 | 9 | 10 | 3 | 7 | 9 |
| 4 | 9 | 7 | 9 | 9 | 4 | 7 | 9 |

-continued

| | | | | | | | |
|---|---|---|---|---|---|---|---|
| 5 | 8 | 7 | 9 | 8 | 5 | 7 | 9 |
| 6 | 7 | 7 | 9 | 7 | 6 | 7 | 9 |
| 7 | 6 | 7 | 9 | 6 | 7 | 7 | 9 |
| 8 | 5 | 7 | 9 | 5 | 8 | 7 | 9 |
| 9 | 4 | 7 | 9 | 4 | 9 | 7 | 9 |
| 10 | 3 | 7 | 9 | 3 | 10 | 7 | 9 |
| 11 | 2 | 7 | 9 | 2 | 11 | 7 | 9 |
| 12 | 1 | 7 | 9 | 1 | 12 | 7 | 9 |
| 12 | 1 | 6 | 10 | 12 | 1 | 6 | 10 |
| 1 | 12 | 6 | 10 | 11 | 2 | 6 | 10 |
| 2 | 11 | 6 | 10 | 10 | 3 | 6 | 10 |
| 3 | 10 | 6 | 10 | 9 | 4 | 6 | 10 |
| 4 | 9 | 6 | 10 | 8 | 5 | 6 | 10 |
| 5 | 8 | 6 | 10 | 7 | 6 | 6 | 10 |
| 6 | 7 | 6 | 10 | 6 | 7 | 6 | 10 |
| 7 | 6 | 6 | 10 | 5 | 8 | 6 | 10 |
| 8 | 5 | 6 | 10 | 4 | 9 | 6 | 10 |
| 9 | 4 | 6 | 10 | 3 | 10 | 6 | 10 |
| 10 | 3 | 6 | 10 | 2 | 11 | 6 | 10 |
| 11 | 2 | 6 | 10 | 1 | 12 | 6 | 10 |
| 12 | 1 | 6 | 10 | 12 | 1 | 6 | 10 |
| 1 | 12 | 5 | 11 | 11 | 2 | 5 | 11 |
| 2 | 11 | 5 | 11 | 10 | 3 | 5 | 11 |
| 3 | 10 | 5 | 11 | 9 | 4 | 5 | 11 |
| 4 | 9 | 5 | 11 | 8 | 5 | 5 | 11 |
| 5 | 8 | 5 | 11 | 7 | 6 | 5 | 11 |
| 6 | 7 | 5 | 11 | 6 | 7 | 5 | 11 |
| 7 | 6 | 5 | 11 | 5 | 8 | 5 | 11 |
| 8 | 5 | 5 | 11 | 4 | 9 | 5 | 11 |
| 9 | 4 | 5 | 11 | 3 | 10 | 5 | 11 |
| 10 | 3 | 5 | 11 | 2 | 11 | 5 | 11 |
| 11 | 2 | 5 | 11 | 1 | 12 | 5 | 11 |
| 12 | 1 | 5 | 11 | 12 | 1 | 5 | 11 |
| 1 | 12 | 4 | 12 | 11 | 2 | 4 | 12 |
| 2 | 11 | 4 | 12 | 10 | 3 | 4 | 12 |
| 3 | 10 | 4 | 12 | 9 | 4 | 4 | 12 |
| 4 | 9 | 4 | 12 | 8 | 5 | 4 | 12 |
| 5 | 8 | 4 | 12 | 7 | 6 | 4 | 12 |
| 6 | 7 | 4 | 12 | 6 | 7 | 4 | 12 |
| 7 | 6 | 4 | 12 | 5 | 8 | 4 | 12 |
| 8 | 5 | 4 | 12 | 4 | 9 | 4 | 12 |
| 9 | 4 | 4 | 12 | 3 | 10 | 4 | 12 |
| 10 | 3 | 4 | 12 | 2 | 11 | 4 | 12 |
| 11 | 2 | 4 | 12 | 1 | 12 | 4 | 12 |
| 12 | 1 | 4 | 12 | 12 | 1 | 4 | 12 |

-continued
| 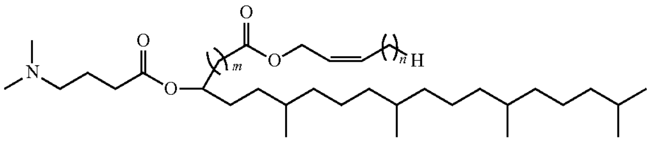 | | 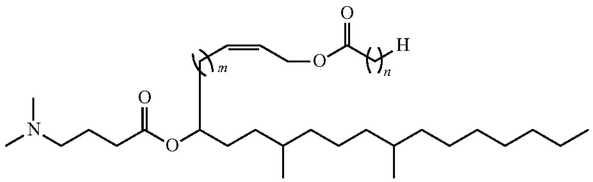 | |
|---|---|---|---|
| m | n | m | n |
| 1 | 12 | 12 | 1 |
| 2 | 11 | 11 | 2 |
| 3 | 10 | 10 | 3 |
| 4 | 9 | 9 | 4 |
| 5 | 8 | 8 | 5 |
| 6 | 7 | 7 | 6 |
| 7 | 6 | 6 | 7 |
| 8 | 5 | 5 | 8 |
| 9 | 4 | 4 | 9 |
| 10 | 3 | 3 | 10 |
| 11 | 2 | 2 | 11 |
| 12 | 1 | 1 | 12 |
| 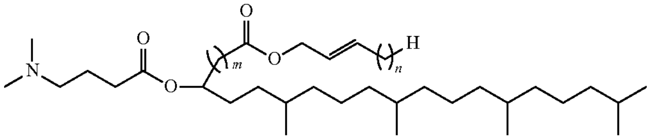 | | 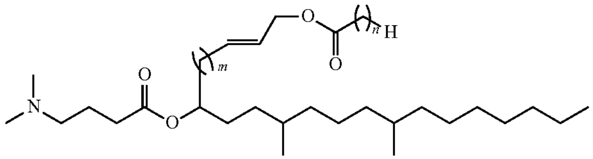 | |
| 1 | 12 | 12 | 1 |
| 2 | 11 | 11 | 2 |
| 3 | 10 | 10 | 3 |
| 4 | 9 | 9 | 4 |
| 5 | 8 | 8 | 5 |
| 6 | 7 | 7 | 6 |
| 7 | 6 | 6 | 7 |
| 8 | 5 | 5 | 8 |
| 9 | 4 | 4 | 9 |
| 10 | 3 | 3 | 10 |
| 11 | 2 | 2 | 11 |
| 12 | 1 | 1 | 12 |

-continued
| 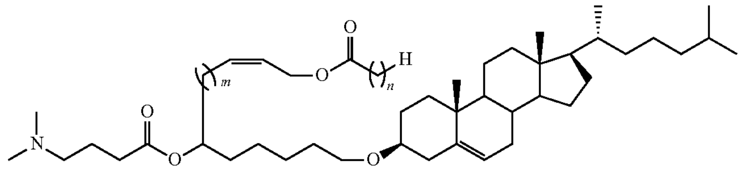 | | 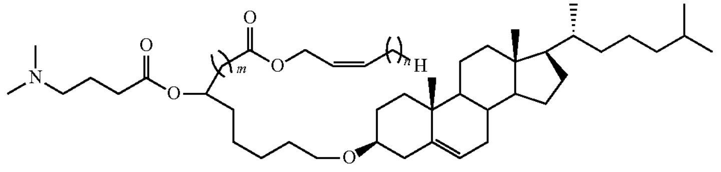 | |
|---|---|---|---|
| m | n | m | n |
| 1 | 12 | 12 | 1 |
| 2 | 11 | 11 | 2 |
| 3 | 10 | 10 | 3 |
| 4 | 9 | 9 | 4 |
| 5 | 8 | 8 | 5 |
| 6 | 7 | 7 | 6 |
| 7 | 6 | 6 | 7 |
| 8 | 5 | 5 | 8 |
| 9 | 4 | 4 | 9 |
| 10 | 3 | 3 | 10 |
| 11 | 2 | 2 | 11 |
| 12 | 1 | 1 | 12 |
| 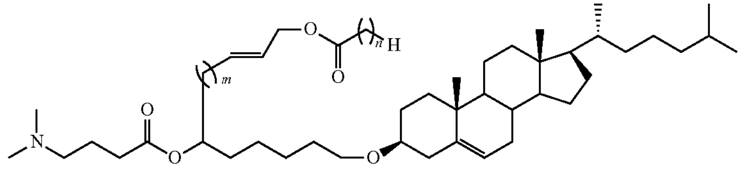 | | 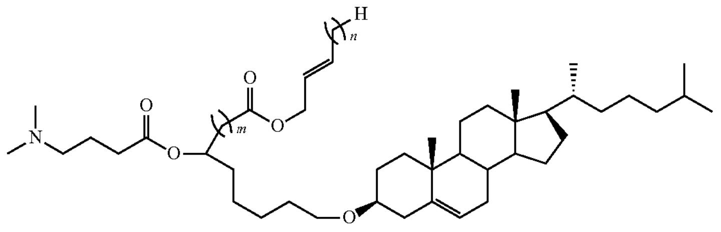 | |
|---|---|---|---|
| 1 | 12 | 12 | 1 |
| 2 | 11 | 11 | 2 |
| 3 | 10 | 10 | 3 |
| 4 | 9 | 9 | 4 |
| 5 | 8 | 8 | 5 |
| 6 | 7 | 7 | 6 |
| 7 | 6 | 6 | 7 |
| 8 | 5 | 5 | 8 |
| 9 | 4 | 4 | 9 |
| 10 | 3 | 3 | 10 |
| 11 | 2 | 2 | 11 |
| 12 | 1 | 1 | 12 |

and salts thereof.
Among the above-mentioned cationic lipids, cationic lipids represented by the following structural formulas are more preferable.
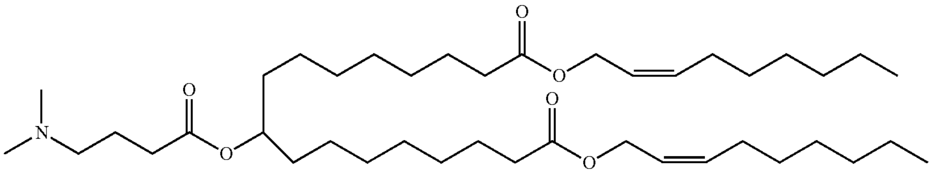
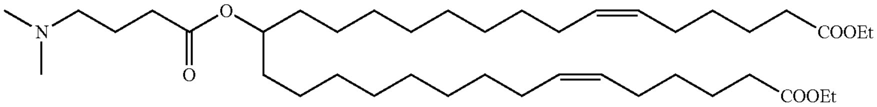
and
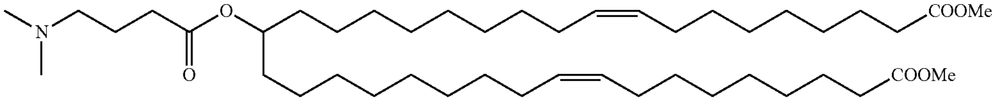
and salts thereof.
In another embodiment, cationic lipids represented by the following structural formulas and described in WO 2013/126803 can be mentioned.
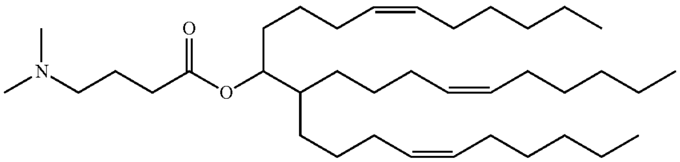
,
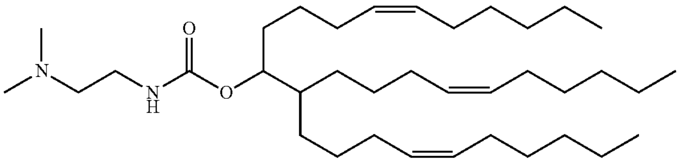
,
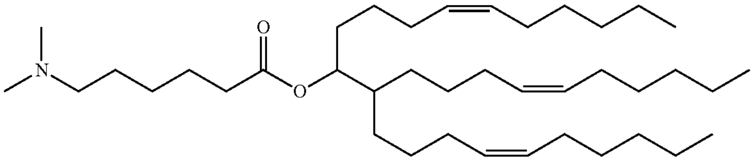
,
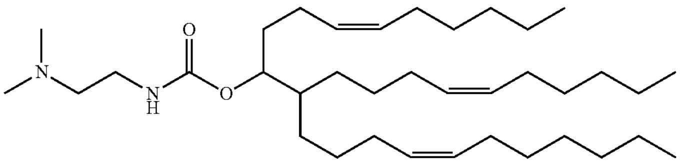
,
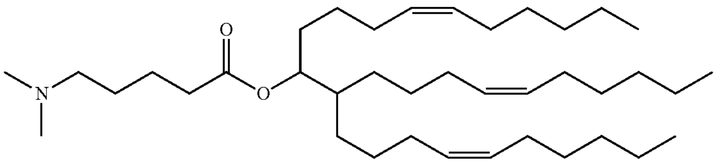
,
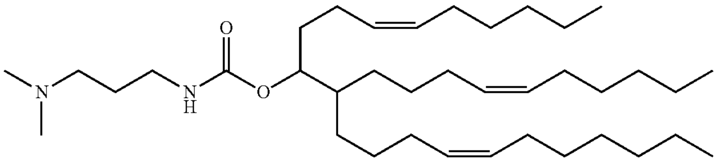
, -continued
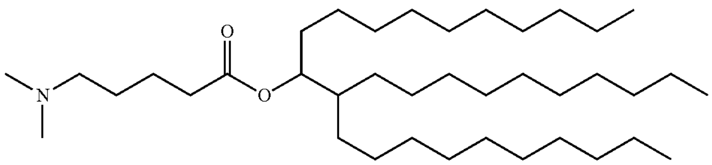
,
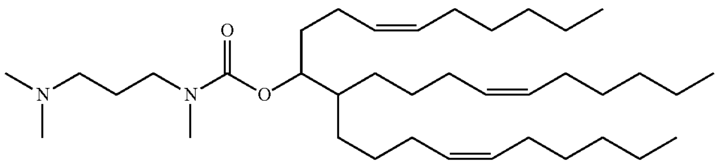 [SMILES: CCCCC/C=C\CCCC(CCC/C=C\CCCCC)C(CC/C=C\CCCCC)OC(=O)CCCCN(C)C]
,
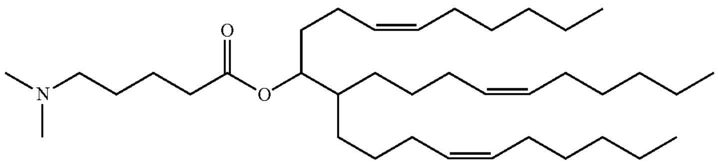
,
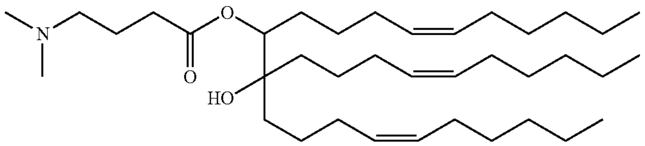
,
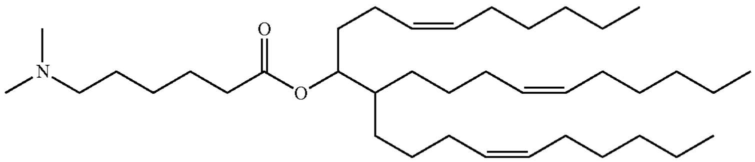
,
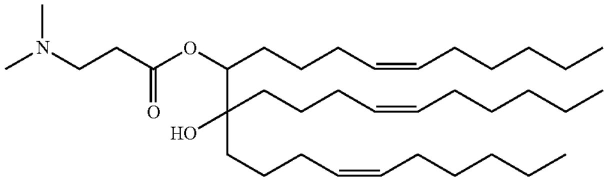
,
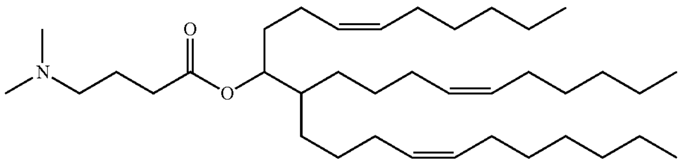
,
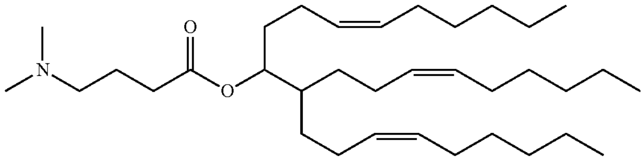
,
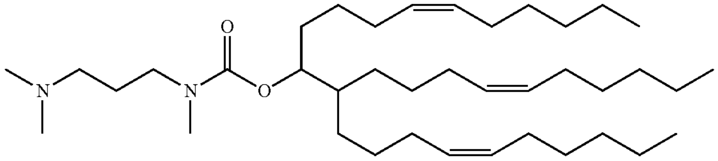
,
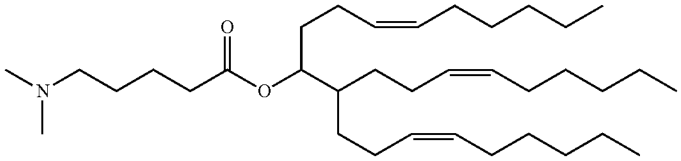
, -continued
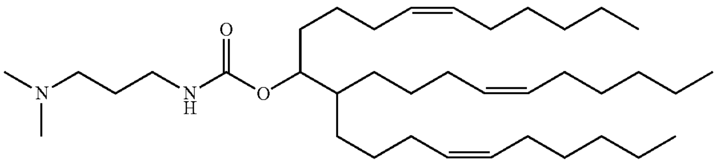,
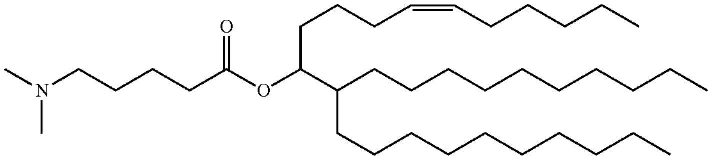,
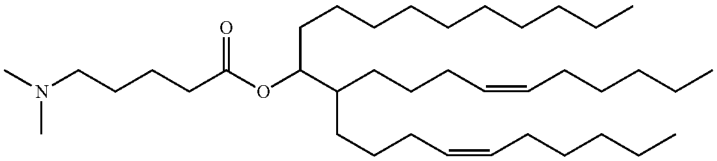,
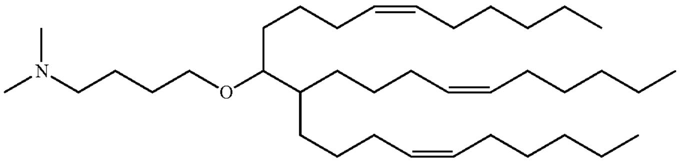,
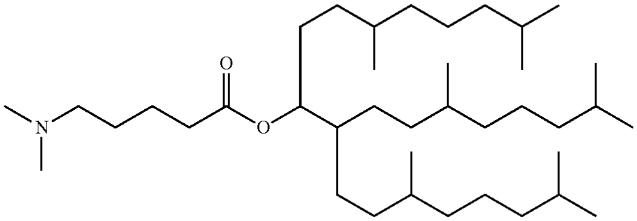
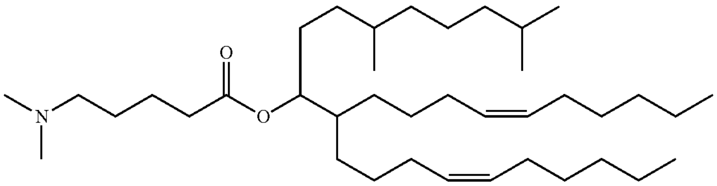,
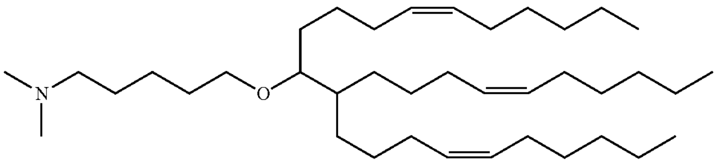,
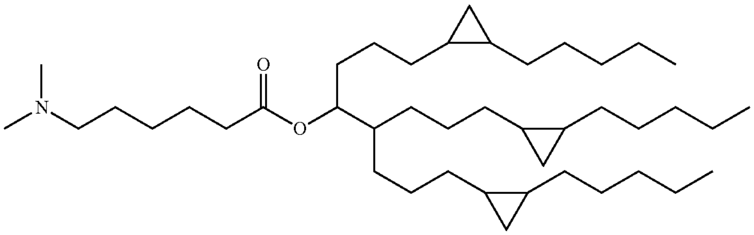,
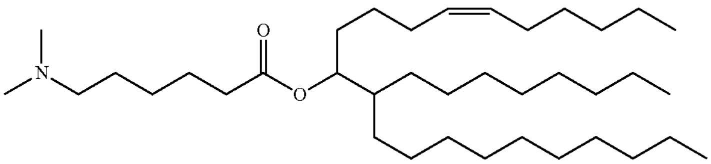, -continued

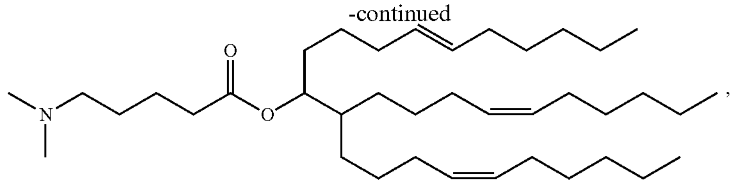

and

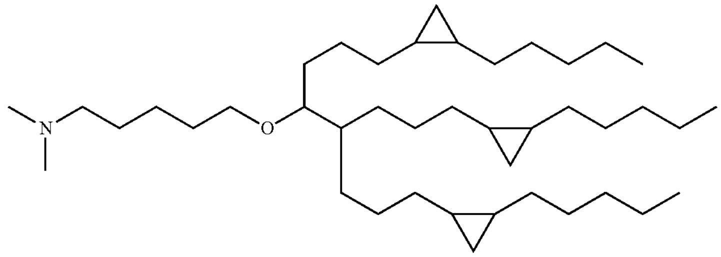

and salts thereof.

Among the above-mentioned cationic lipids, a cationic lipid represented by the following structural formula is more preferable.

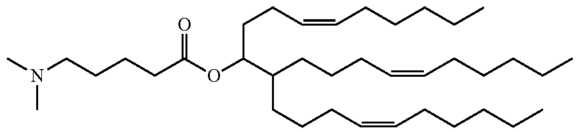

and a salt thereof.

In another embodiment, cationic lipids K-E12, H-A12, Y-E12, G-O12, K-A12, R-A12, cKK-E12, cPK-E12, PK1K-E12, PK500-E12, cQK-E12, cKK-A12, KK-A12, PK-4K-E12, cWK-E12, PK500-O12, PK1K-O12, cYK-E12, cDK-E12, cSK-E12, cEK-E12, cMK-E12, cKK-O12, cIK-E12, cKK-E10, cKK-E14, and cKK-E16 synthesized by the following scheme described in Dong et al. (Proc Natl Acad Sci USA. 2014 Apr. 15; 111(15):5753) can be mentioned.

Amino Acid

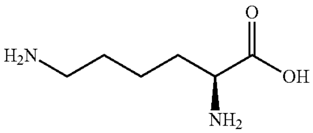

K

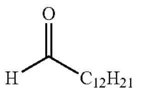

A12

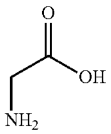

G

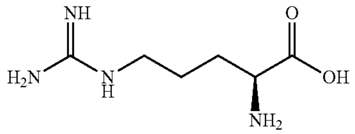

R

E (epoxide) 10
E14
E16

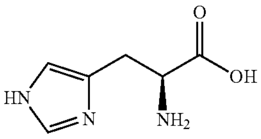

H

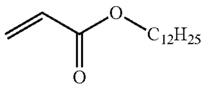

O12

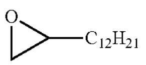

E12

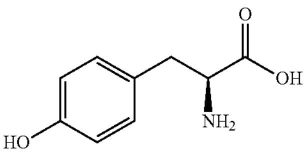

Y

-continued
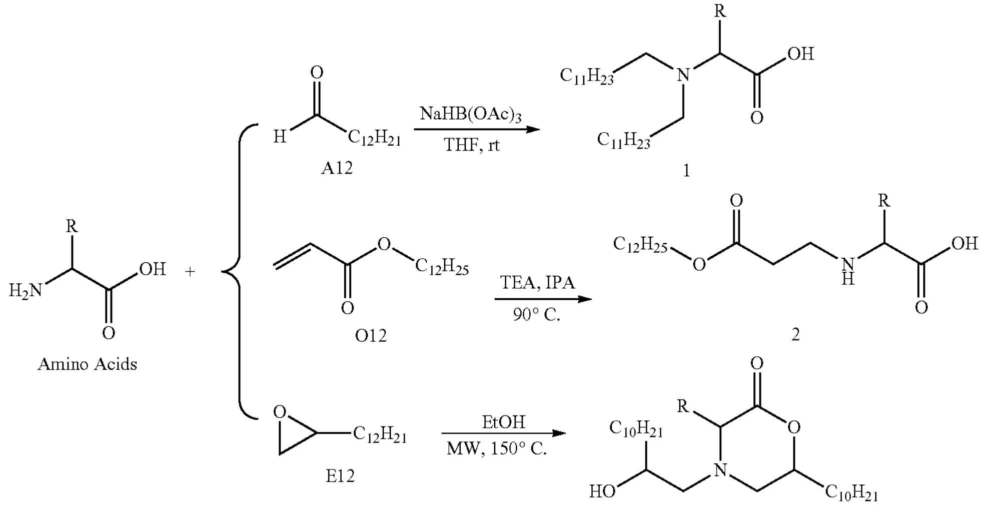
Amino Acids
A12
O12
E12
1
2
3
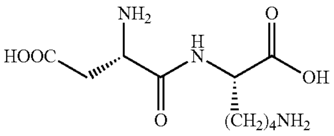
DK
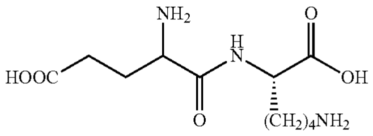
EK
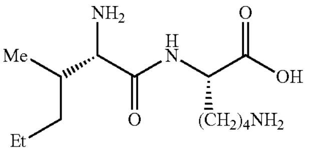
IK
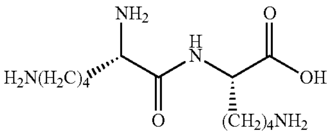
KK
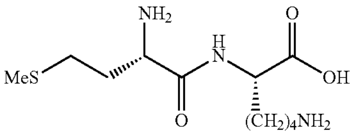
MK
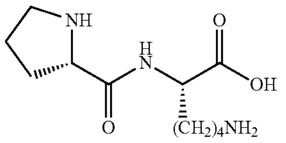
PK
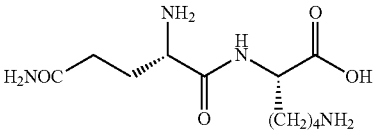
QK
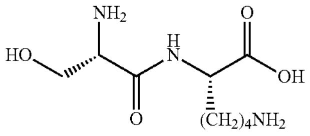
SK
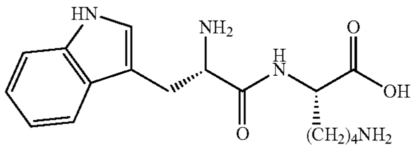
WK
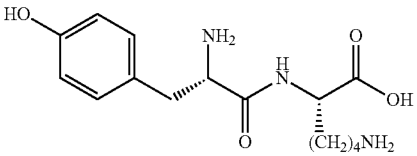
YK
PK 500 (Poly-L-lysine hydrobromide 500-2000)
PK1K (Poly-L-lysine hydrobromide 1000-5000)
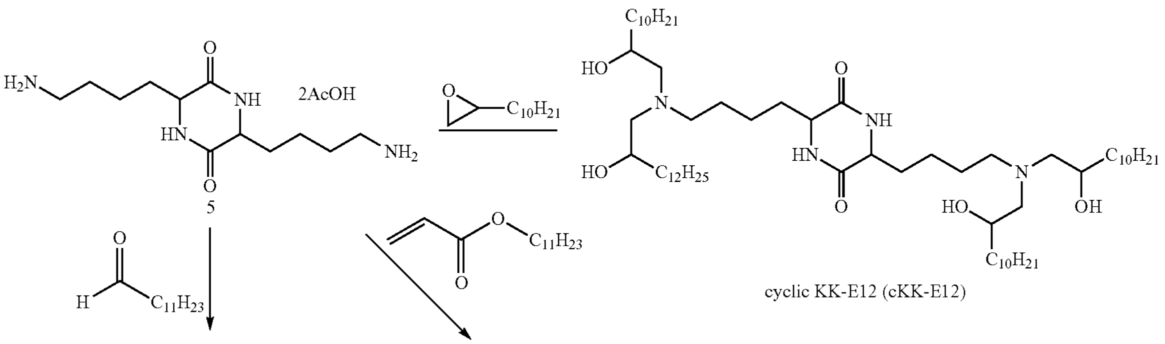
5
cyclic KK-E12 (cKK-E12)

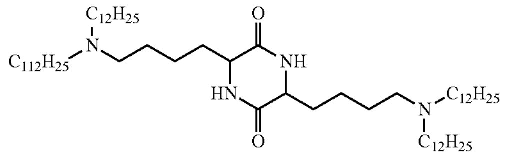

cKK-A12

-continued

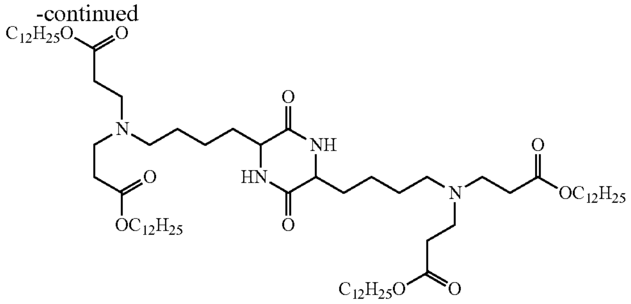

cKK-O12

Among the above-mentioned cationic lipids, cKK-E12, cKK-E14 are more preferable.

In another embodiment, cationic lipids C14-98, C18-96, C14-113, C14-120, C14-120, C14-110, C16-96, and C12-200 synthesized by the following scheme described in Love K T et al. (Proc Natl Acad Sci USA. 2010 May 25; 107(21):9915) can be mentioned.

C12

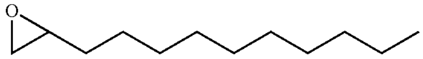

C14

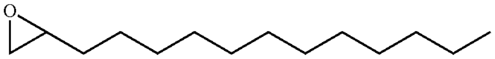

C16

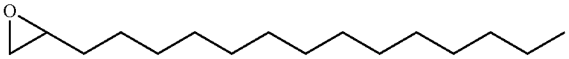

96

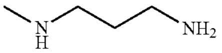

98

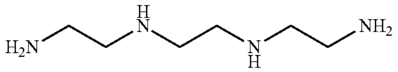

110

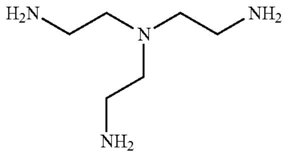

113

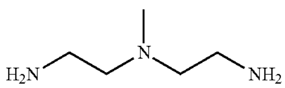

120

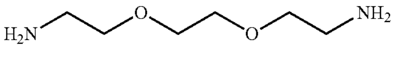

200

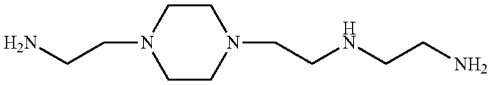

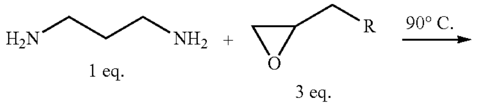

-continued

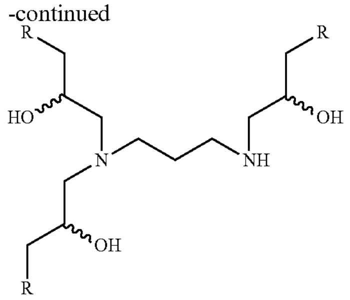

Among the above-mentioned cationic lipids, C14-110, C16-96 and C12-200 are more preferable.

In a particularly preferable embodiment, a cationic lipid represented by the following formula (I) (hereinafter to be also referred to as "compound (I)") can be mentioned.

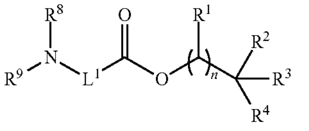

(I)

wherein $L^1$ is a $C_{1-22}$ alkylene group, a $C_{2-22}$ alkenylene group or a $C_{3-22}$ alkadienylene group, n is an integer of 0 or 1, $R^1$ is (1) a hydrogen atom, (2) a linear $C_{1-22}$ alkyl group optionally substituted by one or two substituents selected from a linear $C_{1-22}$ alkyl group and a linear $C_{2-22}$ alkenyl group, (3) a linear $C_{2-22}$ alkenyl group optionally substituted by one or two substituents selected from a linear $C_{1-22}$ alkyl group and a linear $C_{2-22}$ alkenyl group, or (4) a linear $C_{3-22}$ alkadienyl group optionally substituted by one or two substituents selected from a linear $C_{1-22}$ alkyl group and a linear $C_{2-22}$ alkenyl group, $R^2$ is —$CH_2$—O—CO—$R^5$, —$CH_2$—CO—O—$R^5$ or —$R^5$, $R^3$ is —$CH_2$—O—CO—$R^6$, —$CH_2$—CO—O—$R^6$ or —$R^6$, $R^4$ is a hydrogen atom, —$CH_2$—O—CO—$R^7$, —$CH_2$—CO—O—$R^7$ or —$R^7$, $R^5$, $R^6$ and $R^7$ are each independently (1) a linear $C_{1-22}$ alkyl group optionally substituted by one or two substituents selected from a linear $C_{1-22}$ alkyl group and a linear $C_{2-22}$ alkenyl group, (2) a linear $C_{2-22}$ alkenyl group optionally substituted by one or two substituents selected from a linear $C_{1-22}$ alkyl group and a linear $C_{2-22}$ alkenyl group, or (3) a linear $C_{3-22}$ alkadienyl group optionally substituted by one or two substituents selected from a linear $C_{1-22}$ alkyl group and a linear $C_{2-22}$ alkenyl group, and $R_8$ and $R_9$ are each independently a $C_{1-6}$ alkyl group, or a salt thereof.

$L^1$ is a $C_{1-22}$ alkylene group, a $C_{2-22}$ alkenylene group or a $C_{3-22}$ alkadienylene group.

$L^1$ is preferably a $C_{1-22}$ alkylene group.

$L^1$ is more preferably a $C_{1-12}$ alkylene group.

$L^1$ is further preferably a $C_{1-6}$ alkylene group.

n is an integer of 0 or 1.

n is preferably an integer of 1.

$R^1$ is (1) a hydrogen atom, (2) a linear $C_{1-22}$ alkyl group optionally substituted by one or two substituents selected from a linear $C_{1-22}$ alkyl group and a linear $C_{2-22}$ alkenyl group, (3) a linear $C_{2-22}$ alkenyl group optionally substituted by one or two substituents selected from a linear $C_{1-22}$ alkyl group and a linear $C_{2-22}$ alkenyl group, or (4) a linear $C_{3-22}$ alkadienyl group optionally substituted by one or two substituents selected from a linear $C_{1-22}$ alkyl group and a linear $C_{2-22}$ alkenyl group.

$R^1$ is preferably (1) a hydrogen atom, (2) a linear $C_{1-22}$ alkyl group (preferably linear $C_{6-12}$ alkyl group) optionally substituted by one or two linear $C_{1-22}$ alkyl groups (preferably linear $C_{6-12}$ alkyl groups), or (3) a linear $C_{2-22}$ alkenyl group (preferably linear $C_{6-12}$ alkenyl group) optionally substituted by one or two linear $C_{2-22}$ alkenyl groups (preferably linear $C_{6-12}$ alkenyl groups).

$R^1$ is particularly preferably a hydrogen atom.

$R^2$ is —$CH_2$—O—CO—$R^5$, —$CH_2$—CO—O—$R^5$ or —$R^5$.

$R^2$ is preferably —$CH_2$—O—CO—$R^5$ or —$R^5$.

$R^2$ is more preferably —$CH_2$—O—CO—$R^5$.

$R^3$ is —$CH_2$—O—CO—$R^6$, —$CH_2$—CO—O—$R^6$ or —$R^6$.

$R^3$ is preferably —$CH_2$—O—CO—$R^6$ or —$R^6$.

$R^3$ is more preferably —$CH_2$—O—CO—$R^6$.

$R^4$ is a hydrogen atom, —$CH_2$—O—CO—$R^7$, —$CH_2$—CO—O—$R^7$ or —$R^6$.

$R^4$ is preferably a hydrogen atom or —$CH_2$—O—CO—$R^7$.

$R^4$ is more preferably —$CH_2$—O—CO—$R^7$.

$R^5$, $R^6$ and $R^7$ are each independently (1) a linear $C_{1-22}$ alkyl group optionally substituted by one or two substituents selected from a linear $C_{1-22}$ alkyl group and a linear $C_{2-22}$ alkenyl group, (2) a linear $C_{2-22}$ alkenyl group optionally substituted by one or two substituents selected from a linear $C_{1-22}$ alkyl group and a linear $C_{2-22}$ alkenyl group, or (3) a linear $C_{3-22}$ alkadienyl group optionally substituted by one or two substituents selected from a linear $C_{1-22}$ alkyl group and a linear $C_{2-22}$ alkenyl group.

$R^5$, $R^6$ and $R^7$ are each independently preferably (1) a linear $C_{1-22}$ alkyl group (preferably linear $C_{4-18}$ alkyl group) optionally substituted by one or two linear $C_{1-22}$ alkyl groups (preferably linear $C_{1-10}$ alkyl groups), (2) a linear $C_{2-22}$ alkenyl group (preferably linear $C_{4-18}$ alkenyl group), or (3) a linear $C_{3-22}$ alkadienyl group (preferably linear $C_{4-18}$ alkadienyl group).

$R^5$, $R^6$ and $R^7$ are each independently more preferably (1) a linear $C_{1-22}$ alkyl group (preferably linear $C_{4-18}$ alkyl group) optionally substituted by one or two linear $C_{1-22}$ alkyl groups (preferably linear $C_{1-10}$ alkyl groups), or (2) a linear $C_{2-22}$ alkenyl group (preferably linear $C_{4-18}$ alkenyl group).

$R_8$ and $R_9$ are each independently a $C_{1-6}$ alkyl group.

$R_8$ and $R_9$ are each independently a $C_{1-3}$ alkyl group (preferably methyl).

Preferably, compound (I) is a compound of the above-mentioned formula (I) wherein $L^1$ is a $C_{1-22}$ alkylene group (preferably $C_{1-12}$ alkylene group, more preferably $C_{1-6}$ alkylene group), n is an integer of 1, $R^1$ is (1) a hydrogen atom, (2) a linear $C_{1-22}$ alkyl group (preferably linear $C_{6-12}$ alkyl group) optionally substituted by one or two linear $C_{1-22}$ alkyl groups (preferably linear $C_{6-12}$ alkyl groups), or (3) a linear $C_{2-22}$ alkenyl group (preferably linear $C_{6-12}$ alkenyl group) optionally substituted by one or two linear $C_{2-22}$ alkenyl groups (preferably linear $C_{6-12}$ alkenyl groups), $R^2$ is —$CH_2$—O—CO—$R^5$ or —$R^5$, $R^3$ is —$CH_2$—O—CO—$R^6$ or —$R^6$, $R^4$ is a hydrogen atom or —$CH_2$—O—CO—$R^7$, $R^5$, $R^6$ and $R^7$ are each independently (1) a linear $C_{1-22}$ alkyl group (preferably linear $C_{4-18}$ alkyl group) optionally substituted by one or two linear $C_{1-22}$ alkyl groups (preferably linear $C_{1-10}$ alkyl groups), (2) a linear $C_{2-22}$ alkenyl group (preferably linear $C_{4-18}$ alkenyl group), or (3) a linear $C_{3-22}$ alkadienyl group (preferably linear $C_{4-18}$ alkadienyl group), and $R_8$ and $R_9$ are each independently a $C_{1-6}$ alkyl group (preferably $C_{1-3}$ alkyl group, particularly preferably methyl).

More preferably, compound (I) is a compound of the above-mentioned formula (I) wherein $L^1$ is a $C_{1-12}$ alkylene group (preferably $C_{1-6}$ alkylene group), n is an integer of 1, $R^1$ is a hydrogen atom, $R^2$ is —$CH_2$—O—CO—$R^5$, $R^3$ is —$CH_2$—O—CO—$R^6$, $R^4$ is —$CH_2$—O—CO—$R^7$, $R^5$, $R^6$ and $R^7$ are each independently (1) a linear $C_{1-22}$ alkyl group (preferably linear $C_{4-18}$ alkyl group) optionally substituted by one or two linear $C_{1-22}$ alkyl groups (preferably linear $C_{1-10}$ alkyl groups), (2) a linear $C_{2-22}$ alkenyl group (preferably linear $C_{4-18}$ alkenyl group), or (3) a linear $C_{3-22}$ alkadienyl group (preferably linear $C_{4-18}$ alkadienyl group), and $R_8$ and $R_9$ are each independently a $C_{1-6}$ alkyl group (preferably $C_{1-3}$ alkyl group, particularly preferably methyl).

More preferably, compound (I) is a compound of the above-mentioned formula (I) wherein $L^1$ is a $C_{1-6}$ alkylene group, n is an integer of 1, $R^1$ is a hydrogen atom, $R^2$ is —$CH_2$—O—CO—$R^5$, $R^3$ is —$CH_2$—O—CO—$R^6$, $R^4$ is —$CH_2$—O—CO—$R^7$, $R^5$, $R^6$ and $R^7$ are each independently (1) a linear $C_{1-22}$ alkyl group (preferably linear $C_{4-18}$ alkyl group) optionally substituted by one or two linear $C_{1-22}$ alkyl groups (preferably linear $C_{1-10}$ alkyl groups), or (2) a linear $C_{2-22}$ alkenyl group (preferably linear $C_{4-18}$ alkenyl group), and $R_8$ and $R_9$ are each independently a $C_{1-3}$ alkyl group (preferably methyl).

A salt of the compound represented by the above-mentioned each structural formula is preferably a pharmacologically acceptable salt. Examples thereof include salts with inorganic bases (e.g., alkali metal salts such as sodium salt, potassium salt and the like; alkaline earth metal salts such as calcium salt, magnesium salt and the like; aluminum salt, ammonium salt), salts with organic bases (e.g., salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N-dibenzyl ethylenediamine), salts with inorganic acids (e.g., salts with hydrofluoric acid, hydrochloric acid, hydrobromic acid, hydrogen iodide acid, nitric acid, sulfuric acid, phosphoric acid), salts with organic acids (salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid), salts with basic amino acids (salts with arginine, lysine, ornithine) or salts with acidic amino acids (salts with aspartic acid, glutamic acid).

The ratio (mol %) of the cationic lipid to the total lipids present in the lipid nanoparticle of the present invention is, for example, about 10% to about 80%, preferably about 20% to about 70%, more preferably about 40% to about 60%; however, the ratio is not limited to these.

Only one kind of the above-mentioned cationic lipid may also be used or two or more kinds thereof may be used in combination. When multiple cationic lipids are used, the ratio of the whole cationic lipid is preferably as mentioned above.

(c) Non-Cationic Lipid

In the present specification, the "non-cationic lipid" means a lipid other than the cationic lipid, and is a lipid that does not have a net positive electric charge at a selected pH such as physiological pH and the like. Examples of the non-cationic lipid used in the lipid nanoparticle of the present invention include phospholipid, steroids, PEG lipid and the like.

To enhance the delivery of nucleic acid encoding CAR or exogenous TCR into the target immunocyte, the phospholipid is not particularly limited as long as it stably maintains nucleic acid and does not inhibit fusion with cell membranes (palsma membrane and organelle membrane). For example, phosphatidyl choline, phosphatidyl ethanolamine, phosphatidyl serine, phosphatidyl inositol, phosphatidic acid, palmitoyloleoylphosphatidyl choline, lysophosphatidyl choline, lysophosphatidyl ethanolamine, dipalmitoylphosphatidyl choline, dioleoylphosphatidyl choline, distearoylphosphatidyl choline, dilinolenoylphosphatidyl choline and the like can be mentioned.

Preferred phospholipids include distearoylphosphatidyl choline (DSPC), dioleoylphosphatidyl choline (DOPC), dipalmitoylphosphatidyl choline (DPPC), dioleoylphosphatidyl glycerol (DOPG), palmitoyloleoylphosphatidyl glycerol (POPG), dipalmitoylphosphatidyl glycerol (DPPG), dioleoyl-phosphatidyl ethanolamine (DOPE), palmitoyloleoylphosphatidyl choline (POPC), palmitoyloleoyl-phosphatidyl ethanolamine (POPE), and dioleoylphosphatidyl ethanolamine 4-(N-maleimide methyl)-cyclo hexane-1-carboxylate (DOPE-mal), more preferably DOPC, DPPC, POPC, and DOPE.

The ratio (mol %) of the phospholipid to the total lipids present in the lipid nanoparticle of the present invention may be, for example, about 0% to about 90%, preferably about 5% to about 30%, more preferably about 8% to about 15%.

Only one kind of the above-mentioned phospholipid may be used or two or more kinds thereof may be used in combination. When multiple phospholipids are used, the ratio of the whole phospholipid is preferably as mentioned above.

As the steroids, cholesterol, 5α-cholestanol, 5β-coprostanol, cholesteryl-(2'-hydroxy)-ethylether, cholesteryl-(4'-hydroxy)-butylether, 6-ketocholestanol, 5α-cholestane, cholestenone, 5α-cholestanone, 5β-cholestanone, and cholesteryl decanoate can be mentioned, preferably cholesterol.

The ratio (mol %) of the steroid to the total lipids present in the lipid nanoparticle of the present invention when steroids are present may be, for example, about 10% to about 60%, preferably about 12% to about 58%, more preferably about 20% to about 55%.

Only one kind of the above-mentioned steroid may be used or two or more kinds thereof may be used in combination. When multiple steroids are used, the ratio of the whole steroid is preferably as mentioned above.

In the present specification, the "PEG lipid" means any complex of polyethylene glycol (PEG) and lipid. PEG lipid is not particularly limited as long as it has an effect of suppressing aggregation of the lipid nanoparticle of the present invention. For example, PEG conjugated with dialkyloxypropyl (PEG-DAA), PEG conjugated with diacylglycerol (PEG-DAG) (e.g., SUNBRIGHT GM-020 (NOF CORPORATION)), PEG conjugated with phospholipids such as phosphatidylethanolamine (PEG-PE), PEG conjugated with ceramide (PEG-Cer), PEG conjugated with cholesterol (PEG-cholesterol), or derivatives thereof, or mixtures thereof, mPEG2000-1,2-Di-O-alkyl-sn3-carbomoylglyceride (PEG-C-DOMG), 1-[8'-(1,2-dimyristoyl-3-propanoxy)-carboxamide-3',6-dioxaoctanyl]carbamoyl-ω-methyl-poly(ethylene glycol) (2KPEG-DMG) and the like can be mentioned. Preferred PEG lipid includes PEG-DGA, PEG-DAA, PEG-PE, PEG-Cer, and a mixture of these, more preferably, a PEG-DAA conjugate selected from the group consisting of a PEG-didecyl oxypropyl conjugate, a PEG-dilauryl oxypropyl conjugate, a PEG-dimyristyl oxypropyl conjugate, a PEG-dipalmityl oxypropyl conjugate, a PEG-distearyl oxypropyl conjugate, and mixtures thereof.

In addition to the methoxy group, the maleimide group, N-hydroxysuccinimidyl group and the like for binding the T cell targeting ligand described later can be used as the free end of PEG. For example, SUNBRIGHT DSPE-0201MA or SUNBRIGHT DSPE-0201MA (NOF) can be used as a PEG lipid having a functional group for binding a T cell-targetting ligand (sometimes to be referred to as "terminal reactive PEG lipid" in the present specification).

The ratio (mol %) of the PEG lipid to the total lipids present in the lipid nanoparticle of the present invention may be, for example, about 0% to about 20%, preferably about 0.1% to about 5%, more preferably about 0.7% to about 2%.

The ratio (mol %) of the terminal reactive PEG lipid in the above-mentioned total PEG lipids is, for example, about 10% to about 100%, preferably about 20% to about 100%, more preferably about 30% to about 100%.

Only one kind of the above-mentioned PEG lipid may be used or two or more kinds thereof may be used in combination. When multiple PEG lipids are used, the ratio of the whole PEG lipid is preferably as mentioned above.

The lipid nanoparticle of the invention is used for gene transfer and expression of CAR or exogenous TCR in immune cells, particularly in T cells which are responsible for cellular immunity among acquired immunity, NK cells, monocytes, macrophages, dendritic cells, and the like which are responsible for innate immunity, and NKT cells which are T cells having the properties of NK cell. Therefore, the lipid nanoparticle of the present invention may further contain a ligand that may target the lipid nanoparticle to immunocytes, particularly T cells, for efficient delivery to targeted immunocytes, particularly in vivo.

(d) Ligand Capable of Targetting Lipid Nanoparticle to T Cell

The ligand capable of targetting the lipid nanoparticle of the present invention to T cells is not particularly limited as long as it can specifically recognize surface molecules that are specifically or highly expressed in T cells. Preferably, it includes those containing one or more antigen binding domains of antibodies against CD3, CD4, CD8 or CD28, and more preferably, it includes those containing antigen binding domains of anti-CD3 antibody and/or anti-CD28 antibody. A particularly preferable example for in vivo delivery to T cells is one containing only the antigen-binding domain of an anti-CD3 antibody. Here, the "antigen-binding domain" is synonymous with the antigen-binding domain that constitutes the above-mentioned CAR. However, since CAR needs to be prepared as a nucleic acid encoding same, restrictions occur and single-chain antibodies are generally used in many cases. Since the antigen-binding domain as a T cell targeting ligand is contained in a protein state in the lipid nanoparticle of the present invention, not only single-chain antibodies, but also any other antibody fragments, such as complete antibody molecules, Fab, $F(ab')_2$, Fab', Fv, reduced antibody (rIgG), dsFv, sFv, diabody, triabody, and the like, can also be used preferably. Fab' without an Fc moiety can be preferably used, especially for delivery to the target immunocyte in vivo. These antibody fragments can be prepared by treating the complete antibody (e.g., IgG) with a reducing agent (e.g., 2-mercaptoethanol, dithiothreitol) or peptidase (e.g., papain, pepsin, ficin), or by using a genetic recombination operation.

When the T-cell targetting ligand is a complete antibody molecule, commercially available anti-CD3, CD4, CD8, CD28 antibodies, etc. can be used, or the ligand can be isolated from the culture of the cells producing the antibody. On the other hand, when the ligand is any one of the aforementioned antigen-binding domain (antibody fragment), the nucleic acid encoding the antigen-binding domain, such as anti-CD3, CD4, CD8, CD28 antibodies, etc., is isolated in the same way as in the nucleic acid encoding the antigen-binding domain constituting the said CAR is obtained, and the antigen-binding domain can be recombinantly produced using the same.

In the lipid nanoparticle of the present invention, the T cell-targetting ligand may bind to the outer shell in any manner as long as it is present on the surface of the lipid nanoparticle. For example, when a terminally reactive PEG lipid is contained as a non-cationic lipid, the ligand can be added to the terminal of PEG. For example, lipid nanoparticles labeled with a ligand (antibody) can be prepared by reacting a PEG lipid (e.g., SUNBRIGHT DSPE-0200MA) with a maleimide group introduced into the terminal with the thiol group of the above-mentioned reducing antibody (sometimes referred to as "antibody-LNP").

When the lipid nanoparticle of the present invention is used for gene transfer to immunocytes other than T cells, such as NK cells and dendritic cells, the lipid nanoparticle can be delivered efficiently even in the absence of a ligand for targeting to those immune cells on the surface of the lipid nanoparticle. It may also have, on the surface of the lipid nanoparticle, a suitable targetting ligand for molecules expressed on the surface of each immune cell. For example, in the case of NK cells, those containing antigen-binding domains of antibodies against CD16 and CD56 can be mentioned, though unlimitatively.

2. Production of Lipid Nanoparticle of the Present Invention

The lipid nanoparticle of the present invention can be produced, for example, by the method described in U.S. Pat. No. 9,404,127. When the lipid nanoparticle further contains a T cell-targetting ligand, it can be produced by chemically binding the T cell-targeting ligand after preparation of the lipid nanoparticles. As described in WO 2016/021683, for example, an organic solvent solution of the above-mentioned components (b) and (c) is prepared, the organic solvent solution is mixed with water or a buffer solution of (a) to prepare lipid nanoparticles, and then the T cell-targetting ligand is chemically bound to produce same. The mixing ratio (molar ratio) of cationic lipid, phospholipid, cholesterol, and PEG lipid is, for example, 40 to 60:0 to 20:0 to 50:0 to 5, but the ratio is not limited thereto. When PEG lipid is blended as a non-cationic lipid and a T cell-targetting ligand is added to the terminal of PEG, the mixing ratio (molar ratio) of the PEG lipid and the ligand may be, for example, 20:1 to 1:20. The above-mentioned PEG lipid may contain terminal reactive PEG at a ratio (mol %) of about 10% to about 100%. The above-mentioned mixing can be conducted using a pipette, a micro fluid mixing system (e.g. Asia microfluidic system (Syrris)) or Nanoassemblr (Precision Nanosystems)). The obtained lipid particles may be subject to purification by gel filtration, dialysis or sterile filtration.

The concentration of the total lipid component in the organic solvent solution is preferably 0.5 to 100 mg/mL.

As the organic solvent, for example, methanol, ethanol, 1-propanol, 2-propanol, 1-butanol, tert-butanol, acetone, acetonitrile, N,N-dimethylformamide, dimethylsulfoxide, or a mixture thereof can be recited. The organic solvent may contain 0 to 20% of water or a buffer solution. As the buffer solution, acidic buffer solutions (e.g. acetate buffer solution, citrate buffer solution) or neutral buffer solutions (e.g. 4-(2-hydroxyethyl)-1-piperazineethanesulfonic acid, (HEPE) buffer solution, tris(hydroxymethyl)aminomethane (Tris) buffer solution, a phosphate buffer solution, phosphate buffered saline (PBS)) can be recited.

In the case where a micro fluid mixing system is used for mixing, preference is given to mixing 1 part by volume of an organic solvent solution with 1 to 5 parts by volume of water or a buffer solution. In addition, in said system, the flow rate of the mixture (a mixture solution of an organic solvent solution and water or a buffer solution) is preferably 0.1 to 10 mL/min, and the temperature preferably is 4 to 45° C.

When a lipid particle dispersion is produced as described above, the dispersion containing components (a) to (d) can be produced by adding a nucleic acid encoding CAR or exogenous TCR to water or buffer solution. Addition of the nucleic acid in a manner to render the concentration thereof the active ingredient in water or a buffer solution 0.05 to 2.0 mg/mL is preferable.

In addition, the lipid nanoparticle of the present invention can also be produced by admixing a lipid particle dispersion with the nucleic acid by a method known per se.

In the lipid nanoparticle of the present invention, the content of the nucleic acid is preferably 1-20 wt %. The content can be measured using Quant-iT™ Ribogreen® (Invitrogen) In the lipid nanoparticle of the present invention, the encapsulation ratio of the nucleic acid can be calculated based on the difference in fluorescence intensity in the presence or absence of the addition of a surfactant (e.g., Triton-X100).

A dispersion medium can be substituted with water or a buffer solution by dialysis. For the dialysis, ultrafiltration membrane of molecular weight cutoff 10 to 20K is used to carry out at 4° C. to room temperature. The dialysis may repeatedly be carried out. For the dialysis, tangential flow filtration may be used.

The ratio (weight ratio) of the nucleic acid and the lipid in the lipid nanoparticle of the present invention obtained as mentioned above is about 0.01 to about 0.2.

The average particle size of the lipid nanoparticle of the present invention is preferably 10 to 200 nm. The average particle size of the lipid particles can be calculated using, for example, Zetasizer Nano ZS (Malvern Instruments) on cumulant analysis of an autocorrelation function.

3. Ex Vivo Immunocyte Introduced with the Lipid Nanoparticle of the Present Invention The present invention provides a method for producing an ex vivo immunocyte expressing CAR or exogenous TCR by contacting immunocytes collected from living organisms (to be also referred to as "ex vivo immunocyte" in the present specification) with the lipid nanoparticle of the present invention and introducing a nucleic acid encoding the CAR or exogenous TCR into the T cells, and ex vivo immunocytes obtained by the method. As used herein, the "immunocyte" is not particularly limited as long as it is a cell capable of damaging the target cell (pathogenic cell) such as cancer cell and the like by some action mechanism (i.e., immune effector cell). Examples thereof include T cells that are responsible for cellular immunity among acquired immunities, NK cell, monocyte, macrophage, dendritic cell, etc. that are responsible for innate immunity, and NKT cells that are T cells with properties of NK cells. In one-preferred embodiment, the immunocyte may be a T cell. T cell collected from a living organism is also referred to as "ex vivo T cell" in the present specification. In another preferred embodiment, the immunocyte may be responsible for innate immunity such as NK cell, macrophage, dendritic cell, and the like. T cells are considered to be at considerable risk of causing GVHD by allogeneic (allo) transplantation even if HLA type matches, whereas allo-NK cells, etc. are considered not to cause GVHD. Therefore, the preparation of various HLA-type allo ex vivo immunocytes permits use off-the-shelf. CAR-NK cell is described in, for example, US2016/0096892, Mol Ther. 25(8): 1769-1781 (2017) and the like, and CAR-dendritic cell, CAR-macrophage and the like are described in, for example, WO 2017/019848, eLIFE. 2018 e36688 and the like.

In another aspect, the present invention provides a composition for inducing the expression of a CAR or exogenous TCR containing the lipid nanoparticle of the present invention.

The immunocyte (e.g., T cell) into which the lipid nanoparticle of the present invention is introduced may be an isolated particular immunocyte (e.g., T cell), or, for example, a non-uniform cell population such as, lymphocytes and progenitor cells of lymphocytes including pluripotent cells as long as it is a cell population containing immunocyte (e.g., T cell) or a progenitor cell thereof. In the present invention, the "lymphocyte" means one of the subtypes of leukocyte in the immune system of vertebrates. Examples of the lymphocyte include T cell, B cell, and natural killer cell (NK cell), preferably, isolated and purified T cell. In the present invention, the "T cell" is one type of leukocyte found in lymphatic organs, peripheral blood, and the like, and refers to one category of lymphocyte characterized by differentiation and maturation mainly in the thymus gland and expression of TCR. Examples of the T cell that can be used in the present invention include cytotoxic T cell (CTL), which is a CD8-positive cell, helper T cell, which is a CD4-positive cell, regulatory T cell, and effector T cell, and preferably, cytotoxic T cell.

The aforementioned lymphocyte can be collected from, for example, peripheral blood, bone marrow, and umbilical cord blood of a human or non-human mammal. When ex vivo immunocyte (e.g., ex vivo T cell) introduced with the lipid nanoparticle of the present invention is used for the treatment of diseases such as cancer, the cell population is preferably harvested from the person to be treated or a donor with the HLA type matching with that of the subject to be treated.

Examples of the lymphocyte progenitor cell, including pluripotent cell, include embryonic stem cell (ES cell), induced pluripotent stem cell (iPS cell), embryonic cancer cell (EC cell), embryonic germ cell (EG cell), hematopoietic stem cell, pluripotent progenitor cell that has lost self-renewal potential (multipotent progenitor: MMP), common myelo-lymphoid progenitor cell (MLP), myeloid progenitor cell (MP), granulocyte mononuclear progenitor cell (GMP), macrophage-dendritic cell progenitor cell (MDP), dendritic cell progenitor cell (DCP) and the like. Undifferentiated cells such as pluripotent cell and the like can be differentiated into various immunocytes, for example, T cell, by a method known per se.

There is no particular limitation on the method of contacting ex vivo immunocytes with the lipid nanoparticle of the present invention, and, for example, the lipid nanoparticle of the present invention may be added to a typical medium for immunocyte. Alternatively, to increase the introduction efficiency, for example, the calcium phosphate co-precipitation method, PEG method, electroporation method, microinjection method, lipofection method, and the like may be used in combination.

When the lipid nanoparticle of the present invention particularly contains a nucleic acid encoding exogenous TCR as an active ingredient, the expression of endogenous TCR $\alpha$ chain and TCR $\beta$ chain that are inherently expressed by the T cell may be suppressed by siRNA from the viewpoint of an increase in the expression of exogenous TCR, inhibition of the appearance of mispaired TCR, or inhibition of self-reactivity. When the above-mentioned nucleic acid is applied to the method, to avoid the effect of siRNA on exogenous TCR, the base sequence of a nucleic acid encoding TCR is preferably a sequence (codon conversion type sequence) different from the base sequence corresponding to RNA on which siRNA, which suppresses the expression of endogenous TCR$\alpha$ and TCR$\beta$ chains, acts. The method therefor is described, for example, in WO 2008/153029. The aforementioned base sequence can be produced by introducing a silent mutation into a naturally acquired nucleic acid encoding TCR or chemically synthesizing an artificially designed nucleic acid. Alternatively, to avoid mispair with the endogenous TCR chain, a part or all of the constant regions of the nucleic acid encoding the exogenous TCR may be replaced with a constant region derived from an animal other than human, for example, a mouse.

4. Medicament Containing the Lipid Nanoparticle of the Present Invention, or Ex Vivo Immunocyte Introduced with the Lipid Nanoparticle The present invention provides a medicament containing the lipid nanoparticle of the present invention, or ex vivo immunocyte (e.g., ex vivo T cell) introduced with the lipid nanoparticle (hereinafter to be abbreviated as "the medicament of the present invention").

(4-1. Medicament Containing Ex Vivo Immunocyte Introduced with the Lipid Nanoparticle of the Present Invention)

By expressing CAR or exogenous TCR, an immunocyte (e.g., T cell) introduced with the lipid nanoparticle of the present invention can specifically recognize cells expressing surface antigen specifically recognized by CAR or exogenous TCR and kill them (e.g., induction of apoptosis). Therefore, by containing, as a surface antigen, a nucleic acid encoding CAR or exogenous TCR that recognizes a surface molecule specifically expressed or showing enhanced expression in a disease cell, such as a cancer cell, as an active ingredient, ex vivo immunocyte introduced with the lipid nanoparticle of the present invention can be used for the prophylaxis or treatment of diseases such as cancer and the like, and can be safely administered to mammals (human or other mammal (e.g., mouse, rat, hamster, rabbit, cat, dog, bovine, sheep, monkey, preferably human)).

(4-2. Medicament Containing the Lipid Nanoparticle of the Present Invention)

The medicament of the present invention containing the lipid nanoparticle of the present invention is preferably prepared as a pharmaceutical composition by mixing the lipid nanoparticle with known pharmaceutically acceptable carriers (including excipient, diluent, bulking agent, binder, lubricant, flow aid, disintegrant, surfactant, and the like) and conventional additives, and the like. The excipients are well known to those of ordinary skill in the art and include, for example, phosphate-buffered saline (e.g., 0.01M phosphate, 0.138M NaCl, 0.0027M KCl, pH 7.4), aqueous solutions containing mineral acid salts such as hydrochloride, hydrobromate, phosphate, sulfate, and the like, saline solutions, solutions of glycol, ethanol, and the like, and salts of organic acids such as acetate, propionate, malonate, benzoate, and the like. In addition, adjuvants such as wetting agent or emulsifier, and pH buffering agents can also be used. In addition, preparation adjuvants such as suspension agent, preservative, stabilizer and dispersing agent may also be used. Alternatively, the above-mentioned pharmaceutical composition may be in a dry form which is reconstituted with a suitable sterile liquid prior to use. The pharmaceutical composition may be orally or parenterally administered systemically or topically, depending on the form in which it is prepared (oral agents such as tablet, pill, capsule, powder, granule, syrup, emulsion, suspension and the like; parenteral agents such as injection, drip transfusion, external preparation, suppository and the like). For parenteral administration, intravenous administration, intradermal administration, subcutaneous administration, rectal administration, transdermal administration and the like are available. When used in an injectable form, acceptable buffering agent, solubilizing agent, isotonic agent and the like can also be added.

The dosage of the medicament of the present invention containing the lipid nanoparticle of the present invention is, for example, in the range of 0.001 mg to 10 mg as the amount of a nucleic acid encoding CAR or exogenous TCR, per 1 kg body weight per dose. For example, when administered to a human patient, the dosage is in the range of 0.0001 to 50 mg for a patient weighing 60 kg. The above-mentioned dosage is an example, and the dosage can be appropriately selected according to the type of nucleic acid to be used, administration route, age, weight, symptoms, etc. of the subject of administration or patient.

By administration to a mammal (e.g., human or other mammal (e.g., mouse, rat, hamster, rabbit, cat, dog, bovine, sheep, monkey), preferably, human), the medicament of the present invention containing the lipid nanoparticle of the present invention can induce the expression of CAR or exogenous TCR in immunocytes, e.g., T cell (to be also referred to as "in vivo immunocyte" or "in vivo T cell" in the present specification) in the body of the animal. The in vivo immunocyte specifically recognizes cancer cells and the like expressing surface antigen targeted by CAR or exogenous TCR and kills the diseased cells, thereby demonstrating a prophylactic or therapeutic effect against the disease.

In the case of a medicament containing, as an active ingredient, ex vivo immunocyte introduced with the lipid nanoparticle of the present invention, the immunocyte may be cultured and/or stimulated using an appropriate medium and/or stimulating molecule before administration to the subject. The stimulating molecule includes, but is not limited to, cytokines, suitable proteins, and other components. In the case of T cell, examples of cytokine include IL-2, IL-7, IL-12, IL-15, IFN-γ and the like, and preferably, IL-2 can be used. While the concentration of IL-2 in a medium is not particularly limited, it is, for example, preferably 0.01 to $1\times10^5$ U/mL, more preferably 1 to $1\times10^4$ U/mL. Examples of the suitable protein include CD3 ligand, CD28 ligand, and anti-IL-4 antibody. Lymphocyte stimulating factors such as lectins can also be added. In addition, serum or plasma may be added to the medium. While the amounts of these to be added to the media are not particularly limited, 0% by volume to 20% by volume is exemplified, and the amounts of serum or plasma to be used can be changed according to the culture stage. For example, the serum or plasma concentration may be reduced in a stepwise manner. The serum and plasma may be derived from either self or non-self, but those derived from self are preferable from the aspect of safety.

A medicament containing ex vivo immunocyte introduced with the lipid nanoparticle of the present invention as an active ingredient is preferably administered parenterally to the subject. Parenteral methods of administration include intravenous, arterial, intramuscular, intraperitoneal, and subcutaneous administrations. While the dosage is selected according to the condition, body weight, age, etc. of the subject, administration is performed to a subject of 60 kg body weight to generally achieve $1\times10^6$–$1\times10^{10}$ cells, preferably $1\times10^7$–$1\times10^9$ cells, more preferably $5\times10^7$–$5\times10^8$ cells, per dose. The medicament may be administered as a single dose or in multiple doses. The inventive medicament containing ex vivo immunocyte introduced with the lipid nanoparticle of the present invention as an active ingredient may be in a known form suitable for parenteral administration such as injection or infusion agent. The medicament may contain a pharmaceutically acceptable excipient as appropriate. The pharmaceutically acceptable excipient includes those described above. The medicament may contain saline, phosphate-buffered saline (PBS), medium, etc. to stably maintain the cells. The medium is not particularly limited, and examples thereof include, but are not limited to, RPMI, AIM-V, X-VIVO10, and the like. In addition, a pharmaceutically acceptable carrier (e.g., human serum albumin), preservative, and the like may be added to the medicament for the purpose of stabilization.

The medicament of the present invention may be a prophylactic or therapeutic drug for cancer. The cancer to be the application target of the medicament of the present invention is not particularly limited. Examples thereof include, but are not limited to, acute lymphocytic cancer, alveolar rhabdomyosarcoma, bladder cancer, bone cancer, brain cancer (e.g., medulloblastoma), breast cancer, anus, anal canal or anorectal cancer, cancer of the eye, cancer of the interhepatic bile duct, joint cancer, cervical, gallbladder or pleural cancer, nose, nasal cavity or middle ear cancer, oral cancer, vulvar cancer, chronic myelogenous cancer, colon cancer, esophageal cancer, cervical cancer, fibrosarcoma, gastrointestinal carcinoid tumor, head and neck cancer (e.g., head and neck squamous cell carcinoma), hypopharyngeal cancer, kidney cancer, laryngeal cancer, leukemia (e.g., acute lymphoblastic leukemia, acute lymphocytic leukemia, chronic lymphocytic leukemia, acute myeloid leukemia), liquid tumor, liver cancer, lung cancer (e.g., non-small cell lung cancer), lymphoma (e.g., Hodgkin lymphoma, non-Hodgkin lymphoma, diffuse large B cell lymphoma, follicular lymphoma), malignant mesothelioma, mastocytoma, melanoma, multiple myeloma, nasopharyngeal cancer, ovarian cancer, pancreatic cancer; peritoneal, omentum and mesenteric cancer; pharyngeal cancer, prostate cancer, rectal cancer, renal cancer, skin cancer, small intestine cancer, soft tissue cancer, solid tumor, gastric cancer, testicular cancer, thyroid cancer, ureteral cancer and the like.

The present invention is explained in more detail in the following by referring to Examples which are mere exemplifications and do not limit the present invention.

EXAMPLE

Example 1

(Reduction Treatment of Antibody)

9.21 mg/ml anti-CD3 antibody (Bio X Cell) (111 μl) was mixed with 10 mM DTT aqueous solution (12.3 μl). Similarly, 6.73 mg/ml IgG2a antibody (Bio X Cell) (149 μl) was mixed with 10 mM DTT aqueous solution (16.6 μl). The mixture of each antibody and DTT was mixed by vortex to carry out reaction at room temperature for 30 min. The reaction mixture was fractionated by HPLC (column: TSKgel G2000SWXL 7.8 mm×30 cm, TOSOH, mobile phase: PBS) to give a fraction solution containing the reduced antibody. The fraction solution was ultracentrifuged using Amicon 0.5 ml-10K. The concentrations of the antibody protein and thiol group in the concentrates were measured by absorbance at 230 nm and a fluorescence colorimetric reaction with N-(7-dimethylamino-4-methylcoumarin-3-yl) maleimide (DACM), respectively. The yield of the reduced anti-CD3 antibody was 176 μl with protein concentration 1.75 mg/ml, thiol group concentration 5.14 μM, and the yield of the reduced IgG2a antibody was 86 μl with protein concentration 5.19 mg/ml, thiol group concentration 45.1 μM.

Example 2

(Preparation of Maleimide-LNP)

A lipid mixture (cationic lipid:DPPC:Cholesterol:SUNBRIGHT GM-020:SUNBRIGHT DSPE-020 MA=60:10.6:28:1.4:1, molar ratio) was dissolved in 90% EtOH, 10% water to give a 7.0 mg/ml lipid solution. As a cationic lipid, 3-((5-(dimethylamino)pentanoyl)oxy)-2,2-bis (((3-pentyloctanoyl)oxy)methyl)propyl 3-pentyloctanoate (compound 7) described in WO 2016/021683 and N,N,N-trimethyl-5-oxo-5-(3-((3-pentyloctanoyl)oxy)-2,2-bis(((3-pentyloctanoyl)oxy)methyl)propoxy)pentane-1-aminium iodide (compound 8) were mixed at 59.1:0.9 (molar ratio) and used. mRNA encoding CD19-targeted CAR having 4-1BB and CD3ζ as intracellular signal transduction domains were dissolved in 10 mM 2-morpholinoethanesulfonic acid (MES) buffer (pH 5.0) to give a 0.2 mg/ml nucleic acid solution. The obtained lipid solution and nucleic acid solution were mixed at room temperature by a Nanoassemblr apparatus (Precision Nanosystems) at a flow rate ratio of 3 ml/min:6 ml/min to give a dispersion containing the composition. The obtained dispersion was dialyzed using Slyde-A-Lyzer (20 k fraction molecular weight, Thermo Scientific) against water at room temperature for 1 hr, and against PBS at 4° C. for 48 hr. Successively, the dialysate was filtered through a 0.2 μm syringe filter (Iwaki) and preserved at 4° C.

Example 3

(Binding Reaction of Reduced Antibody and Maleimide-LNP)

Maleimide-LNP dispersion was mixed with reduced antibody solution to 1/20 molar concentration of reduced antibody to maleimide, and allowed to stand at room temperature for 4 hr. Thereafter, the mixture was stored at 4° C. until the purification step.

Example 4

(Gel Filtration Purification of Antibody-LNP)

A reaction mixture of a reduced antibody and Maleimide-LNP was loaded on a gel filtration column Sepharose CL-4B (Cat No. 17-0150-01/GE Healthcare), and fractionated with D-PBS(−) as a mobile phase. Successively, the protein concentration of each fraction was measured to identify the fraction containing the antibody-LNP of interest. The antibody-LNP was filtered through a 0.2 μm syringe filter and stored at 4° C.

Example 5

(Ex Vivo Transfection of CD8+ T Cell)

Spleen is collected from C57BL/6J mouse and dispersed in ACK lysing buffer (Biosource) to give a mouse splenocyte. The obtained mouse splenocyte is cultured in complete RPMI 1640 medium containing 1 ng/ml interleukin 7 and 2 μg/ml concavalin A for 2 days, and mouse CD8+ T cells are separated by removing dead cells using Ficoll density gradient centrifugation and treatment using CD8 Negative Isolation Kit (Stemcell Technologies). The obtained mouse CD8+ T cells are dispersed and cultured in complete RPMI 1640 medium containing 10 ng/ml interleukin 2 and antibody-LNP to transfect the mouse CD8+ T cells with CAR or exogenous TCR.

In the same manner, CD8+ T cells are separated from purchased cultured human primary T cells and human CD8+ T cells are transfected with CAR or exogenous TCR.

Example 6

(In Vitro Cytotoxicity Evaluation of CAR-T Cell)

The human chronic myeloid leukemia cell line K562 cells forcibly expressing CD19, which are cells to be evaluated for cytotoxicity, are labeled with a membrane dye PKH-26 (Sigma-Aldrich), washed with RPMI medium containing 10% fetal calf serum, dispersed at 1×10^5 cells/ml in the medium and cultured. The labeled cytotoxicity evaluation cells are dispensed in a 96-well plate and cultured. The cells are mixed with CAR-T cells, cultured at 37° C. for 3 hr, stained with Annexin V-Brilliant Violet 421 (BioLegend), and flow cytometry is performed to quantify apoptotic cells.

Example 7

(In Vivo Anti-Cancer Activity Evaluation Test)

K562-CD19 cells stably expressing luciferase are administered to 6-week-old NOD-SCID mice from the tail vein, and the mice are bred for a period of 1 week to prepare a mouse hematologic cancer model. Successively, 1×10^6 human CAR-T cells obtained by transfecting a nucleic acid encoding CAR ex vivo using antibody-LNP are administered once per week for 3 weeks by administration via tail vein. A decrease in the cancer cells by CAR-T cells is evaluated by a measurement using in vivo luminescence imaging system IVIS (PerkinElmer).

Example 8

(Preparation of Maleimide-LNP Using Cationic Lipid)

A lipid mixture (cationic lipid: DPPC:Cholesterol:SUNBRIGHT GM-020:SUNBRIGHT DSPE-020 MA=60:10.6:28:1.4:1, molar ratio) was dissolved in 90% EtOH, 10% 25 mM acetate buffer pH 4.0 to give a 10 mg/ml lipid solution. As a cationic lipid, 3-((5-(dimethylamino)pentanoyl)oxy)-2,2-bis(((9Z)-tetradeca-9-enoyl oxy)methyl)propyl (9Z)-tetradeca-9-enoate (compound 12), 2-(((4-(dimethylamino)butanoyl)oxy)methyl)-2-((dodecanoyloxy)methyl)propane-1,3-diyl (9Z,9'Z)bis-tetradeca-9-enoate (compound 21), and 2-(((4,5-dibutylnonanoyl)oxy)methyl)-2-(((5-(dimethylamino)pentanoyl)oxy)methyl)propane-1,3-diyl didecanoate (compound 35) were used. pcDNA3.1-hCD19CAR encoding CD19-targeted CAR was dissolved in 10 mM 2-morpholinoethanesulfonic acid (MES) buffer (pH 5.5) to give a 0.2 mg/ml nucleic acid solution. pcDNA3.1-hCD19CAR was produced by integrating the CD19 IgG4 28z sequence cited from WO 2013/126712 into the multi cloning site of pcDNA3.1 (Thermo Fisher Scientific). The obtained lipid solution and nucleic acid solution were mixed at room temperature by a Nanoassemblr apparatus (Precision Nanosystems) at a flow rate ratio of 3 ml/min:6 ml/min to give a dispersion containing the composition. The obtained dispersion was dialyzed using Slyde-A-Lyzer (20 k fraction molecular weight, Thermo Scientific) against water at room temperature for 1 hr, and against PBS at 4° C. for 48 hr. Successively, the dialysate was filtered through a 0.2 μm syringe filter (Iwaki) and stored at 4° C.

(Measurement of Nucleic Acid Concentration of Maleimide-LNP, and Calculation of Assumed Maleimide Concentration)

Maleimide-LNP was dissolved in 0.5% Triton X-100, and the pDNA concentration was measured using Quant-iT™ PicoGreen™ dsDNA Assay Kit (Thermo Fisher Scientific). The pDNA concentration measured without adding Triton X-100 was taken as the concentration of pDNA not encapsulated in LNP, and the encapsulation ratio of pDNA in LNP was calculated. The assumed maleimide concentration was calculated by multiplying the measured pDNA concentration by the charging ratio of maleimide-PEG-lipid (DSPE-020MA). The obtained values are shown in Table 1.

TABLE 1

| Maleimide-LNP | pDNA concentration (μg/ml) | pDNA encapsulation ratio | assumed maleimide concentration (μM) |
|---|---|---|---|
| compound 12-pcDNA3.1-hCD19CAR | 193 | 94% | 66.0 |
| compound 21-pcDNA3.1-hCD19CAR | 253 | 89% | 86.2 |
| compound 35-pcDNA3.1-hCD19CAR | 169 | 95% | 57.7 |

(Binding Reaction of Two Kinds of Mixed Reduced Antibodies and Maleimide-LNP)

Equal amounts of an anti-human CD3 antibody (BE0001-2, BioXCell) and an anti-human/monkey CD28 antibody (BE0248, BioXCell) reduced with DTT were mixed at 1/20 molar quantity to maleimide of maleimide-LNP. The concentrations and volumes of maleimide-LNP and reduced antibodies are shown in Table 2. The mixture was allowed to stand at room temperature for 4 hr and then stored at 4° C. until the purification step.

TABLE 2

| Maleimide-LNP | assumed maleimide concentration (μM) | LNP volume (ml) | mixed antibody weight (μg) | mixed antibody solution volume (μl) |
|---|---|---|---|---|
| compound 12-pcDNA3.1-hCD19CAR | 66.0 | 1.5 | 742 | 176 |
| compound 21-pcDNA3.1-hCD19CAR | 86.2 | 0.27 | 175 | 43 |
| compound 35-pcDNA3.1-hCD19CAR | 57.7 | 0.3 | 130 | 32 |

(Gel Filtration Purification of Antibody-LNP)

A reaction mixture of a reduced antibody and Maleimide-LNP was loaded on a gel filtration column Sepharose CL-4B (Cat No. 17-0150-01/GE Healthcare), and fractionated with D-PBS(−) as a mobile phase. Successively, the protein concentration of each fraction was measured to identify the fraction containing the antibody-LNP of interest. The antibody-LNP was filtered through a 0.2 μm syringe filter and stored at 4° C. The particle size of the obtained antibody-LNP was measured by Zetasizer Nano ZS (Malvern Panalytical). The concentrations of the nucleic acid and antibody protein were measured using the Quant-iT™ PicoGreen™ dsDNA Assay Kit (Thermo Fisher Scientific) and ATTO-TAG™ FQ Amine-Derivatization Kit (Thermo Fisher Scientific), respectively. The values of each analysis results are shown in Table 3.

TABLE 3

| example of antibody-LNP | particle size (nm) | nucleic acid concentration (μg/ml) | antibody concentration (μg/ml) |
|---|---|---|---|
| hCD3/hCD28-compound 12-pcDNA3.1-hCD19CAR | 119 | 69 | 94 |
| hCD3/hCD28-compound 21-pcDNA3.1-hCD19CAR | 95 | 65 | 82 |

TABLE 3-continued

| example of antibody-LNP | particle size (nm) | nucleic acid concentration (μg/ml) | antibody concentration (μg/ml) |
|---|---|---|---|
| hCD3/hCD28-compound 35-pcDNA3.1-hCD19CAR | 98 | 49 | 38 |

Example 9

(CD19 CAR Transfection Test to Cultured Human Primary T Cell Using Antibody-LNP)

Human Pan-T cells (AccuCell human peripheral blood pan-T cells, Negative selection) were prepared at $1.1\times10^6$ cells/ml with a medium and seeded in a 96-well plate at 90 μl/well. X-VIVO10 (Lonza) supplemented with recombinant IL-2 (Thermo Fisher Scientific) at a concentration of 30 ng/ml was used as the medium. Successively, 10 μl of antibody-LNP diluted with PBS to a concentration of 30 μg/ml pcDNA3.1-hCD19CAR was added to the medium, and the cells were cultured at 37° C. in a 5% $CO_2$ incubator for 3 days and 6 days.

(CD19CAR Expression Evaluation by Flow Cytometry)

Cultured human primary T cells cultured in a 96-well plate were collected in a 1.5 ml tube, Recombinant human CD19 protein, Fc Chimera Active, Biotin (Abcam) (2 μl) was added, and the mixture was allowed to stand on ice for 30 min. Successively, Cell Wash (BD) added with 200 μl of 1% FBS was added, the mixture was washed twice by centrifugation at 300×g for 5 min, the supernatant was removed and the cells were dispersed in 100 μl of 1% FBS, Cell Wash. To the cell dispersions was added 0.2 μl of Brilliant Violet 421 Streptavidin and, after mixing by pipetting, the dispersions were allowed to stand on ice for 30 min. The stained cells were washed three times with 200 μl of 1% FBS Cell Wash and centrifugation, filtered, dispersed in 200 μl of 1% FBS Cell Wash, and flow cytometric analysis was performed by LSRFortessa (BD).

The results of CD19 CAR expression analysis by Flow cytometric analysis in cultured human primary T cells transfected with hCD3/hCD28-compound 12-pcDNA3.1-hCD19CAR is shown in FIG. 1. The CD19 CAR-positive rate at 3 and 6 days after the addition of antibody-LNP was 51.9% and 41.7%, respectively, and CAR-positive cells were obtained with sufficient efficiency compared to gene transfer by virus vector.

Figure 2:
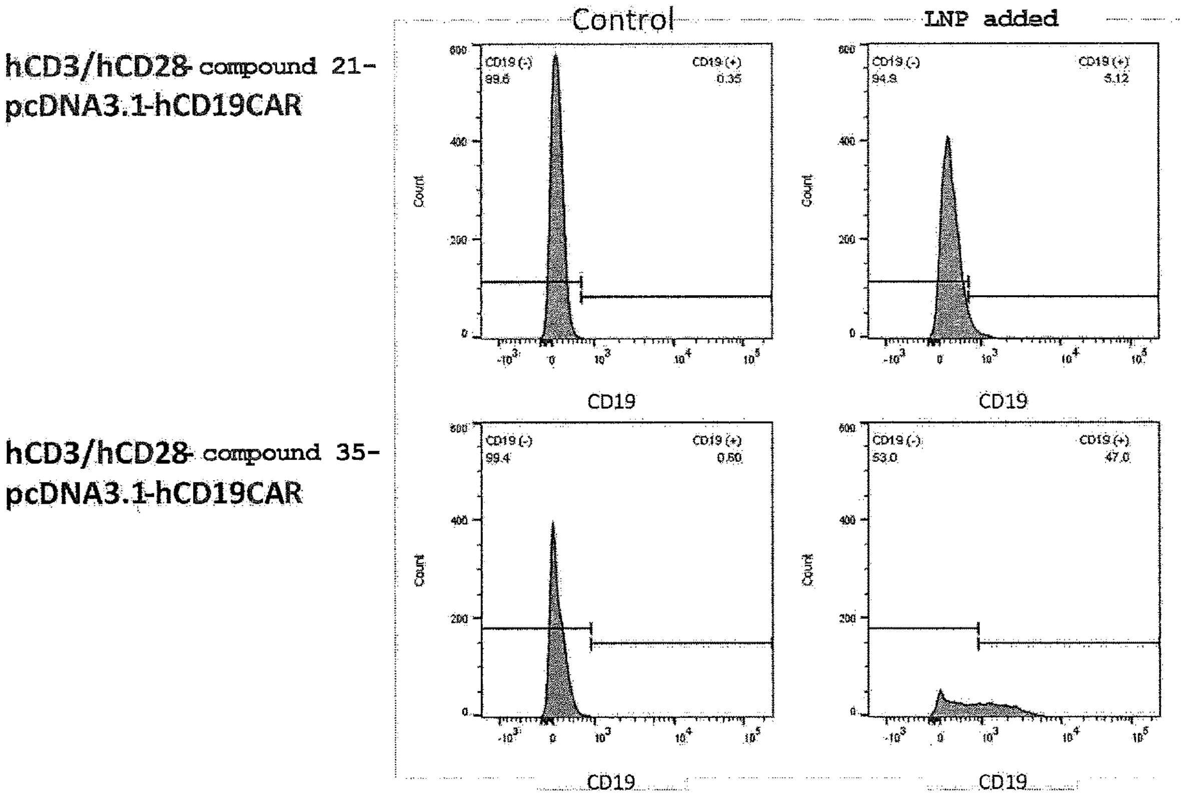
FIG. 2 shows the flow cytometry analysis results of CD19 CAR expression in cultured human primary T cells transfected with hCD3/hCD28-compound 21-pcDNA3.1-hCD19CAR and hCD3/hCD28-compound 35-pcDNA3.1-hCD19CAR.

The results of CD19 CAR expression analysis by Flow cytometric analysis in cultured human primary T cells transfected with hCD3/hCD28-compound 21-pcDNA3.1-hCD19CAR and hCD3/hCD28-compound 35-pcDNA3.1-hCD19CAR are shown in FIG. 2. The CD19 CAR-positive rates at 3 days after the addition of antibody-LNP were 5.12% and 47.0%, respectively.

Example 10

(Cancer Cytotoxicity Evaluation by Cultured Human Primary T Cell Transfected with CD19 CAR by Antibody-LNP)

Human pre B cell line NALM-6 and human Burkitt lymphoma cell line Daudi labeled with DELFIA cytotoxicity assay kit (Perkin Elmer) as target cells were seeded at a cell density of $1\times10^4$ cell/100 μl/well on a 96-well U bottom plate. As the medium, 10% FBS-containing RPMI (phenol red free) was used. Successively, cultured human primary T cells transfected with CD19CAR by hCD3/hCD28-compound 12-pcDNA3.1-hCD19CAR by the method described in another section (CD9CAR positive rate 3 days after addition of antibody-LNP: 19%) were added as an effector cell by dispersing in 100 μl of medium such that the cell number ratio with target cells was 0 to 16. Three hours after mixing the target cell and the effector cell, 20 μl of the culture supernatant was collected. Europium solution (Eu) (20 μl) was added to the collected culture supernatant, and the cytotoxicity rate was calculated from the intensity of fluorescence emitted by the complex of the chelating agent TDA and Eu released from the damaged target cell.

Figure 3:
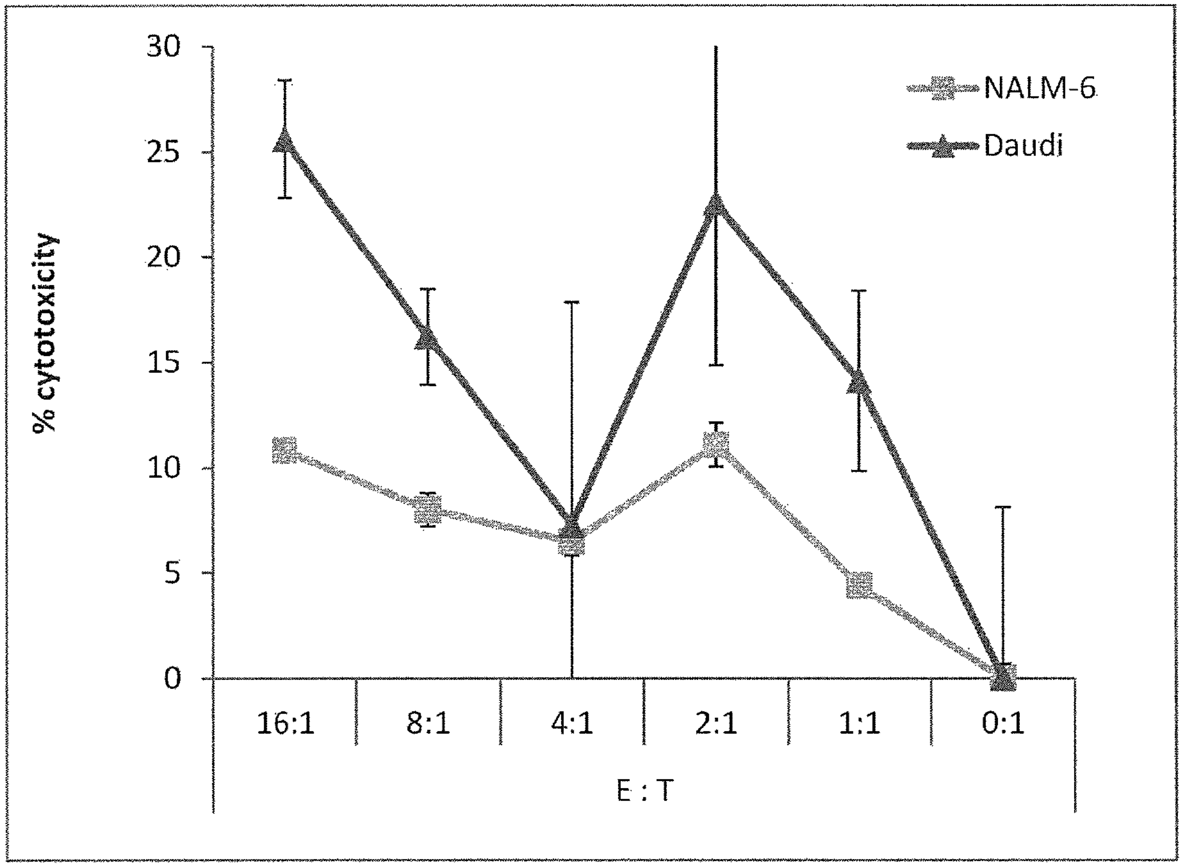
FIG. 3 shows the rate of cytotoxicity of Nalm-6 and Daudi by the addition of cultured human primary T cells transfected with CD19 CAR.

The cytotoxicity rate of Nalm-6 and Daudi due to the addition of human primary T cells transfected with CD19 CAR is shown in FIG. 3.

Example 11

(Preparation of Reduced Fab')

Reduced Fab' to be conjugated to Mleimide-LNP was prepared from anti-mouse CD3ε antibody (BE0001-1, BioXCell) and anti-mouse CD28 antibody (BE0015-1, BioXCell) using Pierce F(ab')2 Preparation Kit (Thermo Fisher Scientific). 1 ml of 1.75 mg/ml F(ab')2 was obtained from 7.86 mg/ml anti-mouse CD3s antibody (0.5 ml). 0.62 ml of 0.97 mg/ml F(ab')2 was obtained from 3.86 mg/ml anti-mouse CD28 antibody (0.5 ml). Each F(ab')2 was mixed with 2-aminoethanethiol p-toluenesulfonate as a reducing agent at a concentration of 40 mM and the mixture was allowed to stand at 37° C. for 1 hr. The obtained Fab' was purified by Zeba Spin Desalting Columns, 7K MWCO-0.5 ml (Thermo Fischer Scientific) and stored at 4° C. until reaction with Maleimide-LNP. The concentrations of the Fab' protein and thiol group were measured by absorbance at 230 nm and a fluorescence colorimetric reaction with N-(7-dimethylamino-4-methylcoumarin-3-yl)maleimide (DACM), respectively.

Example 12

(Binding Reaction of Reduced Fab' and Maleimide-LNP)

Reduced anti-mouse CD3εFab' and anti-mouse CD28 Fab' were mixed at 1/20 molar quantity to maleimide of maleimide-LNP prepared by the above-mentioned method. The mixture was allowed to stand at room temperature for 4 hr and then stored at 4° C. until the purification step.

Example 13

(Gel Filtration Purification of Reduced Fab'-LNP)

A reaction mixture of reduced Fab' and Maleimide-LNP was loaded on a gel filtration column Sepharose CL-4B (Cat No. 17-0150-01/GE Healthcare), and fractionated with D-PBS(−) as a mobile phase. Successively, the protein concentration of each fraction was measured to identify the fraction containing the Fab'-LNP of interest. The Fab'-LNP was filtered through a 0.2 μm syringe filter and stored at 4° C. The particle size of the obtained antibody-LNP was measured by Zetasizer Nano ZS (Malvern Panalytical). The concentrations of the nucleic acid and antibody protein were measured using the Quant-iT™ PicoGreen™ dsDNA Assay Kit (Thermo Fisher Scientific) and ATTO-TAG™ FQ Amine-Derivatization Kit (Thermo Fisher Scientific), respectively.

INDUSTRIAL APPLICABILITY

The lipid nanoparticle of the present invention can introduce CAR or exogenous TCR efficiently and T cell selectively not only ex vivo but also in vivo, and thus can provide CAR-T or TCR-T cell therapy with low production costs. In addition, since a virus vector is not used, the problem of antigenicity by viral proteins can be avoided, and it is extremely useful as a novel platform for cancer immunotherapy.

This application is based on a patent application No. 2017-252616 filed in Japan (filing date: Dec. 27, 2017), the contents of which are incorporated in full herein by reference.

The invention claimed is:

1. A medicament comprising a lipid nanoparticle, wherein the lipid nanoparticle comprises:

(a) a nucleic acid encoding a chimeric antigen receptor or an exogenous T cell receptor;

(b) a cationic lipid or a salt thereof, the cationic lipid being selected from the group consisting of compound 12 and compound 35:

(Compound 12)

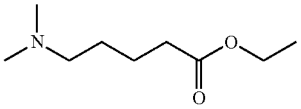

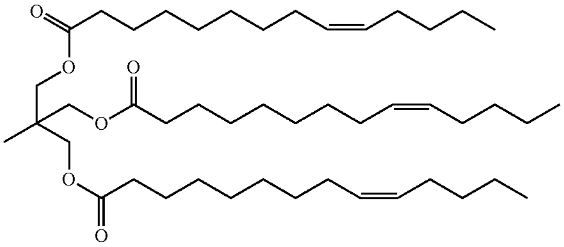

and (Compound 35)

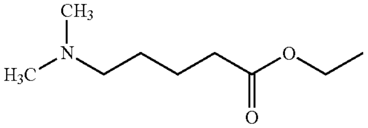

-continued

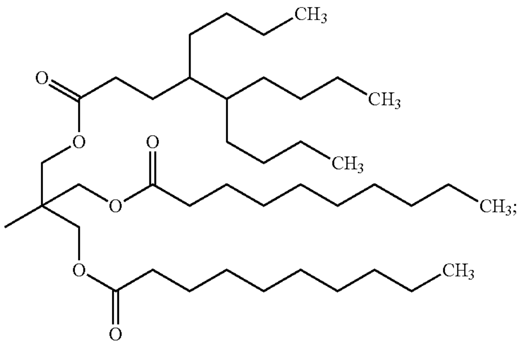

and (c) a non-cationic lipid, wherein a surface of the lipid nanoparticle has one or more ligands that target T cells and that provide increased expression of a chimeric antigen receptor or an exogenous T cell receptor encoded by a nucleic acid delivered by the lipid nanoparticle to the target T cells compared to the same lipid nanoparticle lacking the one or more ligands.

2. The medicament according to claim 1, wherein the medicament is a prophylactic or therapeutic drug for cancer.

3. The medicament according to claim 1, wherein the medicament introduces a chimeric antigen receptor or an exogenous T cell receptor gene into an in vivo T cell to induce an expression thereof.

4. The medicament according to claim 1, wherein the aforementioned nucleic acid is mRNA or DNA.

5. The medicament according to claim 1, wherein the aforementioned non-cationic lipid is phospholipid, cholesterol and/or PEG lipid.

6. The medicament according to claim 1, wherein the aforementioned ligands are comprising an antigen binding domain of one or more antibodies selected from the group consisting of an antibody against CD3, an antibody against CD4, an antibody against CD8 and an antibody against CD28.

7. The medicament according to claim 1, wherein the aforementioned ligands are comprising an antigen binding domain of an antibody against CD3 and/or an antibody against CD28.

8. The medicament according to claim 1, wherein the aforementioned cationic lipid is a compound 12:

(Compound 12)

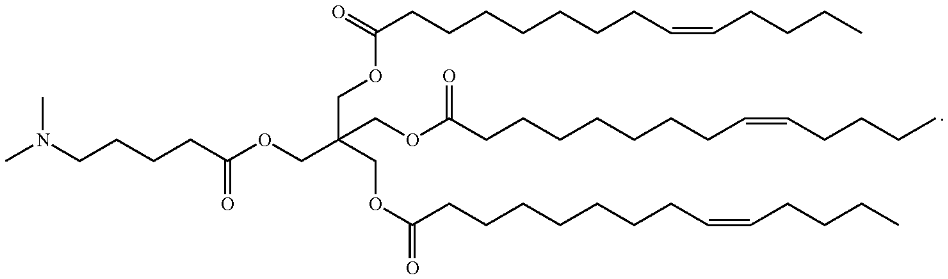

or a salt thereof.

9. The medicament according to claim 1, wherein the aforementioned cationic lipid is a compound 35:

(Compound 35)

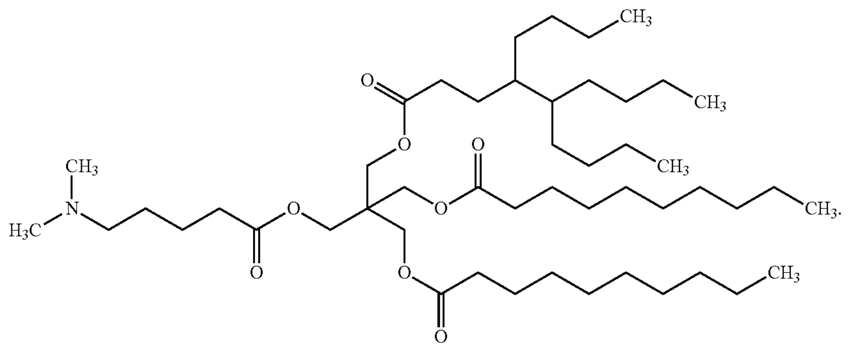

or a salt therof.

10. The medicament according to claim 8, wherein the aforementioned ligand is comprising an antigen binding domain of an antibody against CD3.

11. The medicament according to claim 9, wherein the aforementioned ligand is comprising an antigen binding domain of an antibody against CD3.

12. The medicament according to claim 8, wherein the aforementioned ligand is comprising an antigen binding domain of an antibody against CD4.

13. The medicament according to claim 9, wherein the aforementioned ligand is comprising an antigen binding domain of an antibody against CD4.

14. The medicament according to claim 8, wherein the aforementioned ligand is comprising an antigen binding domain of an antibody against CD8.

15. The medicament according to claim 9, wherein the aforementioned ligand is comprising an antigen binding domain of an antibody against CD8.

16. The medicament according to claim 8, wherein the aforementioned ligand is comprising an antigen binding domain of an antibody against CD28.

17. The medicament according to claim 9, wherein the aforementioned ligand is comprising an antigen binding domain of an antibody against CD28.

* * * * *